US008258098B2

(12) United States Patent
Faircloth et al.

(10) Patent No.: US 8,258,098 B2
(45) Date of Patent: Sep. 4, 2012

(54) ANTITUMORAL TREATMENTS

(75) Inventors: Glynn Thomas Faircloth, Cambridge, MA (US); Pablo Manuel Aviles Marin, Madrid (ES); Doreen LePage, Cambridge, MA (US); Jesus San Miguel Izquierdo, Salamanca (ES); Atanasio Pandiella, Salamanca (ES)

(73) Assignee: Pharma Mar, S.A., Madrid (ES)

( * ) Notice: Subject to any disclaimer, the term of this patent is extended or adjusted under 35 U.S.C. 154(b) by 339 days.

(21) Appl. No.: 12/278,559

(22) PCT Filed: Feb. 28, 2007

(86) PCT No.: PCT/US2007/062936
§ 371 (c)(1),
(2), (4) Date: Feb. 4, 2009

(87) PCT Pub. No.: WO2007/101235
PCT Pub. Date: Sep. 7, 2007

(65) Prior Publication Data
US 2009/0246168 A1    Oct. 1, 2009

Related U.S. Application Data

(60) Provisional application No. 60/813,606, filed on Feb. 28, 2006.

(51) Int. Cl.
*A61K 38/00* (2006.01)
*A61K 38/12* (2006.01)
*A61K 38/15* (2006.01)
*A61P 35/00* (2006.01)
*A61P 35/02* (2006.01)
*C07K 11/00* (2006.01)
*C07K 11/02* (2006.01)

(52) U.S. Cl. ............ 514/19.2; 514/19.3; 514/19.4; 514/19.5; 514/19.6; 514/19.9; 530/300; 530/317; 530/323

(58) Field of Classification Search .................. None
See application file for complete search history.

(56) References Cited

U.S. PATENT DOCUMENTS

| | | | |
|---|---|---|---|
| 4,493,796 A | 1/1985 | Rinehart | |
| 4,670,262 A | 6/1987 | Battelli | |
| 4,952,399 A | 8/1990 | Lewenstein | |
| 5,294,603 A | 3/1994 | Rinehart | |
| 5,462,726 A | 10/1995 | Lodge | |
| 5,580,871 A | 12/1996 | Earl | |
| 5,834,586 A | 11/1998 | Rinehart et al. | |
| 6,030,943 A | 2/2000 | Crumb | |
| 6,034,058 A | 3/2000 | Rinehart | |
| 6,153,731 A | 11/2000 | Rinehart | |
| 6,156,724 A | 12/2000 | Rinehart | |
| 6,245,759 B1 | 6/2001 | Bilodeau | |
| 6,509,315 B1 | 1/2003 | Joullie et al. | |
| 6,710,029 B1 | 3/2004 | Rinehart | |
| 7,064,105 B2 | 6/2006 | Joullie et al. | |
| 7,122,519 B2 | 10/2006 | Joullie et al. | |
| RE39,887 E | 10/2007 | Rinehart et al. | |
| 7,348,310 B2 | 3/2008 | Rodriguez et al. | |
| 7,348,311 B2 | 3/2008 | Rinehart et al. | |
| 7,381,703 B2 | 6/2008 | Bertino et al. | |
| 7,507,766 B2 | 3/2009 | Lazaro et al. | |
| 7,576,188 B2 | 8/2009 | Bertino et al. | |
| 7,651,997 B2 | 1/2010 | Joullie et al. | |
| 7,678,765 B2 | 3/2010 | Rodriguez et al. | |
| 7,737,114 B2 | 6/2010 | Joullie et al. | |
| 2004/0010043 A1 | 1/2004 | Lazaro | |
| 2005/0004012 A1 | 1/2005 | Mangues et al. | |
| 2006/0019256 A1* | 1/2006 | Clarke et al. | 435/6 |
| 2006/0178298 A1 | 8/2006 | Bertino et al. | |
| 2007/0149446 A1 | 6/2007 | Jouille | |
| 2009/0227490 A1 | 9/2009 | Bertino et al. | |
| 2009/0246168 A1 | 10/2009 | Faircloth et al. | |
| 2009/0298752 A1 | 12/2009 | Faircloth et al. | |
| 2010/0041594 A1 | 2/2010 | Mangues et al. | |
| 2010/0240595 A1 | 9/2010 | Longo Sorbello et al. | |

FOREIGN PATENT DOCUMENTS

| | | |
|---|---|---|
| EP | 0393883 | 10/1990 |
| WO | WO 91/04985 | 4/1991 |
| WO | WO 93/00362 | 1/1993 |
| WO | WO 98/17275 | 4/1998 |
| WO | WO 98/17302 | 4/1998 |
| WO | WO 99/42125 | 8/1999 |
| WO | WO 00/20411 | 4/2000 |
| WO | WO 01/35974 | 5/2001 |
| WO | WO 01/76616 | 10/2001 |
| WO | WO 02/02596 | 1/2002 |
| WO | WO 02/30441 | 4/2002 |
| WO | WO 02/058688 | 8/2002 |
| WO | WO 03/033013 | 4/2003 |
| WO | WO 03/070234 | * 8/2003 |
| WO | WO 2004/080421 | 9/2004 |
| WO | WO 2004/080477 | 9/2004 |

(Continued)

OTHER PUBLICATIONS

Berenbaum (Clin. Exp Immunol. 28:1-18, 1977).*
Wiesenthal (http://weisenthal.org/feedback. html, Feb. 4, 2002).*
Freshney (Culture of Animal Cells, A Manualof Basic Technique, Alan R. Liss, Inc., 1983, New York, p. 4).*
Dermer (Bio/Technology, 1994, 12:320).*
Zips et al. (In vivo, 2005, 19:1-7).*
Byers, T. (CA Cancer Journal, vol. 49, No. 6, Nov./Dec. 1999).*
Kapers, G. et al. (Blood Nov. 16, 2005, 106(11) pt.2, 189B).*
Banerjee, D. et al. (Blood Nov. 16, 2004, 104(11), pt.2, 207B).*

(Continued)

*Primary Examiner* — Peter J Reddig
(74) *Attorney, Agent, or Firm* — Kenneth H. Sonnenfeld; King & Spalding

(57) ABSTRACT

The present invention relates to combinations of aplidine or aplidine analogues with other titumoral agents, and the use of these combinations in the treatment of cancer, in particular in the treatment of lung cancer, breast cancer, colon cancer, prostate cancer, renal cancer, melanoma, multiple myeloma, leukemia and lymphoma.

29 Claims, 56 Drawing Sheets

FOREIGN PATENT DOCUMENTS

| | | |
|---|---|---|
| WO | WO 2007/101235 | 9/2007 |
| WO | WO 2008/080956 | 7/2008 |
| WO | WO 2008/135793 | 11/2008 |
| WO | WO 2010/029158 | 3/2010 |

OTHER PUBLICATIONS

Ribatti and Vacca (Leukemia Jun. 23, 2005 19:1525-1531).*
Kufe et al. (Cancer Medicine 6th ed. Hamilton (ON) BC Decker 2003, NCBI Bookshelf, http://www.ncbi.nlm.nih.gov/books/NBK12772/).*
Tannock, I.F. (Experimental Chemotherapy, Ch. 19-p. 338 and 352-359, in The Basic Science of Oncology Tannock and Hill, eds., New York 1992).*
MeSH-NCBI (aplidine, May 1996).*
Banerjee et al., "Drug Combination Studies with Aplidin in Experimental Leukemia and Lymphoma Models," 5$^{th}$ International Symposium on Leukemia and Lymphoma, vol. 17, No. 3, Mar. 6, 2003.
Banerjee et al., "Potential Clinical Relevance of Drug Combination Studies with Aplidine in Experimental Leukemia and Lymphoma Models," Proceedings of the American Association for Cancer Research Annual Meeting, vol. 44, p. 530, Jul. 2003.
Cheson B.D., "New Chemotherapeutic Agents for the Treatment of Low-Grade Non-Hodgkin's Lymphomas," Seminars in Oncology, vol. 20, No. 5, pp. 96-110, 1993.
"Didemnin B," Drugs of the Future, vol. 17, No. 1, pp. 54-55, 1992.
Vera et al., "Natural Products as Probes of Cell Biology: 20 Years of Didemnin Research," Medicinal Research Reviews, vol. 22, No. 2, pp. 102-145, 2002.
Whelan P., "The Medical Treatment of Metastatic Renal Cell Cancer," EAU Update Series, vol. 1, No. 4, pp. 237-246, 2003.
Yagoda et al., "Cytotoxic Chemotherapy for Advanced Renal Cell Carcinoma," The Urologic Clinics of North America, vol. 20, No. 2, pp. 303-321, 1993.
U.S. Appl. No. 10/398,835, filed Aug. 1, 2003, Lazaro.
U.S. Appl. No. 10/492,659, filed Sep. 1, 2004, Mangues.
U.S. Appl. No. 10/546,750, filed Nov. 4, 2005, Bertino.
Ady-Vago, N. et al., "L-Carnitine as a Protector Against Aplidine Induced Skeletal Muscle Toxicity," Proceedings of the American Association for Cancer Research, vol. 42, pp. 545 (Mar. 2001).
Bergeron, Raymond J. et al., "Antineoplastic and Antiherpetic Activity of Spermidine Catecholamide Iron Chelators," Biochemical and Biophysical Research Communications, vol. 121, No. 3, 848-854, 1984.
Broggini et al., "Aplidine blocks VEGF secretion and VEGF/VEGF-RI autocrine loop in a human leukemic cell line," Clinical Cancer Research, vol. 6, Supplement, Abstract 214, p. 4509s, NCI-EORTC-AACR Symposium on New Drugs in Cancer Therapy, Nov. 7-10, 2000.
Chapa, AM. et al., "Influence of Intravenous L-Carnitine Administration in Sheep Preceding an Oral Urea Drench." Journal of Animal Science, vol. 76, No. 11, pp. 2930-2937, 1998.
da Rocha et al., "Natural Products in Anticancer Therapy", Current Opinion in Pharmacology, vol. 1, pp. 364-369 2001.
Depenbrock, H. et al., "In vitro activity of aplidine, a new marine-derived anti-cancer compound, on freshly explanted clonogenic human tumour cells and haematopoietic-precursor cells," British Journal of Cancer, vol. 78, No. 6, 739-744, 1998.
Erba, E. et al., "Cell cycle phases perturbations induced by new natural marine compounds," Annals of Oncology ,vol. 7, Supplement 1, #283, pp. 82, 1996.
Faircloth, G. et al., "Aplidine (APL) is a novel marine-derived depsipeptide with in vivo antitumor activity," Proceedings of the American Association for Cancer Research. vol. 39, #1551, pp. 227, 1998.
Faircloth, G. et al., "Dehydrodidemnin B (DDB) a new marine derived anti-cancer agent (MDA) with activity against experimental tumor models" and "Biological activity of thiocoraline. A new depsipeptide from a marine micromonospora," Annals of Oncology. vol. 7, Supplement 1, #111 and #112, pp. 34, 1996.
Faircloth, G. et al., "Preclinical characterization of Aplidine (APD), a new marine anticancer depsipeptide (MADEP)," Proceedings of the American Association for Cancer Research, vol. 38, #692, pp. 103, 1997.
Faircloth, G. et al., "Preclinical development of aplidine, a novel marine-derived agent with potent antitumor activity," Annals of Oncology, vol. 9, Supplement 2, #129, pp. 34, 1998.
Faircloth, G. et al., "Schedule-dependency of aplidine, a marine depsipeptide with antitumor activity," Proceedings of the American Association for Cancer Research, vol. 40, #2612, pp. 394-395, 1999.
Geldorf, Albert A. et al., "Cytotoxicity and neurocytotoxicity of new marine anticancer agents evaluated using in vitro assays," Cancer Chemother. Pharmacol. vol. 44, pp. 312-318, 1999.
Genin, Michael J. et al., "Synthesis and Crystal Structure of a Peptidomimetic Containing the (R)-4, 4-Spiro Lactam Type-II β-Turn Mimic," Journal of Organic Chemistry, vol. 58, No. 8, pp. 2334-2337, 1993.
Gomez-Fabre; P.M. et al., "Polamine contents of human breast cancer cells treated with the cytotoxic agents chlorpheniramine and dehydrodidemnin B," Cancer Letters, vol. 113, Nos. 1,2 pp. 141-144, 1997.
Goodman & Gilman's, The Pharacological Basis of Therapeutics, 9$^{th}$ ed., Calabresi et al., Section X, Chemotherapy of Neoplastic Diseases, pp. 1225-1229, 1996.
Hamada et al., "Efficient Total Synthesis of Didemnins A and B", J. Am. Chem. Soc., vol. 111, pp. 669-673 (Jan. 18, 1989).
Harris et al., "The World Health Organization Classification of Hematological Malignancies Report of the Clinical Advisory Committee Meeting, Airlie House, Virginia, Nov. 1997," Modern Pathology, vol. 13, No. 2, pp. 193-207, 2000.
Izbicka et al., "Evaluation of molecular targets for aplidine, a novel anticancer agent," Clinical Cancer Research, vol. 6, Supplement, Abstract 213, p. 4509s, NCI-EORTC-AACR Symposium on New Drugs in Cancer Therapy, Nov. 7-10, 2000.
Izquierdo et al., "Phase I trial of Aplidine (APL) given as a 1 hour (h) intravenous (iv) weekly (wk) infusion in patients (pts) with advanced solid tumors (ST) and lymphoma (NHL)," Clinical Cancer Research, vol. 6, Supplement, Abstract 215, p. 4509s, NCI-EORTC-AACR Symposium on New Drugs in Cancer Therapy, Nov. 7-10, 2000.
Jacob L. "General Pharmacologic Principles". Pharmacology (Fourth Edition). Williams and Wilkins Company, 1996. pp. 1-13.
Jiang et al. "Antitumor Activity of Didemnin B in the Human Tumor Stem Cell Assay". Cancer Chemotherapy and Pharmacology, 1983. 11:1-4.
Jimeno et al., "A correlation of selective antitumor activities of the marine-derived compound Aplidine using different model systems," Proceedings of the 1999 AACR-NCI-EORTC International Conference, Clinical Cancer Research, vol. 5, Supplement, p. 3791s, Abstract 311, Nov. 16-19, 1999.
Jouin et al. "Antineoplastic Activity of Didemnin Congeners: Nordidemnin and Modified Chain Analogues". Journal of Medicinal Chemistry. 1991, 34:486-491.
Jou, Gemma et al., "Total Synthesis of Dehydrodidemnin B. Use of Uronium and Phosphonium Salt Coupling Reagents in Peptide Synthesis in Solution," Journal of Organic Chemistry vol. 62, No. 2, pp. 354-366, 1997.
Lobo, C. et al., "Effect of Dehydrodidemnin B on Human Colon Carcinoma Cell Lines," Anticancer Research vol. 17, No. 1A, pp. 333-336, 1997.
Maroun et al., "Phase I study of aplidine in a 5 day bolus q 3 weeks in patients with solid tumors and lymphomas," Clinical Cancer Research, vol. 6, Supplement, Abstract 216, p. 4509s, NCI-EORTC-AACR Symposium on New Drugs in Cancer Therapy, Nov. 7-10, 2000.
Mastbergen et al., "Cytotoxicity and Neurocytotoxicity of Aplidine, a New Marine Anticancer Agent Evaluated Using in vitro Assays," Annals of Oncology, vol. 9, suppl. 2, #131, 1998.
Montgomery et al., Fed. Prac., vol. 44, p. 634 (1987).
Montgomery, D. W., Zukoski, C. F., Transplantation, vol. 40, pp. 49-56 (1985).
Nujien B. et al., "Pharmaceutical development of Anticancer Agents derived from Marine Sources," Anti-Cancer Drugs, vol. 11, pp. 793-811, 2000.

Osol A. [Editor] "Chapter 27: Structure-Activity Relationship and Drug Design". Remington's Pharmaceutical Sciences (Sixteenth Edition), 1980. pp. 420-435.

Paz-Ares et al., "Phase I clinical and pharmacokinetic study of aplidine, a new marine didemnin, administered as a 24-hour infusion weekly," Clinical Cancer Research, vol. 6, Supplement, Abstract 217, p. 4509s, NCI-EORTC-AACR Symposium on New Drugs in Cancer Therapy, Nov. 7-10, 2000.

Raymond, Eric et al., "Preliminary Results of a Phase I and Pharmacokinetic Study of Aplidine Given as a 24-hour Infusion Every Weeks in Patients with Solid Tumors and Non Hodgkin's Lymphomas," Proceedings of the American Association for Cancer Research, vol. 41, #3886, 2000.

Rinehart, Kenneth L. et al., "Didemnins and Tunichlorin: Novel Natural Products from the Marine Tunicate Trididemnum Solidum," Journal of Natural Products. vol. 51, No. 1, pp. 1-21, 1988.

Rinehart, Kenneth L., Jr. et al., "Didemnins: Antiviral and Antitumor Depsipeptides from a Caribbean Tunicate," Science, vol. 212, No. 4497, pp. 933-935, 1981.

Rinehart, Kenneth L., Jr. et al., "Antiviral and antitumor compounds from tunicates," Federation Proceedings;vol. 42, No. 1, pp. 87-90 1983.

Rinehart, Jr. et al., Pure and Appl. Chem., vol. 54, pp. 2409-2424 (1982).

Rinehart, "Didemnin and its Biological Properties", Escom, pp. 626-631, (1987).

Rinehart, Jr., J. Am. Chem. Soc. vol. 103, pp. 1857-1859 (1981).

Rinehart et al., "Total Synthesis of Didemnins A, B, and C", J. Am. Chem. Soc., vol. 109, pp. 6846-6848 (Oct. 28, 1987).

Sakai et al., "Structure-Activity Relationships of the Didemnins," Journal of Medicinal Chemistry, vol. 39, No. 14, pp. 2819-2834, 1996.

Schmidt et al., "Total Synthesis of the Didemnins-2. Synthesis of Didemnin A, B, C, and Prolyldidemnin A", Tetrahedron Letters, vol. 29, pp. 4407-4408 (1988).

Seebach et al., "Alkylation of Amino Acids Without Loss of the Optical Activity: Preparation of α-Substituted Proline Derivatives. A Case of Self-Reproduction of Chiralty," Journal of the American Chemical Society, vol. 105, No. 16, pp. 5390-5398, 1983.

The Merck Index, Eleventh Ed., p. 489 (1989).

Urdiales et al., "Antiproliferative Effect of Dehydrodidemnin B (DDB), a Depsipeptide Isolated from Mediterranean Tunicates," Cancer Letters, vol. 102, Nos. 1, 2, pp. 31-37, 1996.

Vervoort et al., "Tamandarins A and B: New Cytotoxic Depsipeptides from a Brazilian Ascidian of the Family Didemnidae," The Journal of Organic Chemistry, vol. 65, No. 3, pp. 782-792, 2000.

Weiss et al., "A Phase II Trial of Didemnin B in Myeloma," Investigational New Drugs, vol. 12, No. 1, pp. 41-43, 1994.

U.S. Appl. No. 09/622,433, filed May 10, 2002, Bastian Nguyen.
U.S. Appl. No. 10/492,659, filed Sep. 1, 2004, Ramon Mangues.
U.S. Appl. No. 12/342,478, filed Dec. 23, 2008, Glynn Faircloth.
U.S. Appl. No. 12/433,028, filed Apr. 30, 2009, Joseph Bertino et al.

Alvarez, E. et al. "Aplidin has a dual dose-dependent effect inhibiting cell cycle and inducing apoptosis via Rac1/JNK activation in human melanoma cells", Proceedings of the 98th Annual Meeting of American Association for Cancer Research, AACR; Apr. 14-18, 2007, Abstract No. 5581.

Bergers, G. et al. "Benefits of targeting both pericytes and endothelial cells in the tumor vasculature with kinase inhibitors" J. Clin. Invest. 2003, 111, 1287-1295.

Bogani, C. et al. "Plitidepsin inhibits the growth of cells harboring JAK2V617F mutation", 51st Annual Meeting of American Society of Hematology, ASH, 2009, 114 (22), Abstract No. 3907.

Dumez, H. et al. "Phase II study of biweekly plitidepsin as second-line therapy for advanced or metastatic transitional cell carcinoma of the urothelium", Marine Drugs, 2009, 7(3), 451-463.

Eisen, T. et al. "Phase II study of weekly plitidepsin as second-line therapy for small cell lung cancer", Lung Cancer, 2009, 64(1), 60-65.

Eisen, T. et al. "Phase II study of biweekly plitidepsin as second-line therapy in patients with advanced malignant melanoma", Melanoma Research, 2009, 19(3), 185-192.

Ferme, C. et al. "Plitidepsin activity in peripheral T-cell Lymphoma", TC Lymphoma Forum, Jan. 28-30, 2010.

Geoerger, B. et al. "Phase I-II clinical and pharmacokinetic study of plitidepsin in children with malignant tumors. On behalf of the European ITCC (Innovative therapies for children with cancer) consortium", 44th Annual Meeting of American Society of Clinical Oncology American Association for Cancer Research, ASCO, May 30-Jun. 3, 2008, Abstract No. 10028.

Guillermet-Guibert, J. et al. "Targeting the sphingolipid metabolism to defeat pancreatic cancer cell resistance to the chemotherapeutic gemcitabine drug", Molecular Cancer Therapy, 2009, 8(4), 809-820.

Hartmann, J.T. et al. "An open label, non-comparative phase II study of gemcitabine as salvage treatment for patients with pretreated adult type soft tissue sarcoma", Investigational New Drugs, 2006, 24, 249-253.

Izquierdo MA. et al. "Phase I clinical and pharmacokinetic study of plitidepsin as a 1-hour weekly intravenous infusion in patients with advanced solid tumors", Clinical Cancer Research, 2008, 14(10), 3105-3112.

Lepage, D. et al. "Aplidin combination with chemotherapeutic agents in human renal tumors", Proceedings of the 97th Annual Meeting of American Association for Cancer Research, AACR; Apr. 1-5, 2006, Abstract No. 2133.

Lepage, D. et al. "Aplidin combination with chemotherapeutic agents in human melanoma tumors", Proceedings of the 97th Annual Meeting of American Association for Cancer Research, AACR; Apr. 1-5, 2006, Abstract No. 2134.

LePage, D. J. et al. Evaluation of antitumor activity of Aplidin® combined with Sorafenib in experimental models of renal cancer [abstract]. In: Proceedings of the 99th Annual Meeting of the American Association for Cancer Research; Apr. 12-16, 2008; San Diego, CA. Philadelphia (PA): AACR; 2008. Abstract No. 4013; and the corresponding poster presented in said congress.

Le Tourneau, C. et al. "Aplidine: A paradigm of how to handle the activity and toxicity of a novel marine anticancer poison", Current Pharmaceutical Design, 2007, 13, 3427-3439.

Le Tourneau, C. et al. "Reports of clinical benefit of plitidepsin (aplidine), a new marine-derived anticancer agent, in patients with advanced medullary thyroid carcinoma", American Journal of Clinical Oncology, 2010, 33(2), 132-136.

Longo-Sorbello, G.S.A. et al. "Uptake studies with aplidin, a marine depsipeptide under clinical development", Proceedings of the 98th Annual Meeting of American Association for Cancer Research, AACR; Apr. 14-18, 2007, Abstract No. 1564.

Maier, A. et al. "Evaluation of antitumor efficacy of plitidepsin in vitro in 72 patient derived tumor xenografts using a clonogenic assay and determination of a predictive gene signature", 19th AACR-NCI-EORTC International Conference on Molecular Targets and Cancer Therapeutics, Oct. 22-26, 2007, Abstract No. C61.

Mishra, P.J. et al. "Aplidin potentiates antitumor effect of gemcitabine in vitro as well as in vivo", 19th AACR-NCI-EORTC International Conference on Molecular Targets and Cancer Therapeutics, 2007, Oct. 22-26, Abstract No. C294.

Mishra, P.J. et al. "Synergistic action of plitidepsin and gemcitabine against pancreatic cancer in vitro and in vivo", Proceedings of the 100th Annual Meeting of American Association for Cancer Research, AACR; Apr. 18-22, 2009, Abstract No. 4501.

Mitsiades, C.S. et al. "Aplidin, a marine organism-derived compound with potent antimyeloma activity in vitro and in vivo", Cancer Research, 2008, 68(13), 5216-5225.

Nakahira, S. et al. Involvement of ribonucleotide reductase M1 subunit overexpression in gemcitabine resistance of human pancreatic cancer, International Journal of Cancer, 2007, 120(6), 1355-1363.

Peschel, A. et al. "Phase II study of plitidepsin in pretreated patients with locally advanced or metastatic non-small cell lung cancer", Lung Cancer, 2008, 60, 374-380.

Ray-Coquard, D. et al. "Gemcitabine-based therapy for leiomyosarcomas? For all?", ECCO 15-34th European Society for Medical Oncology, ESMO, 2009, 7(2), 67, Abstract No. 277.

Raymond, E. et al. A phase I and pharmacokinetic study of aplidine (APL) given as a 24-hour continuous infusion every other week (q2w) in patients (pts) with solid tumor (ST) and lymphoma (NHL) [abstract] in: Proceedings of the 11th NCI-EORTC-AACR Symposium on New Drugs in Cancer Therapy; Nov. 7-10, 2000; Amsterdam, NL. Philadelphia (PA):AACR, 2000. Abstract No. 218.

Sasak, H. et al. "Antitumor activity of aplidin in human neuroblastoma tumors", 18$^{th}$ AACR-NCI-EORTC International Conference on Molecular Targets and Cancer Therapeutics, Nov. 7-10, 2006 Abstract No. 514.

Schilder, R.J. et al. "Evaluation of gemcitabine in patients with squamous cell carcinoma of the cervix: a phase II study of the gynecologic oncology group", Gynecologic Oncology, 2000, 76, 204-207.

Staehler et al., "Modern Therapeutic Approaches in Metastatic Renal Cell Carcinoma," European Association of Urology, vol. 5, No. 1, pp. 26-37, 2007.

Taraboletti, R. et al. Aplidine blocks VEGF secretion and VEGF/VEGF-RI autocrine loop in a human leukemic cell line [abstract] in: Proceedings of the 11$^{th}$ NCI-EORTC-AACR Symposium on New Drugs in Cancer Therapy; Nov. 7-10, 2000; Amsterdam, NL. Philadelphia (PA):AACR, 2000. Abstract No. 214.

Verrucci, M. et al. "The marine tunicate-derived cyclic depsipeptide aplidin restores functional hematopoiesis in the marrow of the Gata 1 low mouse model of myelofibrosis", 51$^{th}$ Annual Meeting of American Society of Hematology, ASH, 2009, 114 (22), Abstract No. 3914.

Von Burton, G. et al. "Phase II trial of gemcitabine as first line chemotherapy in patients with metastatic or unresectable soft tissue sarcoma", American Journal of Clinical Oncology, 2006, 29(1), 59-61.

Wagner-Bohn, A. et al. "Phase II study of gemcitabine in children with solid tumors of mesenchymal and embryonic origin", Anticancer Drugs, 2006, 17, 859-864.

Zinzani, P.L. et al. "Gemcitabine as single agent in pretreated T-cell lymphoma patients: evaluation of the long-term outcome", Annals of Oncology, 2010, 21(4), 860-863.

U.S. Appl. No. 07/844,567, filed Apr. 24, 1992, Rinehart.

U.S. Appl. No. 10/550,196, filed Jan. 12, 2007, Joullie.

Clerc et al., "Treatment of Multiple Myeloma," Joint Bone Spine, 70, pp. 175-186, 2003.

Intron® A Interferon alfa-2b, recombinant, Product Information, Schering-Plough Research Institute, 85 pages, Oct. 27, 2004.

Kawasaki et al., "Effects of Long-Term L-Carnitine Treatment on Cardiac Energy Metabolism in Rats with Adriamycin-Induced Heart Failure," Structure and Metabolism of the Cardiac Muscle, pp. 1-6, 1996.

Maroun et al., "Phase I Clinical Study of Didemnin B," Investigational New Drugs, 16(1), pp. 51-56, 1998 (Abstract only).

Nagasawa, "Microenvironmental Niches in the Bone Marrow Required for B-Cell Development," Nature Reviews, Immunology, vol. 6, pp. 107-116, Feb. 2006.

National Cancer Institute, "Cancers by Body Location/System: Hematologic/Blood," retrieved on Mar. 5, 2012 from http://cancer.gov/cancertopics/types/cancersbodylocation/hematologic/print, 2 pages.

Papenhausen et al., "The Advent of Molecular Cytogenetic Techniques has Provided a New Tool for Which Quantitation of Residual Disease or Transplant Monitoring May be the Major Advantage," Cancer Control, Journal of the Moffitt Cancer Center, Sep./Oct. 1997, 13 pages.

Shin et al., "Phase II Clinical Trial of Didemnin B in Previously Treated Small Cell Lung Cancer," Investigational New Drugs, 12(3), pp. 243-249, 1994 (Medline Abstract only).

Taylor et al., "Promoter DNA Methylation of CD10 in Lymphoid Malignancies," Leukemia, 20, pp. 1910-1912, 2006.

* cited by examiner

A

B

|   | Aplidin (nM) | Dexa (nM) | Fa | CI |
|---|---|---|---|---|
| 1 | 0.5 | 5 | 0.5368 | 1.761 |
| 2 | 0.5 | 10 | 0.9535 | 0.559 |
| 3 | 0.5 | 25 | 0.9801 | 0.554 |
| 4 | 1 | 5 | 0.7578 | 1.523 |
| 5 | 1 | 10 | 0.9886 | 0.553 |
| 6 | 1 | 25 | 0.9925 | 0.565 |

A

B

|   | Apli (nM) | Bortz (nM) | Fa | CI |
|---|---|---|---|---|
| 1 | 0.1 | 1 | 0.15 | 1.298 |
| 2 | 0.1 | 2.5 | 0.7 | 1.217 |
| 3 | 0.5 | 1 | 0.53 | 1.585 |
| 4 | 0.5 | 2.5 | 0.917 | 1.108 |
| 5 | 1 | 1 | 0.81 | 1.539 |
| 6 | 1 | 2.5 | 0.93 | 1.393 |

ANTITUMORAL TREATMENTS

FIELD OF THE INVENTION

The present invention relates to combinations of Aplidine or aplidine analogues with other antitumoral agents, and the use of these combinations in the treatment of cancer, in particular in the treatment of lung cancer, breast cancer, colon cancer, prostate cancer, renal cancer, melanoma, multiple myeloma, leukemia and lymphoma.

BACKGROUND OF THE INVENTION

Aplidine (Dehydrodidemnin B) is a cyclic depsipeptide that was isolated from a Mediterranean marine tunicate, *Aplidium albicans*, and it is the subject of WO 9104985. It is related to compounds known as didemnins, and has the following structure:

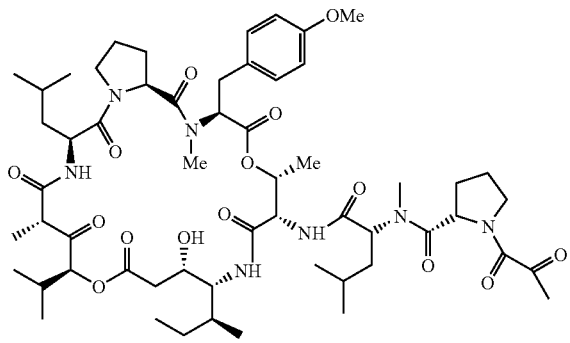

More information on Aplidine, aplidine analogues, its uses, formulations and synthesis can be found in patent applications WO 99 42125, WO 01 35974, WO 01 76616, WO 02 30441, WO 02 02596, WO 03 33013 and WO 2004 080477. We incorporate by specific reference the content of each of these PCT texts.

In both animal preclinical studies and human clinical Phase I studies Aplidine has been shown to have cytotoxic potential against a broad spectrum of tumor types including leukemia and lymphoma. See for example:

Faircloth, G. et al.: "Dehydrodidemnin B (DDB) a new marine derived anticancer agent with activity against experimental tumour models", 9th NCI-EORTC Symp. *New Drugs Cancer Ther.* (March 12-15, Amsterdam) 1996, Abst 111;

Faircloth, G. et al.: "Preclinical characterization of aplidine, a new marine anticancer depsipeptide", *Proc. Amer. Assoc. Cancer Res.* 1997, 38: Abst 692;

Depenbrock H, Peter R, Faircloth G T, Manzanares I, Jimeno J, Hanauske A R.: "In vitro activity of Aplidine, a new marine-derived anti-cancer compound, on freshly explanted clonogenic human tumour cells and haematopoietic precursor cells" *Br. J. Cancer,* 1998; 78: 739-744;

Faircloth G, Grant W, Nam S, Jimeno J, Manzanares I, Rinehart K.: "Schedule-dependency of Aplidine, a marine depsipeptide with antitumor activity", *Proc. Am. Assoc. Cancer Res.* 1999; 40: 394;

Broggini M, Marchini S, D'Incalci M, Taraboletti G, Giavazzi R, Faircloth G, Jimeno J.: "Aplidine blocks VEGF secretion and VEGF/VEGF-R1 autocrine loop in a human leukemic cell line", *Clin. Cancer Res.* 2000; 6 (suppl): 4509;

Erba E, Bassano L, Di Liberti G, Muradore I, Chiorino G, Ubezio P, Vignati S, Codegoni A, Desiderio M A, Faircloth G, Jimeno J and D'Incalci M.: "Cell cycle phase perturbations and apoptosis in tumour cells induced by aplidine", *Br. J. Cancer* 2002; 86: 1510-1517;

Paz-Ares L, Anthony A, Pronk L, Twelves C, Alonso S, Cortes-Funes H, Celli N, Gomez C, Lopez-Lazaro L, Guzman C, Jimeno J, Kaye S.: "Phase I clinical and pharmacokinetic study of aplidine, a new marine didemnin, administered as 24-hour infusion weekly" *Clin. Cancer Res.* 2000; 6 (suppl): 4509;

Raymond E, Ady-Vago N, Baudin E, Ribrag V, Faivre S, Lecot F, Wright T, Lopez Lazaro L, Guzman C, Jimeno J, Ducreux M, Le Chevalier T, Armand J P.: "A phase I and pharmacokinetic study of aplidine given as a 24-hour continuous infusion every other week in patients with solid tumor and lymphoma", *Clin. Cancer Res.* 2000; 6 (suppl): 4510;

Maroun J, Belanger K, Seymour L, Soulieres D, Charpentier D, Goel R, Stewart D, Tomiak E, Jimeno J, Matthews S.: "Phase I study of aplidine in a 5 day bolus q 3 weeks in patients with solid tumors and lymphomas", *Clin. Cancer Res.* 2000; 6 (suppl): 4509;

Izquierdo M A, Bowman A, Martinez M, Cicchella B, Jimeno J, Guzman C, Germa J, Smyth J.: "Phase I trial of Aplidine given as a 1 hour intravenous weekly infusion in patients with advanced solid tumors and lymphoma", *Clin. Cancer Res.* 2000; 6 (suppl): 4509.

Mechanistic studies indicate that Aplidine can block VEGF secretion in ALL-MOLT4 cells and in vitro cytotoxic activity at low concentrations (5 nM) has been observed in AML and ALL samples from pediatric patients with de novo or relapsed ALL and AML. Aplidine appears to induce both a G1 and a G2 arrest in drug treated leukemia cells in vitro. Apart from down regulation of the VEGF receptor, little else is known about the mode(s) of action of Aplidine.

In phase I clinical studies with Aplidine, L-carnitine was given as a 24 hour pretreatment or co-administered to prevent myelotoxicity, see for example WO 02 30441. Co-administration of L-carnitine was proven to be able to improve the recovery of the drug induced muscular toxicity and has allowed for dose escalation of Aplidine.

Previously, in vitro and in vivo assays conducted with Aplidine in combination with other anticancer agents shown that the assayed drug combinations were useful in combination therapy for the treatment of leukemia and lymphoma. In WO 2004 080421, Aplidine was specifically evaluated in combination with methotrexate, cytosine arabinoside, mitoxantrone, vinblastine, methylprednisolone and doxorubicin for the treatment of leukemia and lymphoma.

Since cancer is a leading cause of death in animals and humans, several efforts have been and are still being undertaken in order to obtain an antitumor therapy active and safe to be administered to patients suffering from a cancer. The problem to be solved by the present invention is to provide antitumor therapies that are useful in the treatment of cancer.

SUMMARY OF THE INVENTION

We have established that Aplidine and aplidine analogues potentiates other anticancer agents and therefore can be successfully used in combination therapy for the treatment of cancer. This invention is directed to pharmaceutical compositions, pharmaceutical dosage forms, kits, methods for the treatment of cancer using these combination therapies and uses of Aplidine and aplidine analogues in the manufacture of a medicament for combination therapy.

In accordance with one aspect of this invention, we provide effective combination therapies based on Aplidine and aplidine analogues, using other drugs which are effective in the treatment of cancer. Preferably the other drug or other drugs are effective in the treatment of a cancer selected from lung cancer, breast cancer, colon cancer, prostate cancer, renal cancer, melanoma, multiple myeloma, leukemia and lymphoma. Most preferably the other drug or other drugs are selected from the group consisting of paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab.

In another embodiment the invention encompasses a method of treating cancer comprising administering to a patient in need of such treatment a therapeutically effective amount of Aplidine or an aplidine analogue, or a pharmaceutically acceptable prodrug, salt, solvate or hydrate thereof, and a therapeutically effective amount of another drug which is effective in the treatment of cancer or a pharmaceutically acceptable prodrug, salt, solvate or hydrate thereof, administered prior, during, or after administering Aplidine or aplidine analogue. In an additional embodiment of the invention, a therapeutically effective amount of third drug is administered, and is administered prior, during, or after administering Aplidine or aplidine analogue and the second drug.

Preferably the other drug or other drugs are effective in the treatment of a cancer selected from lung cancer, breast cancer, colon cancer, prostate cancer, renal cancer, melanoma, multiple myeloma, leukemia and lymphoma. Most preferably the other drug or other drugs are selected from the group consisting of paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab. The other drug or other drugs may form part of the same composition, or be provided as a separate composition for administration at the same time or at a different time.

In another aspect the invention encompasses a method of increasing the therapeutic efficacy of a drug effective in the treatment of cancer, preferably a drug effective in the treatment of a cancer selected from lung cancer, breast cancer, colon cancer, prostate cancer, renal cancer, melanoma, multiple myeloma, leukemia and lymphoma, most preferably a drug selected from the group consisting of paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab, or a pharmaceutically acceptable prodrug, salt, solvate or hydrate thereof, which comprises administering to a patient in need thereof an amount of Aplidine or an aplidine analogue, or a pharmaceutically acceptable prodrug, salt, solvate or hydrate thereof. Aplidine or the aplidine analogue is administered prior, during, or after administering the other drug. In an additional embodiment of the invention, a therapeutically effective amount of third drug is administered, and is administered prior, during, or after administering Aplidine or aplidine analogue and the second drug. Preferably the third drug is a drug effective in the treatment of a cancer selected from lung cancer, breast cancer, colon cancer, prostate cancer, renal cancer, melanoma, multiple myeloma, leukemia and lymphoma. Most preferably the third drug is selected from the group consisting of paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab, or a pharmaceutically acceptable prodrug, salt, solvate or hydrate thereof.

In a further aspect the invention encompasses a pharmaceutical composition comprising Aplidine or an aplidine analogue, or a pharmaceutically acceptable prodrug, salt, solvate or hydrate thereof, and another drug effective in the treatment of cancer. In an additional embodiment of the invention, the pharmaceutical composition further comprises a third drug also effective in the treatment of cancer. Preferably the other drug or other drugs are effective in the treatment of a cancer selected from lung cancer, breast cancer, colon cancer, prostate cancer, renal cancer, melanoma, multiple myeloma, leukemia and lymphoma. Most preferably the other drug or other drugs are selected from the group consisting of paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab.

The invention also encompasses a kit for use in the treatment or prevention of cancer which comprises a dosage form of Aplidine or an aplidine analogue, or a pharmaceutically acceptable prodrug, salt, solvate or hydrate thereof, a dosage form of another drug effective in the treatment of cancer, or a pharmaceutically acceptable prodrug, salt, solvate or hydrate thereof, and instructions for the use of each actor in combination for the treatment or prevention of cancer. In an additional embodiment of the invention, the kit further comprises a dosage form of a third drug also effective in the treatment of cancer, or a pharmaceutically acceptable prodrug, salt, solvate or hydrate thereof. Preferably the other drug or other drugs are effective in the treatment of a cancer selected from lung cancer, breast cancer, colon cancer, prostate cancer, renal cancer, melanoma, multiple myeloma, leukemia and lymphoma. Most preferably the other drug or other drugs are selected from the group consisting of paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab.

Effective combination therapies based on the used of three drugs, Aplidine and aplidine analogues, plus two additional drugs (a second drug and a third drug) are also encompassed by the present invention.

In one preferred aspect, the present invention is concerned with synergistic combinations.

DETAILED DESCRIPTION OF THE INVENTION

Figure 1:
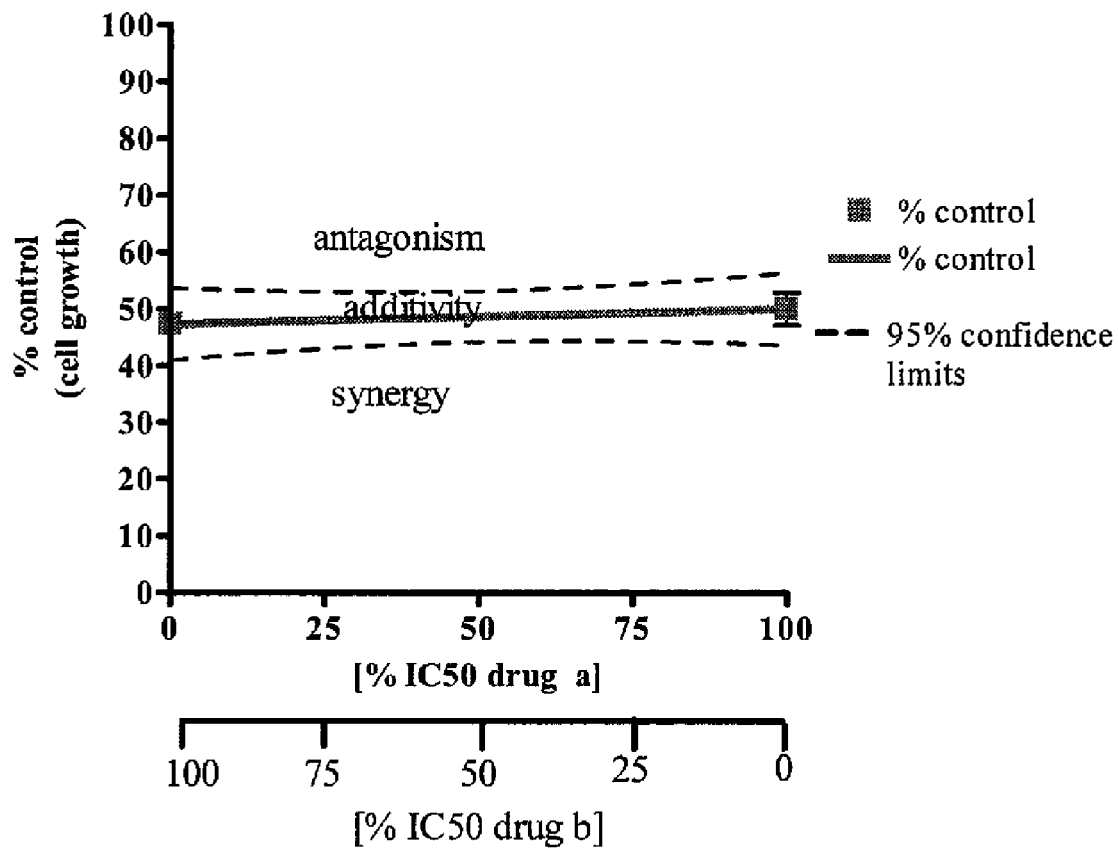
FIG. 1. An example of linear regression analysis which is a method for revealing the presence of synergy.

By "cancer" it is meant to include tumors, neoplasias, and any other malignant tissue or cells. The present invention is directed to the use of Aplidine or an aplidine analogue in combination for the treatments of cancer in general, but more preferably for the treatment of lung cancer, breast cancer, colon cancer, prostate cancer, renal cancer, melanoma, multiple myeloma, leukemia and lymphoma.

In order to study the possible potentiation of other anticancer agents with Aplidine we initiated a systematic study of drug combinations for possible use in the above mentioned cancer types. Drug combination studies were carried out on different types of cell lines. In vitro studies were performed using tumor cells lines such as NSCL A549, breast carcinoma MX1, promyelocytic leukemia HL60, colon adenocarcinoma HT29, prostate adenocarcinoma PC3, breast adenocarcinoma SKBR3 and acute lymphoblastic leukemia (MOLT3), which have different sensitivity to Aplidine (from low to high). Additional studies were also conducted with leukemias, lymphomas, multiple myeloma and melanoma cell lines. In addition, in vivo studies using melanoma, renal, myeloma, and lymphoma xenografts were used to establish the effect of Aplidine in combination with other standard agents. Finally, in vitro studies were conducted in multiple myeloma cell lines using triple combinations, that is combining Aplidine with two additional standard agents (a second and a third drug).

As a general conclusion we found that the cytotoxicity of Aplidine in tumor cells is greatly enhanced in combination with many of the standard agents used for this evaluation. Main synergistic effect was observed with the combination of Aplidine with paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab. Additionally it was also found that an enhancement of the cytotoxicity was also obtained with triple combinations of Aplidine with the above mentioned agents.

Particularly preferred is the combination of Aplidine with paclitaxel in the treatment of cancer, and more particularly in the treatment of a cancer selected from breast cancer, leukemia, and prostate cancer.

Particularly preferred is the combination of Aplidine with doxorubicin in the treatment of cancer, and more particularly in the treatment of a cancer selected from lung cancer, colon cancer, prostate cancer, and multiple myeloma.

Particularly preferred is the combination of Aplidine with cisplatin in the treatment of cancer, and more particularly in the treatment of a cancer selected from breast cancer, and colon cancer.

Particularly preferred is the combination of Aplidine with arsenic trioxide in the treatment of cancer, and more particularly in the treatment of a cancer selected from lung cancer, colon cancer, and prostate cancer.

Particularly preferred is the combination of Aplidine with 5-fluorouracil in the treatment of cancer, and more particularly in the treatment of a cancer selected from leukemia, lung cancer, breast cancer, and prostate cancer.

Particularly preferred is the combination of Aplidine with cytosine arabinoside in the treatment of cancer, and more particularly in the treatment of a cancer selected from lung cancer, breast cancer, and prostate cancer.

Particularly preferred is the combination of Aplidine with carboplatin in the treatment of cancer, and more particularly in the treatment of a cancer selected from colon cancer, prostate cancer, and melanoma.

Particularly preferred is the combination of Aplidine with SN38 in the treatment of cancer, and more particularly in the treatment of lung cancer.

Particularly preferred is the combination of Aplidine with etoposide in the treatment of cancer, and more particularly in the treatment of a cancer selected from lymphoma, and multiple myeloma.

Particularly preferred is the combination of Aplidine with dexamethasone in the treatment of cancer, and more particularly in the treatment of multiple myeloma.

Particularly preferred is the combination of Aplidine with lenalidomide in the treatment of cancer, and more particularly in the treatment of multiple myeloma.

Particularly preferred is the combination of Aplidine with bortezomib in the treatment of cancer, and more particularly in the treatment of multiple myeloma.

Particularly preferred is the combination of Aplidine with dacarbazine in the treatment of cancer, and more particularly in the treatment of melanoma.

Particularly preferred is the combination of Aplidine with bevacizumab in the treatment of cancer, and more particularly in the treatment of renal cancer.

Particularly preferred is the combination of Aplidine with interleukin-2 in the treatment of cancer, and more particularly in the treatment of renal cancer.

Particularly preferred is the combination of Aplidine with melphalan in the treatment of cancer, and more particularly in the treatment of multiple myeloma.

Particularly preferred is the combination of Aplidine with idarubicin in the treatment of cancer, and more particularly in the treatment of leukemia.

Particularly preferred is the combination of Aplidine with rituximab in the treatment of cancer, and more particularly in the treatment of lymphoma.

Particularly preferred is the combination of Aplidine with thalidomide in the treatment of cancer, and more particularly in the treatment of multiple myeloma.

Particularly preferred is the triple combination of Aplidine with lenalidomide and dexamethasone in the treatment of cancer, and more particularly in the treatment of multiple myeloma.

Particularly preferred is the triple combination of Aplidine with bortezomib and dexamethasone in the treatment of cancer, and more particularly in the treatment of multiple myeloma.

Particularly preferred is the triple combination of Aplidine with bortezomib and lenalidomide in the treatment of cancer, and more particularly in the treatment of multiple myeloma.

Particularly preferred is the triple combination of Aplidine with bortezomib and thalidomide in the treatment of cancer, and more particularly in the treatment of multiple myeloma.

Particularly preferred is the triple combination of Aplidine with dexamethasone and thalidomide in the treatment of cancer, and more particularly in the treatment of multiple myeloma.

Particularly preferred is the triple combination of Aplidine with dexamethasone and melphalan in the treatment of cancer, and more particularly in the treatment of multiple myeloma.

Particularly preferred is the triple combination of Aplidine with melphalan and bortezomib in the treatment of cancer, and more particularly in the treatment of multiple myeloma.

The compositions of the present invention may comprise all the components (drugs) in a single pharmaceutically acceptable formulation. Alternatively, the components may be formulated separately and administered in combination with one another. Various pharmaceutically acceptable formulations well known to those of skill in the art can be used in the present invention. Selection of an appropriate formulation for use in the present invention can be performed routinely by those skilled in the art based upon the mode of administration and the solubility characteristics of the components of the composition.

Examples of pharmaceutical compositions containing Aplidine or an aplidine analogue include liquid compositions (solutions, suspensions or emulsions) suitable for intravenous administration, and they may contain the pure compound or in combination with any carrier or other pharmacologically active compounds. Solubilised Aplidine shows substantial degradation under heat and light stress testing conditions, and a lyophilized dosage form was developed, see WO 99 42125 incorporated herein by reference.

Administration of Aplidine or compositions of the present invention is based on a Dosing Protocol preferably by intravenous infusion. We prefer that infusion times of up to 72 hours are used, more preferably 1 to 24 hours, with about 1, about 3 or about 24 hours most preferred. Short infusion times which allow treatment to be carried out without an overnight stay in hospital are especially desirable. However, infusion may be around 24 hours or even longer if required. Infusion may be carried out at suitable intervals with varying patterns, illustratively once a week, twice a week, or more frequently per week, repeated each week optionally with gaps of typically one or several weeks.

The correct dosage of the compounds of the combination will vary according to the particular formulation, the mode of application, and the particular site, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose. Further guidance for the administration of Aplidine is given in WO 01 35974 which is incorporated herein by reference in its entirety.

In one aspect, the present invention relates to synergistic combinations employing Aplidine or an aplidine analogue. An indication of synergy can easily be obtained by testing combinations and analyzing the results, for example by linear regression analysis. Reference is made to FIG. 1 to illustrate this point. Alternative methods such as isobologram analysis are available for revealing synergism and can be employed for the present purposes.

Suitable aplidine analogues include the compounds defined by claim 1 of WO 02 02596, especially the compounds defined by any of the claims dependent on the claim 1. We incorporate by specific reference the disclosure in WO 02 02596 of compounds which are analogues of aplidine, including the claims.

EXAMPLES

Example 1

In vitro studies to determine the effect of Aplidine in combination with another standard agent on tumor cell lines.

Aplidine as a single agent or in combination with selected standard chemotherapeutic agents was evaluated against several tumor cell lines to measure differences in cytotoxicity.

The following standard agents were selected as single agents and for combination with Aplidine: paclitaxel (Taxol®), doxorubicin, cisplatin, arsenic trioxide (Trisonex®), 5-fluorouracil (5-FU), cytosine arabinoside (AraC), carboplatin and 7-ethyl-10-hydroxycamptothecin (SN38).

The single agent Aplidine is cytotoxic to several cancer types with varying potency. For this reason representative tumor cell lines were selected that have a low, medium or high sensitivity to Aplidine. The tumor cell lines that were used are listed in Table 1.

TABLE 1

| Cancer Type (Cell Line) | Sensitivity to Aplidine |
|---|---|
| NSCL (A549) | Low |
| breast carcinoma (MX1) | Low |
| promyelocytic leukemia (HL60) | Medium |
| colon adenocarcinoma (HT29) | Medium |
| prostate adenocarcinoma (PC3) | Medium |
| breast adenocarcinoma (SKBR3) | High |
| acute lymphoblastic leukemia (MOLT3) | High |

The screening was performed in two parts:

a. In the first set of assays, $IC_{50}$ values were determined for each compound after 72 hours of drug exposure in each of the tumor cell lines.

All cell lines were maintained in respective growth media at 37° C., 5% $CO_2$ and 98% humidity. All media formulations did not contain antibiotic. Day before plating cells all cultures were fed with fresh, complete growth media. On the harvest (plating) day cells were counted by Trypan Blue exclusion staining method (basic cell culture). Cells were harvested and seeded in 96 well microtiter plates at 10,000 cells per well in 190 μL of media and incubated for 24 hours to allow the cells to attach before drug addition. Cells were treated with the drugs and the cytotoxic effect was measured by the MTS Assay (Tetrazolium), which is a colorimetric method for determining the number of viable cells. After the 72 hours of incubation with drug, 25 μL of MTS+PMS solution was added to each microtiter well and incubated for 4 hours at 37° C. Plates were then removed from incubator and placed on plate shaker for 5 minutes (covered with aluminium foil for protection from light). Optical densities were read at 490 nm on spectrophotometer plate reader. Data was analysed using SoftMax v 3.12 program.

$IC_{50}$ was calculated, which is approximate equivalent of $IG_{50}$ (concentration at which 50% growth inhibition is measured). A regression curve using SoftMax program was generated, and then 50% inhibition concentration was manually interpolated and converted that concentration to molar (M) by dividing by the molecular weight of the compound. The individual $IC_{50}$ values (72 hours drug exposure) are shown in table 2. The $IC_{50}$ values represent 100% of the drug concentration.

TABLE 2

| Cell Line | Type | Drug | $IC_{50}$ (Molar) |
|---|---|---|---|
| A549 | NSCL tumor | Aplidine | 3.6E−04 |
| | | paclitaxel | 1.3E−08 |
| | | doxorubicin | 1.3E−06 |
| | | cisplatin | 6.0E−06 |
| | | arsenic trioxide | 4.2E−04 |
| | | 5-FU | 1.4E−03 |
| | | AraC | >1.0E−04 |
| | | carboplatin | 3.1E−04 |
| | | SN38 | 1.3E−03 |
| MX1 | breast adenocarcinoma | Aplidine | >1.0E−04 |
| | | paclitaxel | 9.4E−06 |
| | | doxorubicin | >1.0E−04 |
| | | cisplatin | 1.7E−04 |
| | | arsenic trioxide | 9.7E−05 |
| | | 5-FU | >1.0E−04 |
| | | AraC | >1.0E−04 |
| | | carboplatin | >1.0E−04 |
| | | SN38 | 1.5E−07 |
| HL60 | promyelocytic leukemia | Aplidine | 3.0E−09 |
| | | paclitaxel | 1.6E−08 |
| | | doxorubicin | >1.0E−04 |
| | | cisplatin | 1.2E−05 |
| | | arsenic trioxide | 2.0E−05 |
| | | 5-FU | 1.2E−03 |
| | | AraC | 1.0E−05 |
| | | carboplatin | 5.6E−05 |
| | | SN38 | <1.0E−06 |
| HT29 | colon adenocarcinoma | Aplidine | >1.0E−04 |
| | | paclitaxel | 5.0E−09 |
| | | doxorubicin | >1.0E−04 |
| | | cisplatin | 7.2E−04 |
| | | arsenic trioxide | 8.0E−05 |
| | | 5-FU | 8.8E−04 |
| | | AraC | >1.0E−04 |
| | | carboplatin | 2.6E−04 |
| | | SN38 | 1.2E−07 |

TABLE 2-continued

| Cell Line | Type | Drug | IC$_{50}$ (Molar) |
|---|---|---|---|
| PC3 | Prostate tumor | Aplidine | 7.8E−08 |
| | | paclitaxel | Not determined |
| | | doxorubicin | 1.1E−05 |
| | | cisplatin | 8.7E−05 |
| | | arsenic trioxide | 1.2E−03 |
| | | 5-FU | 2.2E−04 |
| | | AraC | >1.0E−04 |
| | | carboplatin | >1.0E−04 |
| | | SN38 | 4.6E−05 |
| SKBR3 | breast adenocarcinoma | Aplidine | 2.0E−09 |
| | | paclitaxel | >1.0E−04 |
| | | doxorubicin | 2.9E−07 |
| | | cisplatin | 7.0E−06 |
| | | arsenic trioxide | 1.0E−04 |
| | | 5-FU | 1.8E−05E |
| | | AraC | >1.0E−04 |
| | | carboplatin | 5.2E−05 |
| | | SN38 | <1.0E−11 |
| MOLT3 | acute lymphoblastic leukemia | Aplidine | 4.9E−14 |
| | | paclitaxel | 7.7E−05 |
| | | doxorubicin | 6.9E−09 |
| | | cisplatin | 5.7E−07 |
| | | arsenic trioxide | 3.7E−06 |
| | | 5-FU | 1.1E−05 |
| | | AraC | 2.2E−07 |
| | | carboplatin | 4.0E−06 |
| | | SN38 | 1.0E−06 | b. In a second set of assays, each cell line was incubated with Aplidine in combination with each of the standard agents mentioned above in the following combinations of unique IC$_{50}$ concentrations:

| IC$_{50}$ of Aplidine | IC$_{50}$ of Standard Agent |
|---|---|
| 100% | 0% |
| 75% | 25% |
| 60% | 40% |
| 50% | 50% |
| 40% | 60% |
| 30% | 70% |
| 25% | 75% |
| 0% | 100% |
| 0% | 0% |

The microtiter plates were incubated for 72 hrs, at 5% CO$_2$ and 37° C. The cytotoxic effect was measured by MTS Assay. Optical densities read at 490 nm. Normalized data was plotted and interpreted as described. Data was analysed as:
1. Prism (Graphpad) software program was used to normalized the data to control values (100%=cell growth in the absence of agent (drug); 0%=blank control).
2. Data normalized were plotted as scatter plots. A line was drawn connecting the values of 100% IC$_{50}$ for each agent (drug). Values significantly above the line indicated antagonism, below indicated synergy, and on the line indicated additivity.

Statistical treatment of data followed Laska E. et al. Biometrics (1994) 50:834-841 and Greco et al. Pharmacol Rev. (1995) 47: 331-385. Combinations at tested dose ratios were judged to be synergistic when inhibition of cell proliferation exceeded maximum inhibition values for each drug separately (at 100% IC$_{50}$). Conversely, antagonism was concluded when inhibition was lower than both maxima. Additivity was concluded when the effects of combinations did not differ significantly from the maxima for both drugs. Statistical significance was assessed by performing a student's t-test on the inhibition at each dose ratio versus the inhibition at the maximum for each drug. Overall significance of drug combinations for each cell line was dependent on showing statistical significance for greater than 50% of dose ratios.

As a visual aid, response values were plotted on a scatter plot with dose ratios given on the x-axis and % response values on the y-axis. A horizontal line was drawn between the two endpoint response values (E.g. between the response values for 100% IC$_{50}$ Aplidine and 100% IC$_{50}$ standard chemotherapeutic agent). In cases where response values at the two endpoints were approximately equivalent, points lying above or below this predicted line of additivity could be interpreted as representing antagonistic or synergistic drug interaction, respectively.

The in vitro combinations of each drug with Aplidine have the potential to be synergistic, additive or antagonistic. Synergistic cytotoxicity to tumor cells is an optimal effect and implies that the combination of Aplidine with another drug is more effective than either drug alone.

Figure 2:
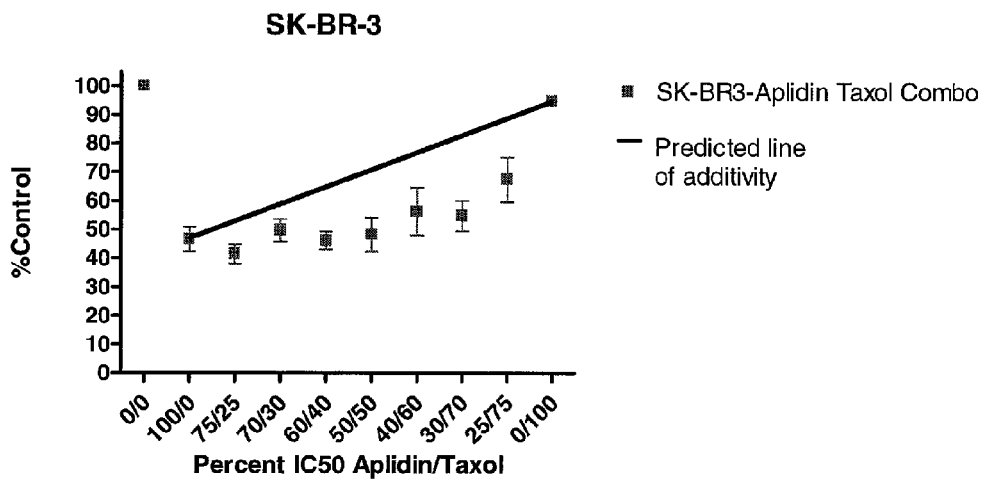
FIG. 2. In vitro activity data of Aplidine (Aplidin®) in combination with paclitaxel (Taxol®) against SKBR3 cells.
Figure 3:
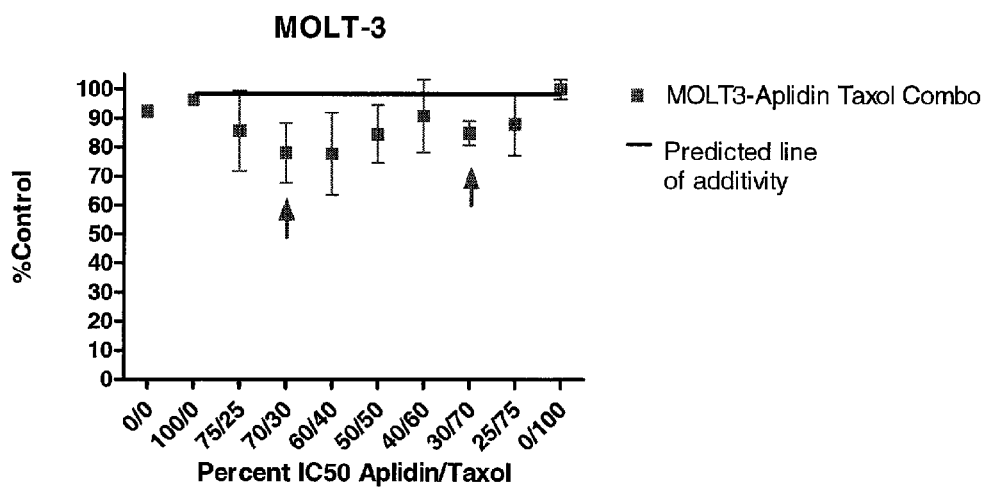
FIG. 3. In vitro activity data of Aplidine (Aplidin®) in combination with paclitaxel (Taxol®) against MOLT3 cells.
Figure 4:
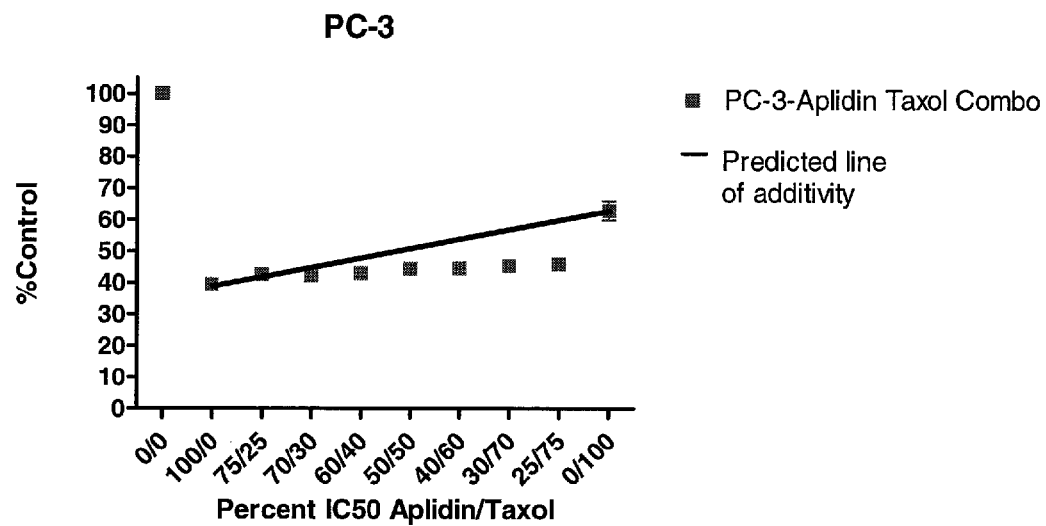
FIG. 4. In vitro activity data of Aplidine (Aplidin®) in combination with paclitaxel (Taxol®) against PC3 cells.
Figure 5:
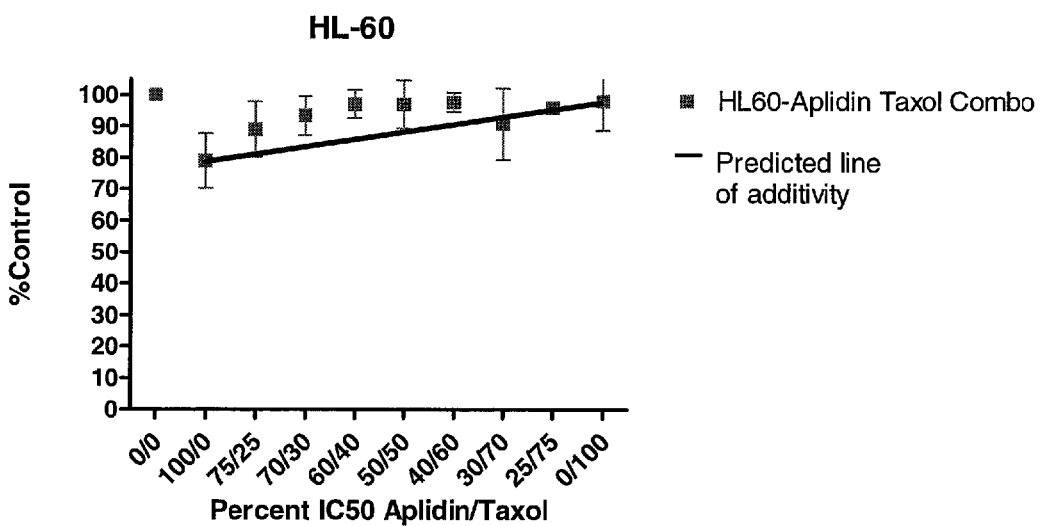
FIG. 5. In vitro activity data of Aplidine (Aplidin®) in combination with paclitaxel (Taxol®) against HL60 cells.
Figure 6:
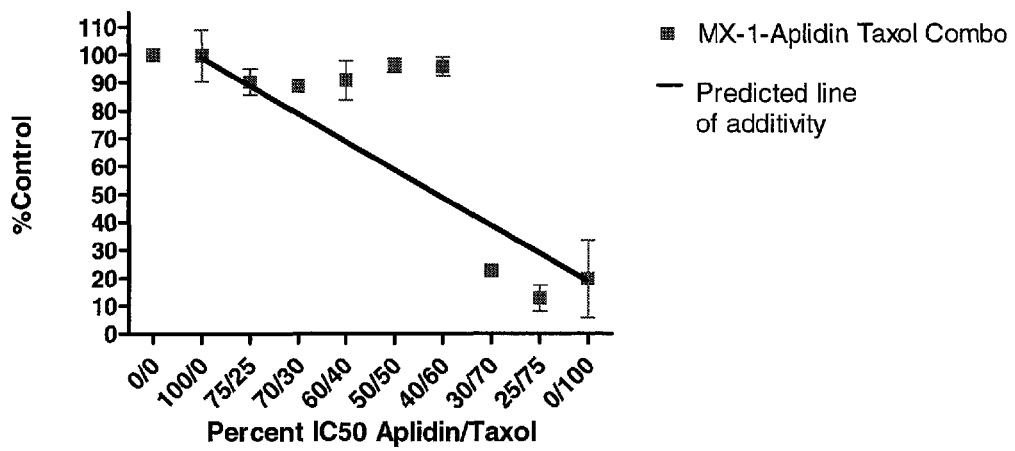
FIG. 6. In vitro activity data of Aplidine (Aplidin®) in combination with paclitaxel (Taxol®) against MX1 cells.
Figure 7:
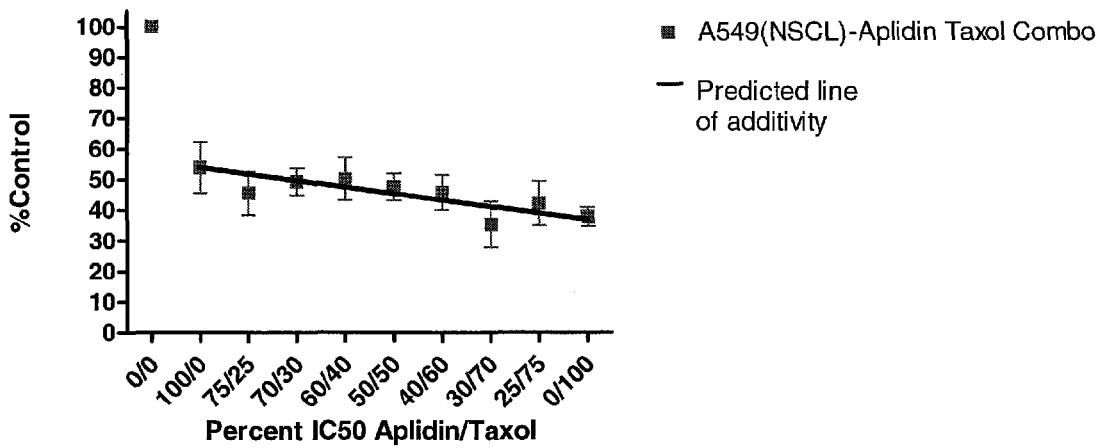
FIG. 7. In vitro activity data of Aplidine (Aplidin®) in combination with paclitaxel (Taxol®) against A549 cells.
Figure 8:
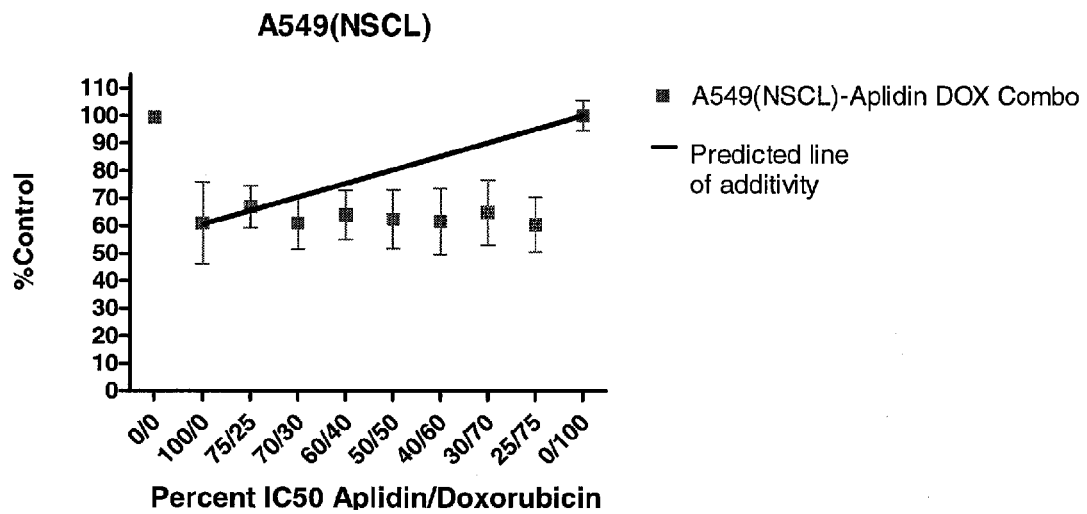
FIG. 8. In vitro activity data of Aplidine (Aplidin®) in combination with doxorubicin (DOX) against A549 cells.
Figure 9:
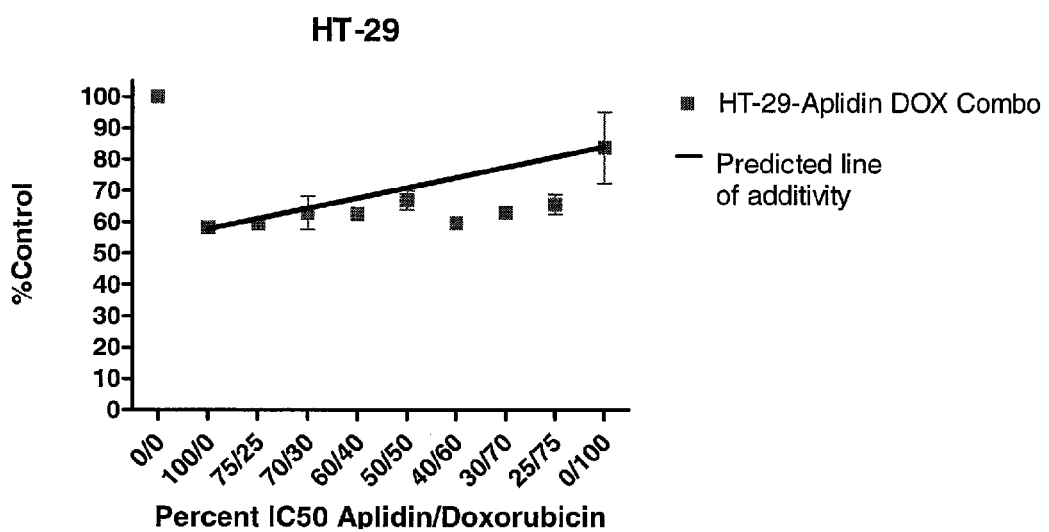
FIG. 9. In vitro activity data of Aplidine (Aplidin®) in combination with doxorubicin (DOX) against HT29 cells.
Figure 10:
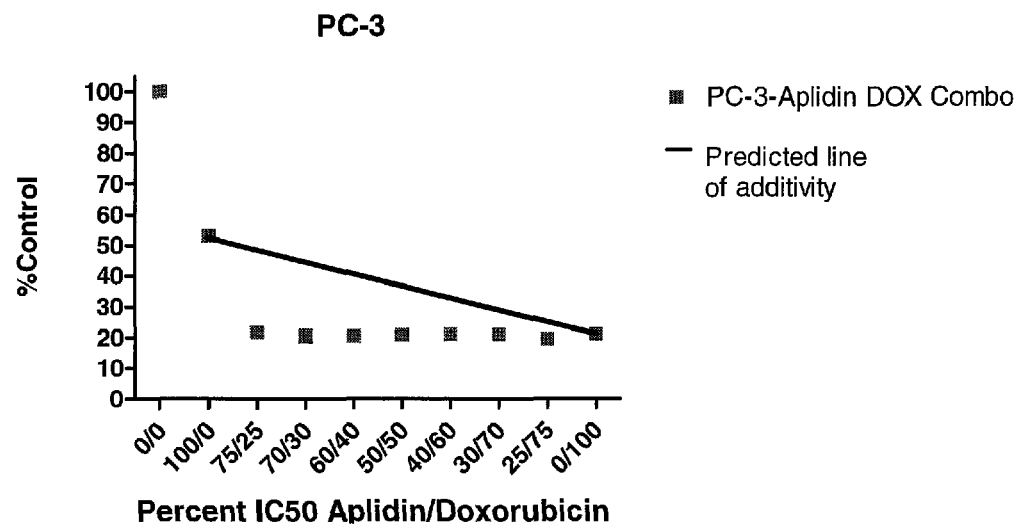
FIG. 10. In vitro activity data of Aplidine (Aplidin®) in combination with doxorubicin (DOX) against PC3 cells.
Figure 11:
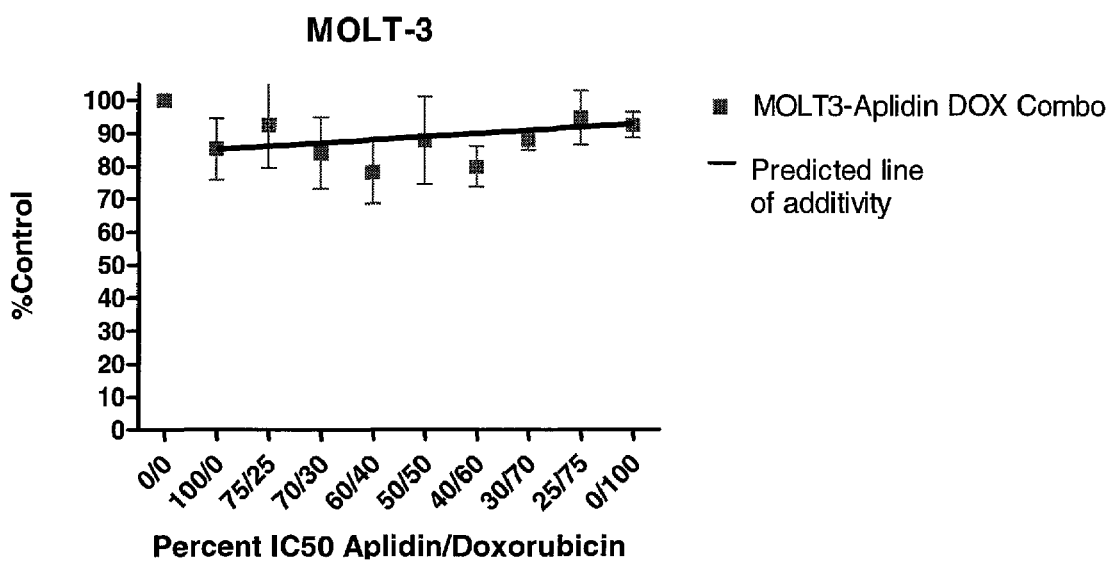
FIG. 11. In vitro activity data of Aplidine (Aplidin®) in combination with doxorubicin (DOX) against MOLT3 cells.
Figure 12:
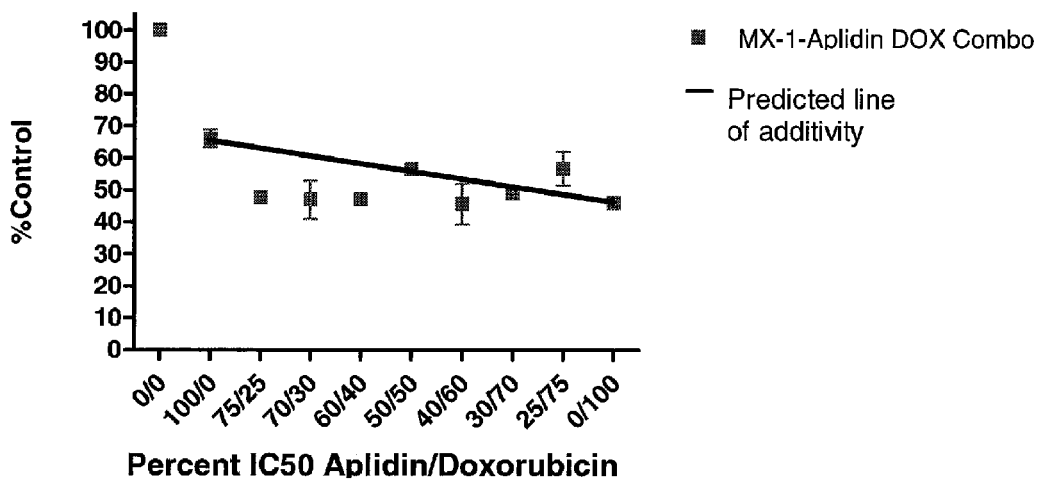
FIG. 12. In vitro activity data of Aplidine (Aplidin®) in combination with doxorubicin (DOX) against MX1 cells.
Figure 13:
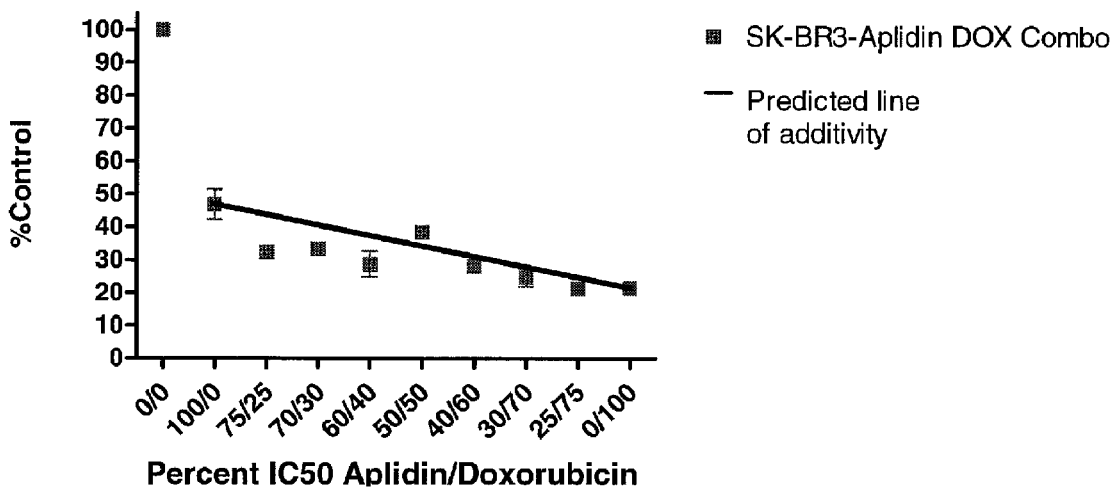
FIG. 13. In vitro activity data of Aplidine (Aplidin®) in combination with doxorubicin (DOX) against SKBR3 cells.
Figure 14:
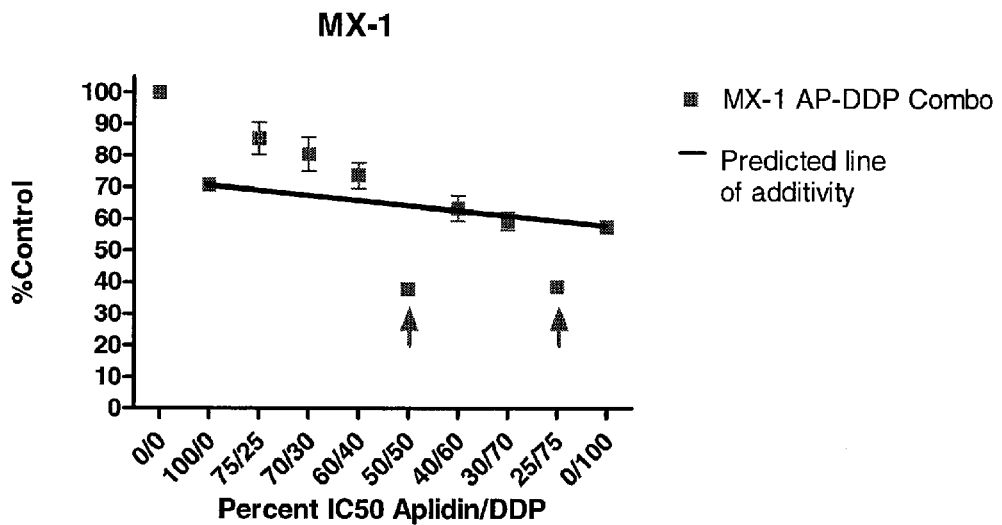
FIG. 14. In vitro activity data of Aplidine (AP, Aplidin®) in combination with cisplatin (DDP) against MX1 cells.
Figure 15:
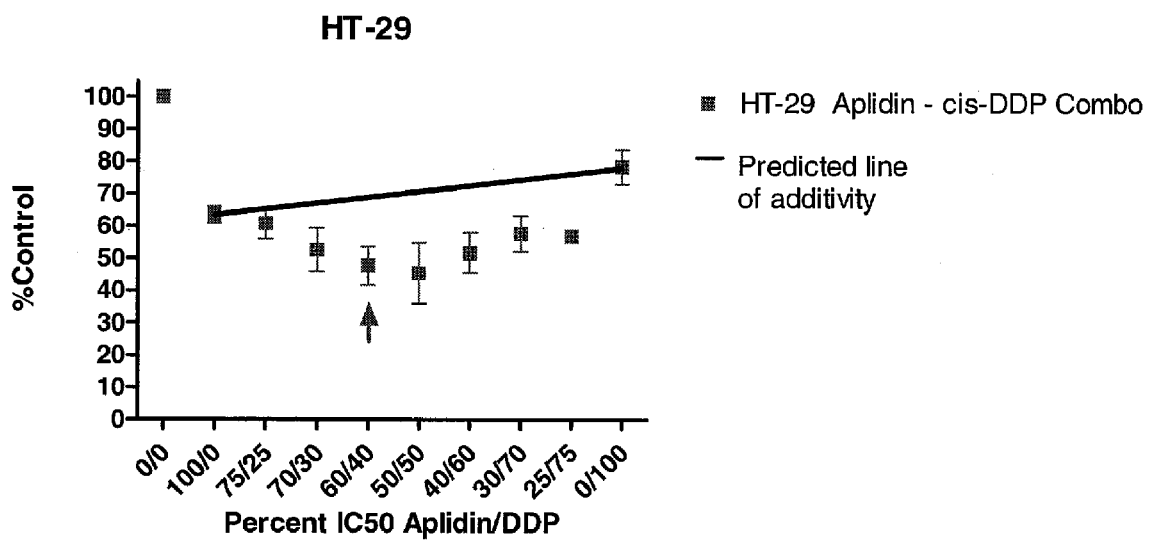
FIG. 15. In vitro activity data of Aplidine (Aplidin®) in combination with cisplatin (cis-DDP) against HT29 cells.
Figure 16:
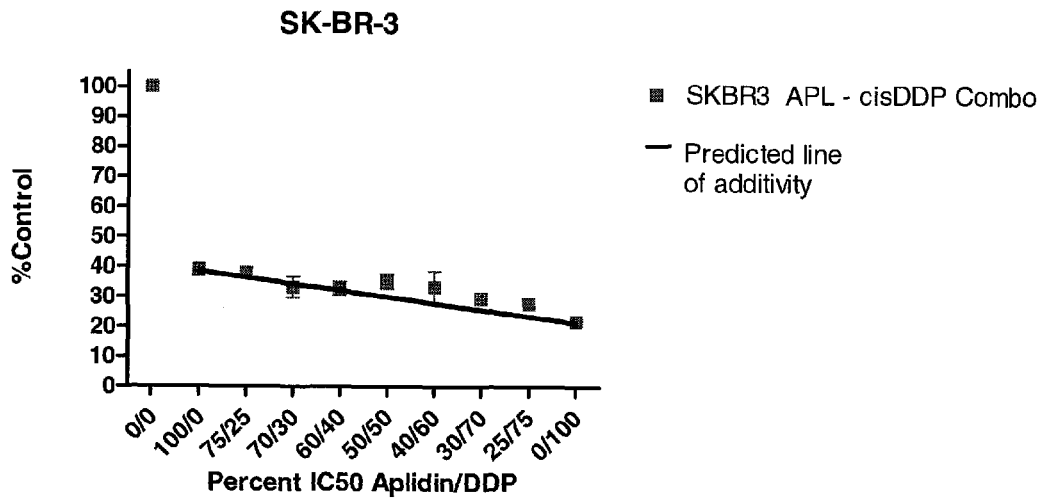
FIG. 16. In vitro activity data of Aplidine (APL, Aplidin®) in combination with cisplatin (cisDDP, DDP) against SKBR3 cells.
Figure 17:
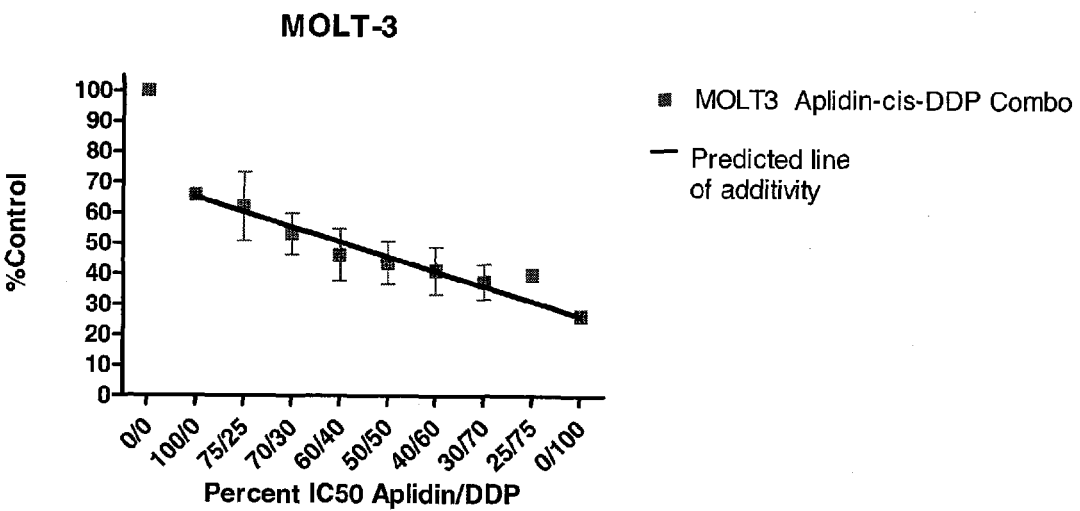
FIG. 17. In vitro activity data of Aplidine (Aplidin®) in combination with cisplatin (cis-DDP, DDP) against MOLT3 cells.
Figure 18:
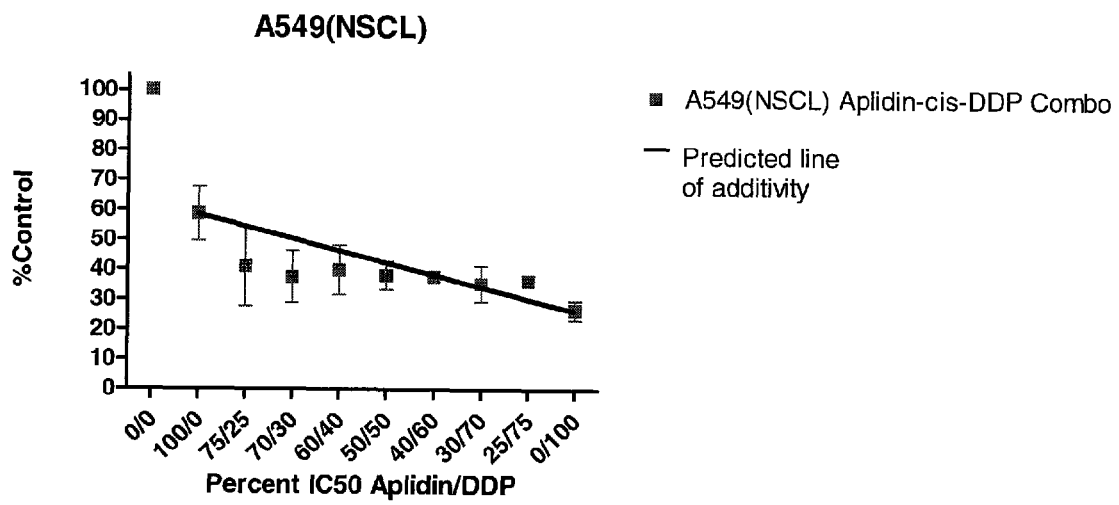
FIG. 18. In vitro activity data of Aplidine (Aplidin®) in combination with cisplatin (cis-DDP, DDP) against A549 cells.
Figure 19:
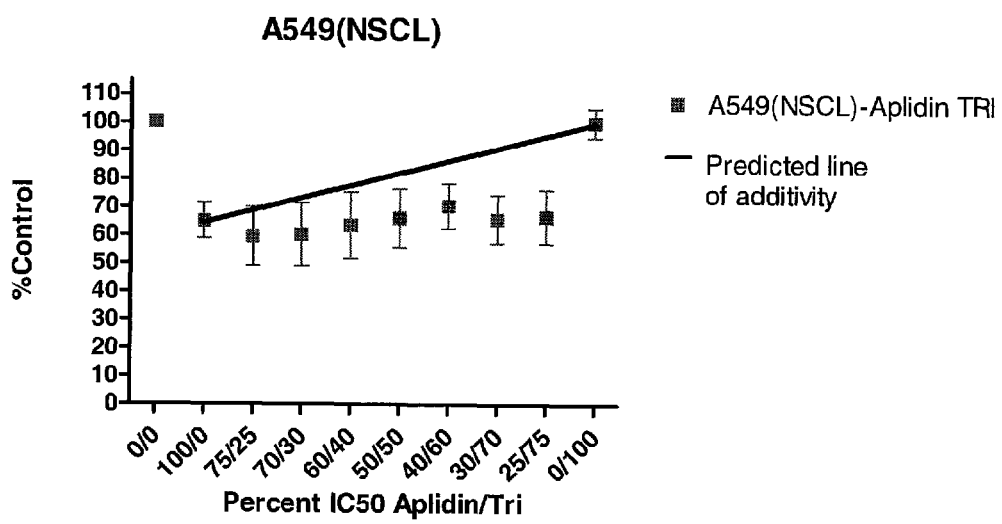
FIG. 19. In vitro activity data of Aplidine (Aplidin®) in combination with arsenic trioxide (TRI) against A549 cells.
Figure 20:
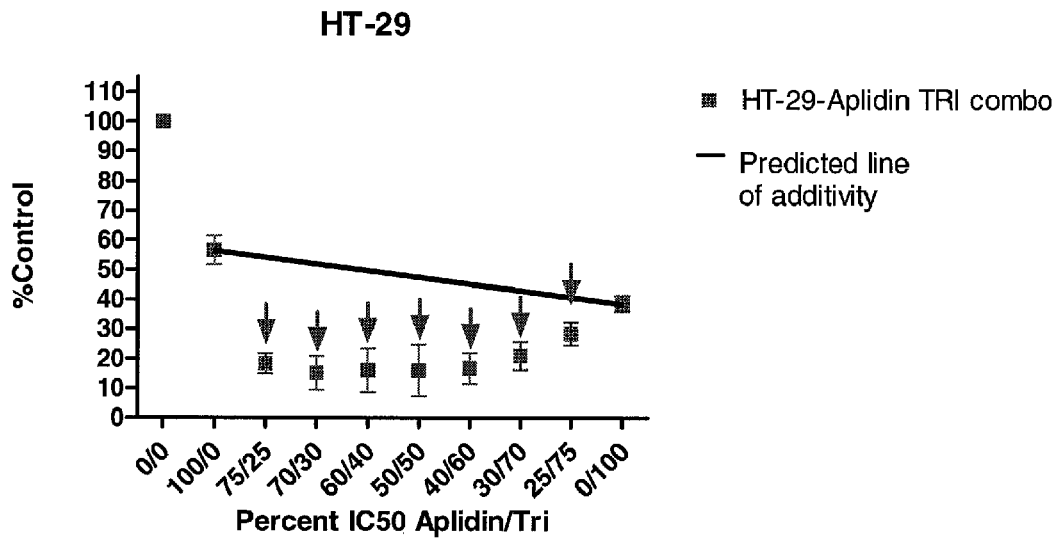
FIG. 20. In vitro activity data of Aplidine (Aplidin®) in combination with arsenic trioxide (TRI) against HT29 cells.
Figure 21:
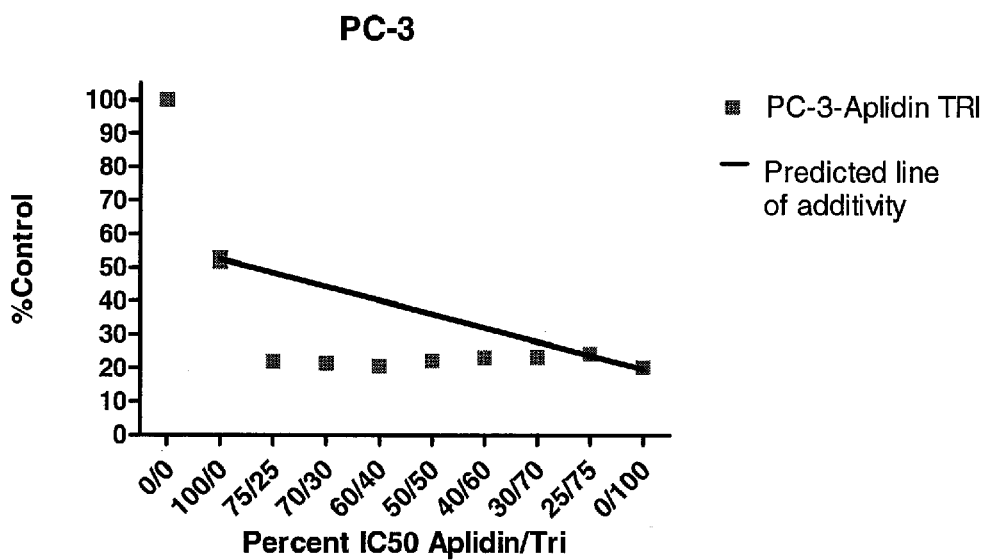
FIG. 21. In vitro activity data of Aplidine (Aplidin®) in combination with arsenic trioxide (TRI) against PC3 cells.
Figure 22:
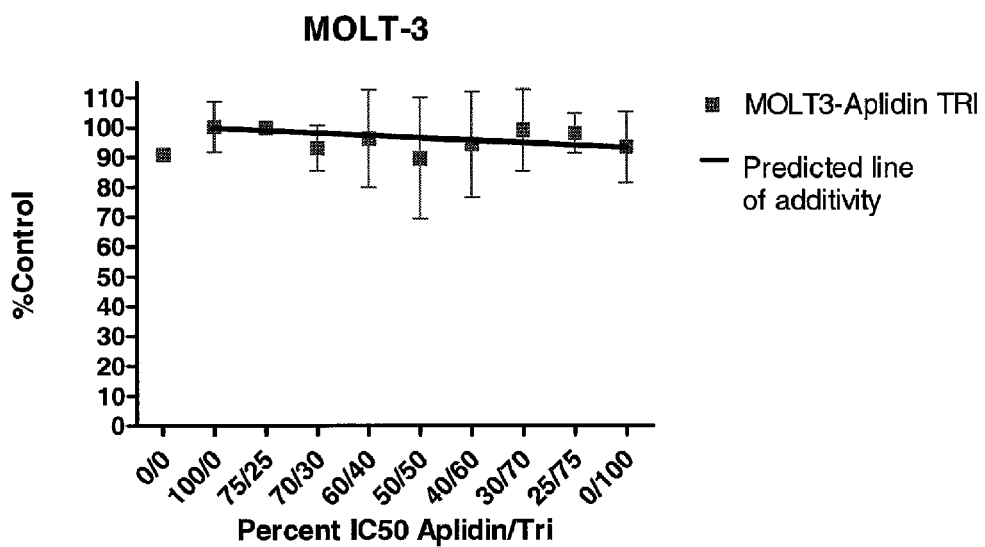
FIG. 22. In vitro activity data of Aplidine (Aplidin®) in combination with arsenic trioxide (TRI) against MOLT3 cells.
Figure 23:
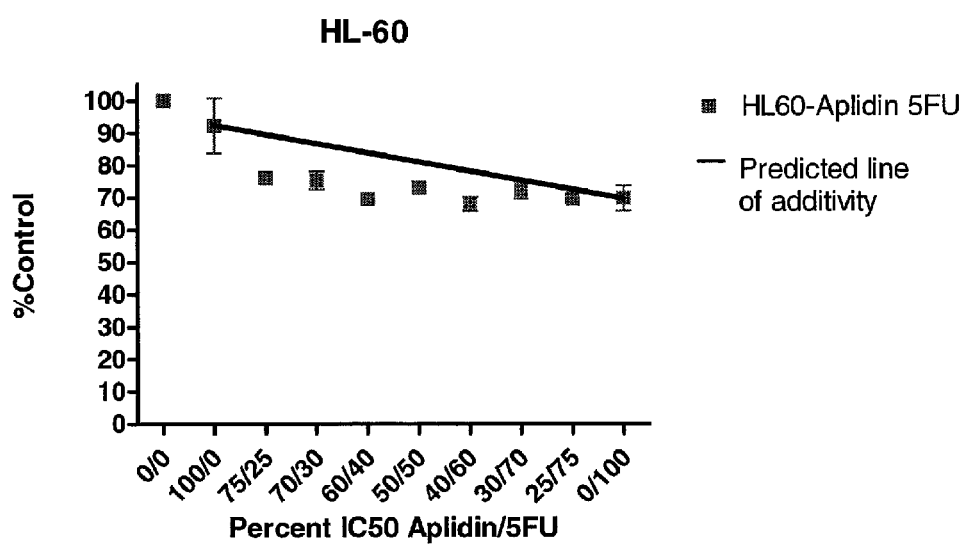
FIG. 23. In vitro activity data of Aplidine (Aplidin®) in combination with 5-fluorouracil (5FU) against HL60 cells.
Figure 24:
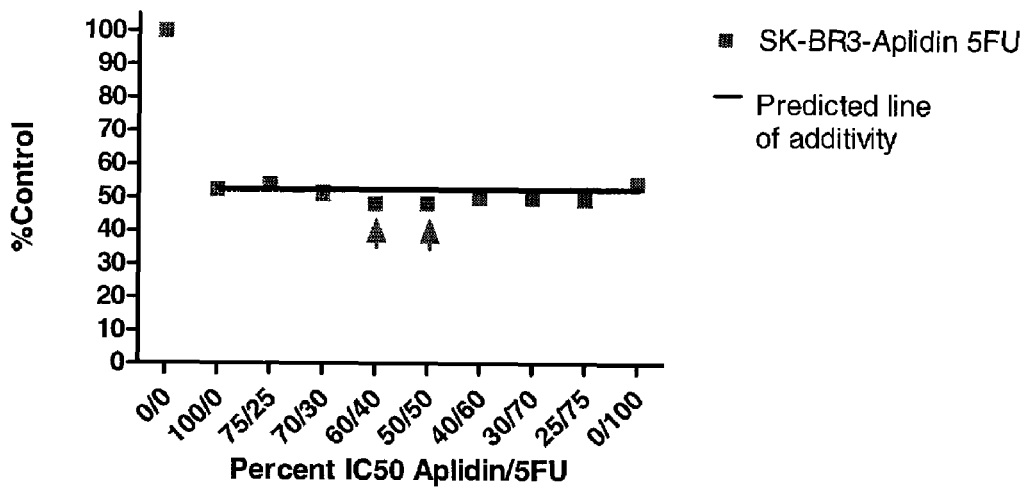
FIG. 24. In vitro activity data of Aplidine (Aplidin®) in combination with 5-fluorouracil (5FU) against SKBR3 cells.
Figure 25:
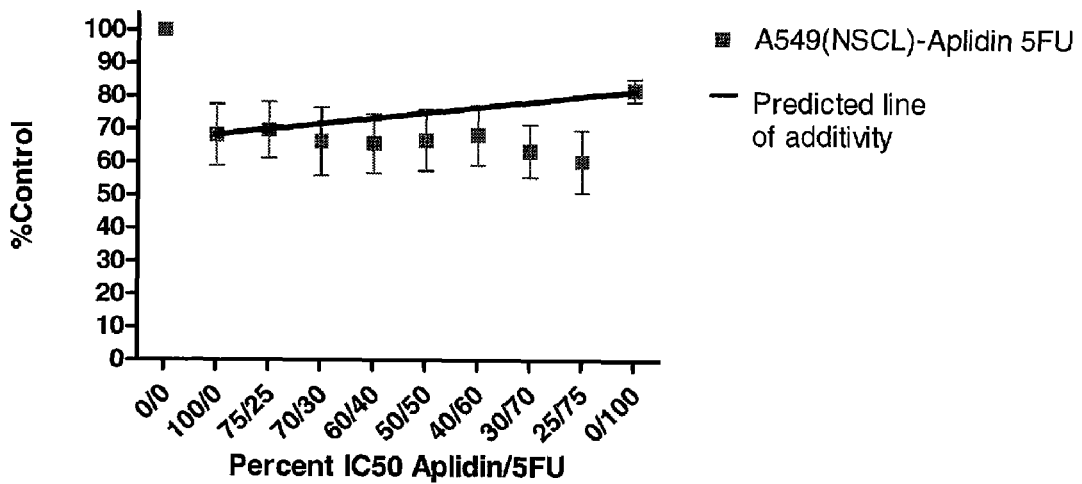
FIG. 25. In vitro activity data of Aplidine (Aplidin®) in combination with 5-fluorouracil (5FU) against A549 cells.
Figure 26:
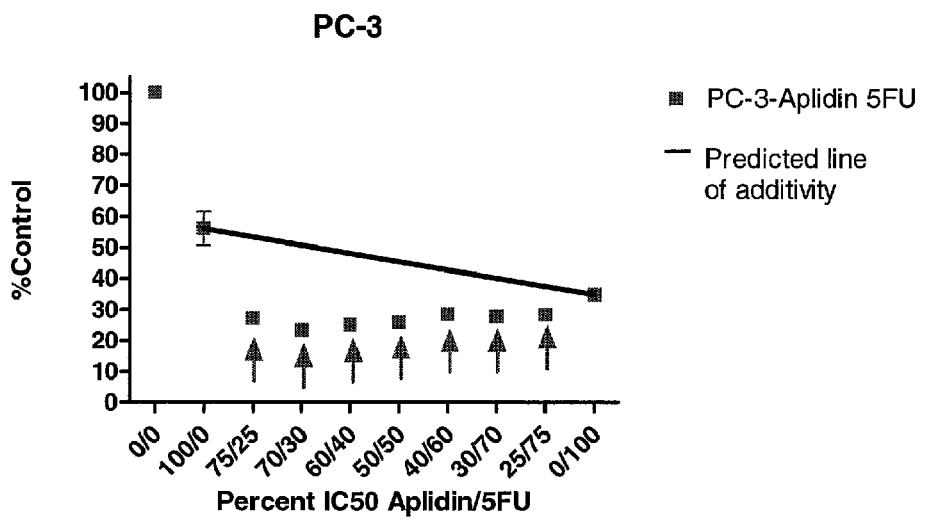
FIG. 26. In vitro activity data of Aplidine (Aplidin®) in combination with 5-fluorouracil (5FU) against PC3 cells.
Figure 27:
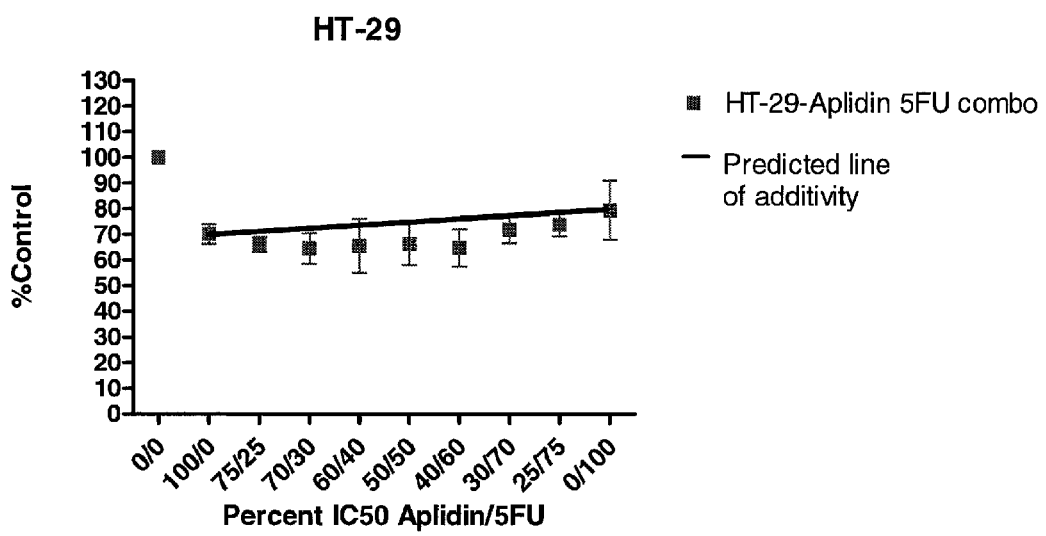
FIG. 27. In vitro activity data of Aplidine (Aplidin®) in combination with 5-fluorouracil (5FU) against HT29 cells.
Figure 28:
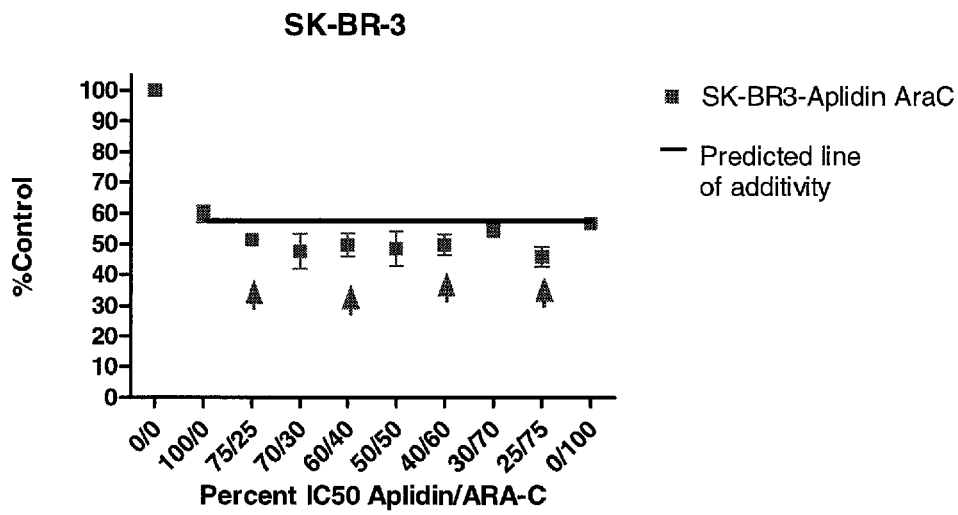
FIG. 28. In vitro activity data of Aplidine (Aplidin®) in combination with cytosine arabinoside (AraC) against SKBR3 cells.
Figure 29:
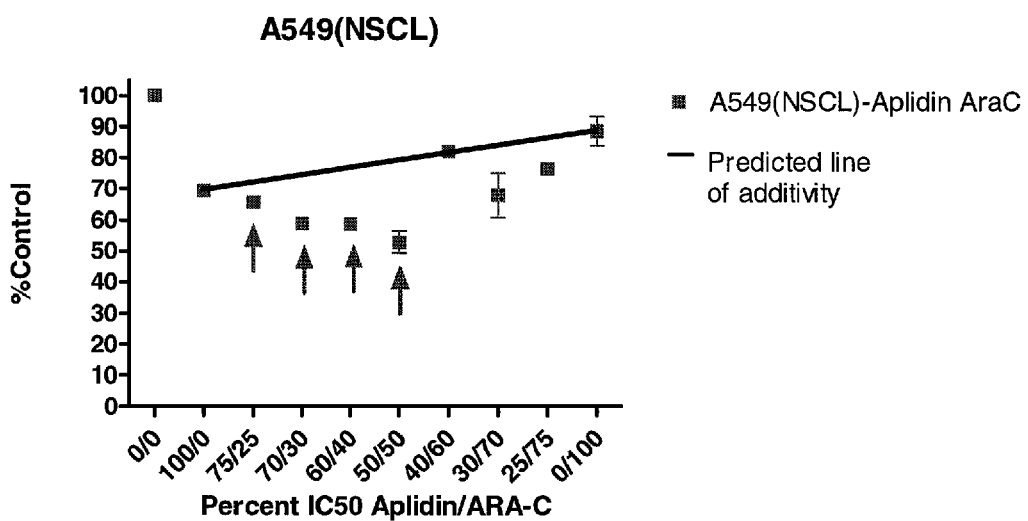
FIG. 29. In vitro activity data of Aplidine (Aplidin®) in combination with cytosine arabinoside (AraC) against A549 cells.
Figure 30:
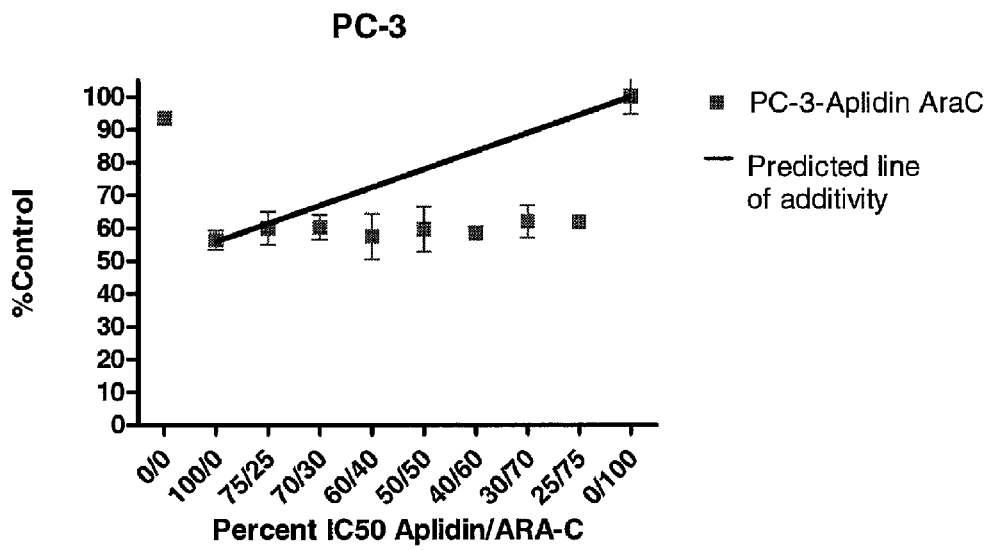
FIG. 30. In vitro activity data of Aplidine (Aplidin®) in combination with cytosine arabinoside (AraC) against PC3 cells.
Figure 31:
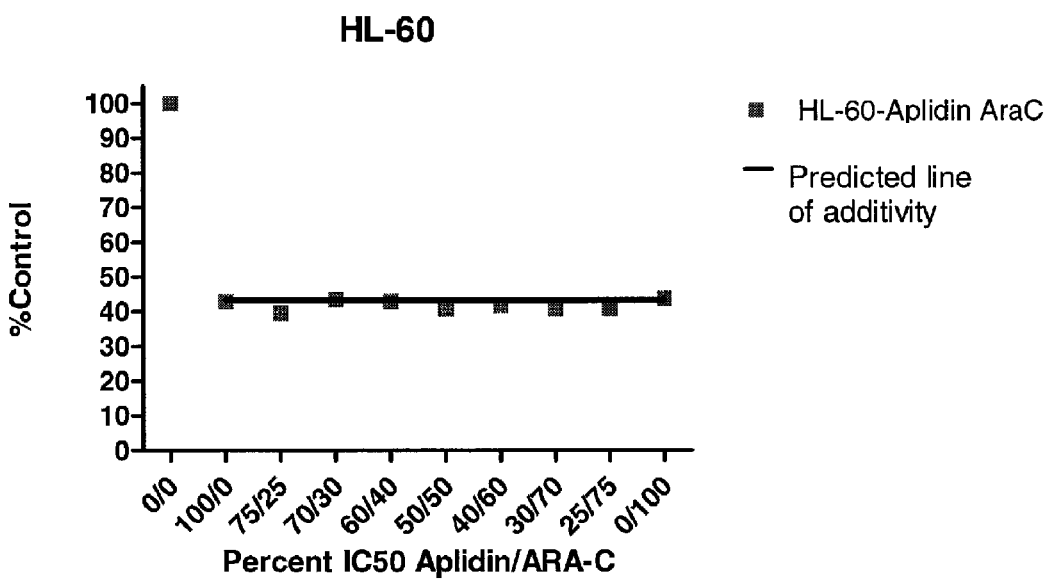
FIG. 31. In vitro activity data of Aplidine (Aplidin®) in combination with cytosine arabinoside (AraC) against HL60 cells.
Figure 32:
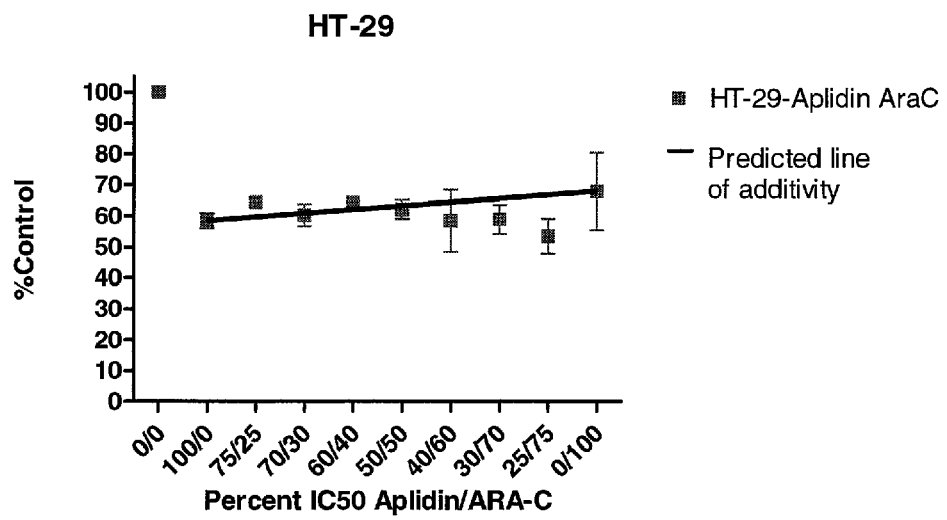
FIG. 32. In vitro activity data of Aplidine (Aplidin®) in combination with cytosine arabinoside (AraC) against HT29 cells.
Figure 33:
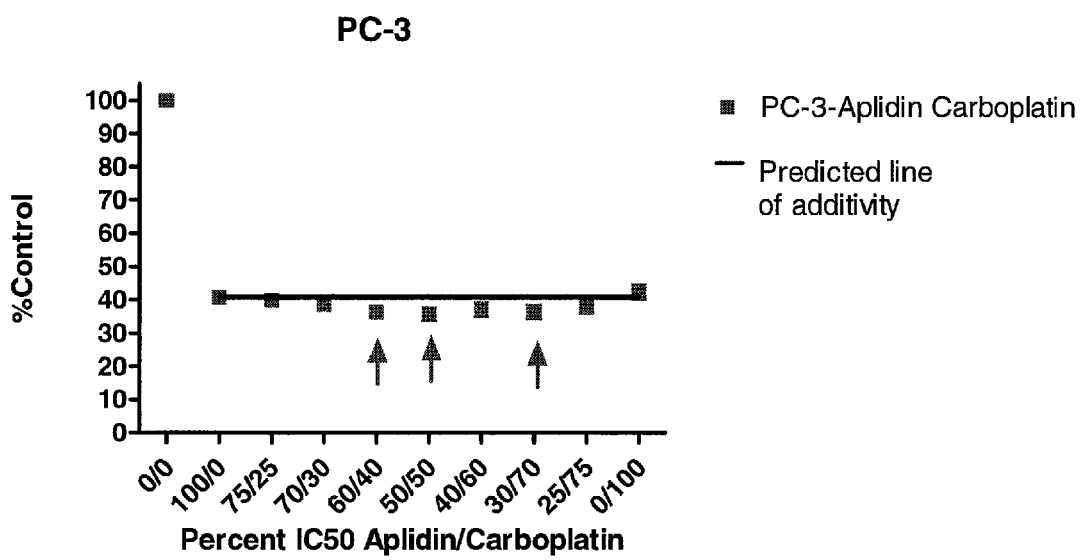
FIG. 33. In vitro activity data of Aplidine (Aplidin®) in combination with carboplatin against PC3 cells.
Figure 34:
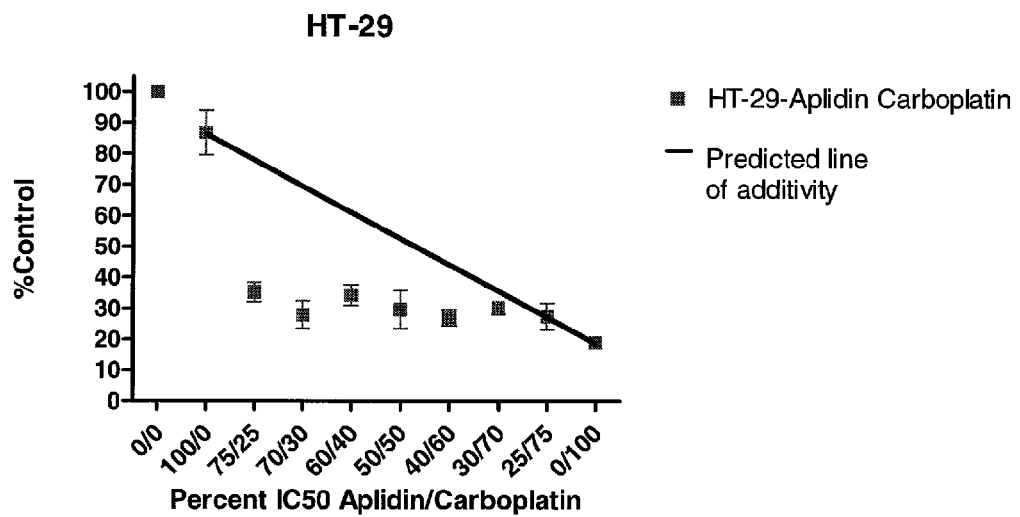
FIG. 34. In vitro activity data of Aplidine (Aplidin®) in combination with carboplatin against HT29 cells.
Figure 35:
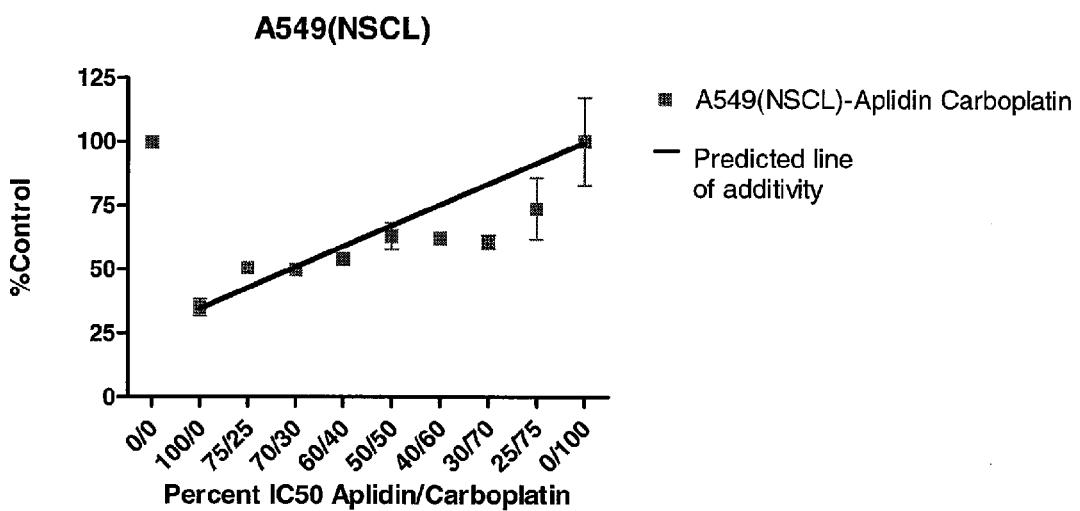
FIG. 35. In vitro activity data of Aplidine (Aplidin®) in combination with carboplatin against A549 cells.
Figure 36:
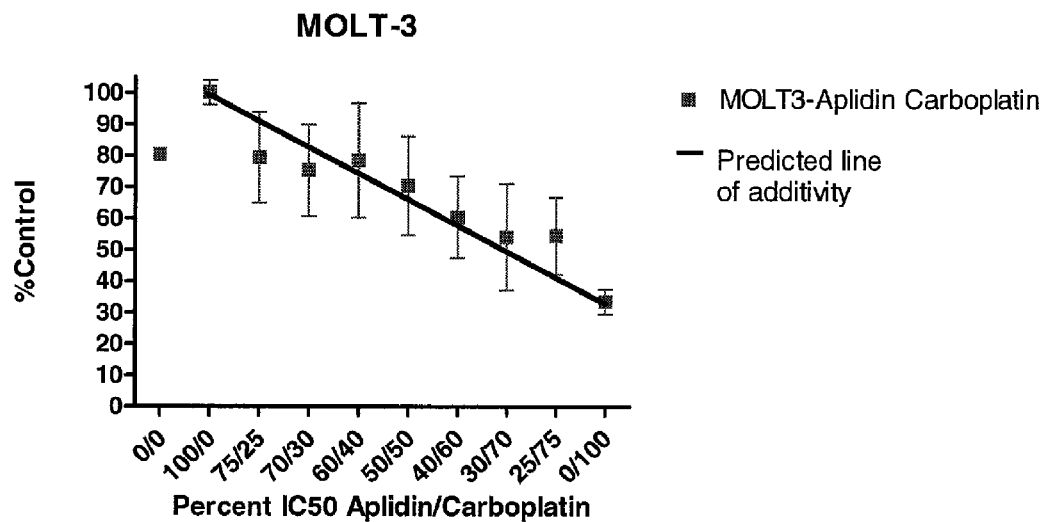
FIG. 36. In vitro activity data of Aplidine (Aplidin®) in combination with carboplatin against MOLT3 cells.
Figure 37:
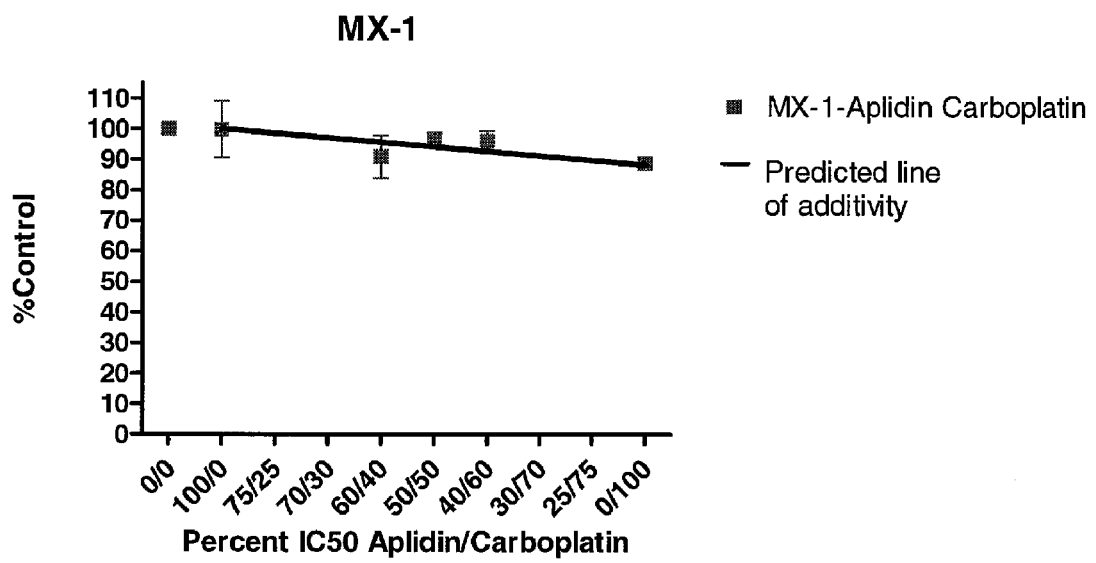
FIG. 37. In vitro activity data of Aplidine (Aplidin®) in combination with carboplatin against MX1 cells.
Figure 38:
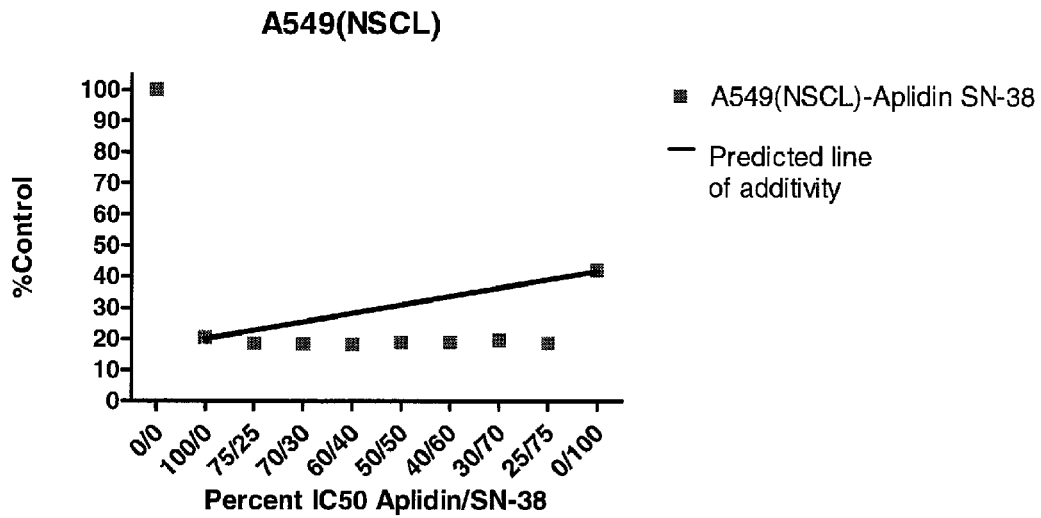
FIG. 38. In vitro activity data of Aplidine (Aplidin®) in combination with SN-38 against A549 cells.
Figure 39:
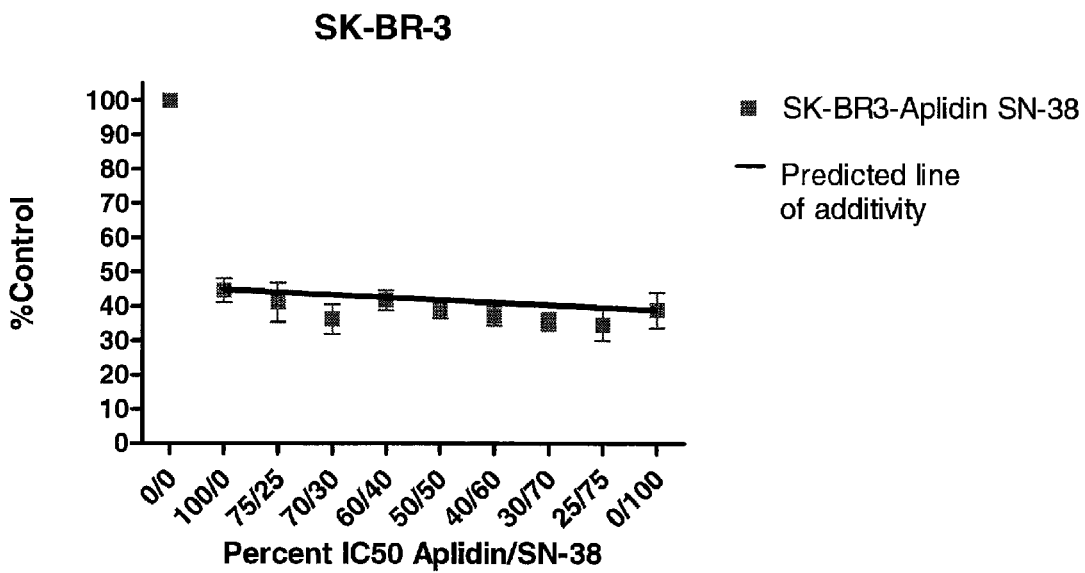
FIG. 39. In vitro activity data of Aplidine (Aplidin®) in combination with SN-38 against SKBR3 cells.
Figure 40:
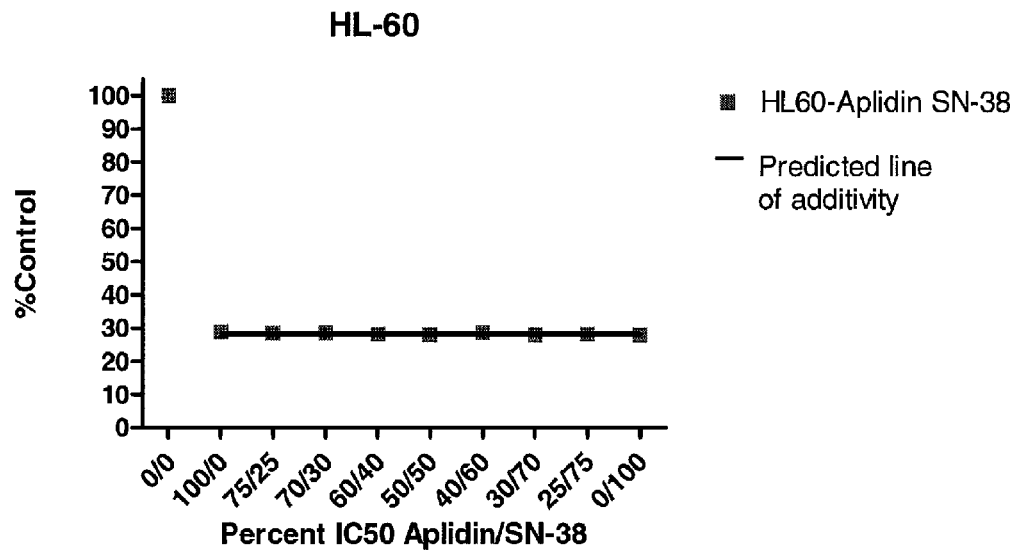
FIG. 40. In vitro activity data of Aplidine (Aplidin®) in combination with SN-38 against HL60 cells.
Figure 41:
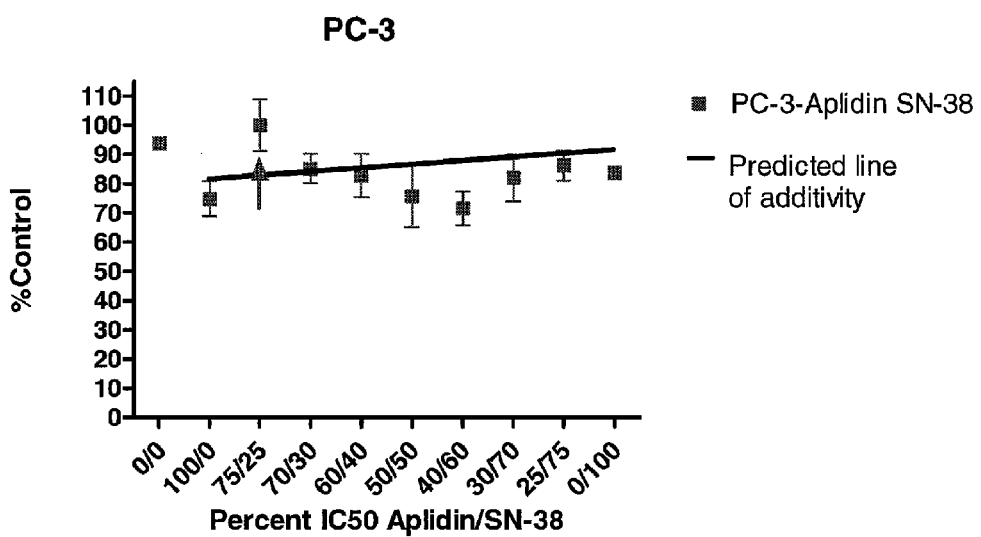
FIG. 41. In vitro activity data of Aplidine (Aplidin®) in combination with SN-38 against PC3 cells.

According to this assay it was found that:
a. The combination Aplidine with paclitaxel showed synergism in breast adenocarcinoma SKBR3 cells (FIG. 2), acute lymphoblastic leukaemia MOLT3 cells (FIG. 3) and prostate adenocarcinoma PC3 cells (FIG. 4). Trend to additivity was observed in promyelocytic leukemia HL60 cells (FIG. 5), breast carcinoma MX1 cells (FIG. 6) and NSCL A549 cells (FIG. 7).
b. The combination of Aplidine with doxorubicin showed synergism in NSCL A549 cells (FIG. 8), colon adenocarcinoma HT29 cells (FIG. 9) and prostate adenocarcinoma PC3 cells (FIG. 10). Additivity was observed in acute lymphoblastic leukaemia MOLT3 cells (FIG. 11), breast carcinoma MX1 cells (FIG. 12) and breast adenocarcinoma SKBR3 cells (FIG. 13).
c. The combination of Aplidine with cisplatin showed synergism in breast carcinoma MX1 cells (FIG. 14) and colon adenocarcinoma HT29 cells (FIG. 15). Additivity was observed in breast adenocarcinoma SKBR3 cells (FIG. 16) and acute lymphoblastic leukaemia MOLT3 cells (FIG. 17), and in NSCL A549 cells (FIG. 18) trends to synergism were found.
d. The combination of Aplidine with arsenic trioxide showed synergism in NSCL A549 cells (FIG. 19), colon adenocarcinoma HT29 cells (FIG. 20) and prostate adenocarcinoma PC3 cells (FIG. 21). Additivity was observed in acute lymphoblastic leukaemia MOLT3 cells (FIG. 22).
e. The combination of Aplidine with 5-fluorouracil showed synergism in promyelocytic leukemia HL60 cells (FIG. 23), breast adenocarcinoma SKBR3 cells (FIG. 24), NSCL A549 cells (FIG. 25) and prostate adenocarcinoma PC3 cells (FIG. 26). Additivity was observed in colon adenocarcinoma HT29 cells (FIG. 27).
f. The combination of Aplidine with cytosine arabinoside showed synergism in breast adenocarcinoma SKBR3 cells (FIG. 28), NSCL breast A549 cells (FIG. 29) and prostate adenocarcinoma PC3 cells (FIG. 30). Additivity was found in promyelocytic leukemia HL60 cells (FIG. 31) and colon adenocarcinoma HT29 cells (FIG. 32).
g. The combination of Aplidine with carboplatin showed synergism in prostate adenocarcinoma PC3 cells (FIG. 33) and colon adenocarcinoma HT29 cells (FIG. 34). Additivity was observed in NSCL A549 cells (FIG. 35), acute lymphoblastic leukaemia MOLT3 cells (FIG. 36) and breast carcinoma MX1 cells (FIG. 37).
h. The combination of Aplidine with SN38 showed synergism in NSCL A549 cells (FIG. 38). Additivity was observed in breast adenocarcinoma SKBR3 cells (FIG. 39), promyelocytic leukemia HL60 cells (FIG. 40) and prostate adenocarcinoma PC3 cells (FIG. 41).

Example 2

In vitro studies to determine the effect of Aplidine in combination with another standard agent on leukemia, lymphoma, multiple myeloma and melanoma tumor cell lines.

Following the same procedure as disclosed in example 1, Aplidine as a single agent or in combination with selected standard chemotherapeutic agents, was evaluated against several tumor cell lines to measure differences in cytotoxicity.

The following standard agents were selected as single agents and for combination with Aplidine: etoposide (VP16) and carboplatin. The tumor cell lines selected for this assay are shown in Table 3.

TABLE 3

| Cell Line | Tumor Type |
| --- | --- |
| HL-60 | Leukemia |
| K562 | Leukemia |
| MOLT-3 | Leukemia |
| H9 | Lymphoma |
| HUT78 | Lymphoma |
| MC116 | Lymphoma |
| RAMOS | Lymphoma |
| U937 | Lymphoma |
| NCI-H929 | Multiple Myeloma |
| HUNS-1 | Multiple Myeloma |
| U266B-1 | Multiple Myeloma |
| RPMI 8226 | Multiple Myeloma |
| LOXIMVI | Melanoma |
| UACC-257 | Melanoma |

Cell Culture Method

All cell lines were maintained in respective growth media at 37° C., 5% $CO_2$ and 98% humidity. All media formulations did not contain antibiotic. The day before plating cells all cultures were fed with fresh, complete growth media. On the harvest (plating) day cells were counted by Trypan Blue exclusion staining method.

Cell Plating

Cells were harvested and seeded in 96 well microtiter plates at 15,000 cells per well in 190 μl of media and incubated for 24 hours to allow the cells to attach before drug addition.

Drug Treatment

Stock solution of Aplidine was prepared in 100% DMSO at 5 mg/ml. Stock solutions of chemotherapeutic agents VP16 and carboplatin were prepared in 100% DMSO at the concentration 2 mg/ml for both drugs.

Cells were treated with Aplidine and the other standard agent at range as listed below, and individual drug concentration were made in triplicates per plate. The concentration of the tested agents used is expressed as a percent of the individual agent's $IC_{50}$, which were determined as in Example 1.

| $IC_{50}$ of Aplidine | $IC_{50}$ of Standard Agent |
| --- | --- |
| 100% | 0% |
| 75% | 25% |
| 60% | 40% |
| 50% | 50% |
| 40% | 60% |

| $IC_{50}$ of Aplidine | $IC_{50}$ of Standard Agent |
| --- | --- |
| 30% | 70% |
| 25% | 75% |
| 0% | 100% |

The individual $IC_{50}$ values of each agent for each cell line are shown in table 4.

TABLE 4

| Drug | Cell line | $IC_{50}$ (Molar) |
| --- | --- | --- |
| Aplidine | HL-60 | 8.0E−12 |
| | K562 | 2.0E−10 |
| | MOLT-3 | 3.2E−14 |
| | H9 | 4.8E−14 |
| | HUT78 | 10E−15 |
| | MC116 | 5.5E−10 |
| | RAMOS | 5.0E−09 |
| | U937 | 4.4E−13 |
| | U266B-1 | 5.9E−12 |
| | RPMI 8226 | 1.4E−14 |
| | HUNS-1 | 3.4E−14 |
| | NCI-H929 | 5.2E−13 |
| | LOXIMVI | 3.5E−09 |
| | UACC-257 | 4.8E−10 |
| VP16 | HL-60 | 2.0E−06 |
| | K562 | 7.6E−06 |
| | MOLT-3 | 2.4E−08 |
| | H9 | 7.3E−07 |
| | HUT78 | 1.4E−06 |
| | MC116 | 2.3E−07 |
| | RAMOS | 1.1E−07 |
| | U937 | 4.4E−07 |
| | U266B-1 | 5.9E−06 |
| | RPMI 8226 | 3.7E−07 |
| | HUNS-1 | 3.1E−06 |
| | NCI-H929 | 2.4E−06 |
| Carboplatin | LOXIMVI | 1.2E−04 |
| | UACC-257 | 1.7E−04 |

The cytotoxic effect was measured by the MTS Assay (Tetrazolium), which is a colorimetric method for determining the number of viable cells.

After 72 hours of incubation with tested agents 25 μl of MTS+PMS solution was added to each microtiter well and incubated for 4 hours at 37° C. Plates were then removed from incubator and placed on plate shaker for 5 minutes (covered with aluminum foil for protection from light). Optical densities were read at 490 nm on spectrophotometer plate reader. Data was analyzed as:
1. Prism (Graphpad) software program was used to normalized the data to control values (100%=cell growth in the absence of agent (drug); 0%=blank control).
2. Data normalized were plotted as scatter plots. A line was drawn connecting the values of 100% $IC_{50}$ for each agent (drug). Values significantly above the line indicated antagonism, below indicated synergy, and on the line indicated additivity.

Statistical treatment of data followed Laska E. et al. Biometrics (1994) 50:834-841 and Greco et al. Pharmacol Rev. (1995) 47: 331-385. Combinations at tested dose ratios were judged to be synergistic when inhibition of cell proliferation exceeded maximum inhibition values for each drug separately (at 100% $IC_{50}$). Conversely, antagonism was concluded when inhibition was lower than both maxima. Additivity was concluded when the effects of combinations did not differ significantly from the maxima for both drugs. Statistical significance was assessed by performing a student's t-test on the inhibition at each dose ratio versus the inhibition at the maximum for each drug. Overall significance of drug combinations for each cell line was dependent on showing statistical significance for greater than 50% of dose ratios.

As a visual aid, response values were plotted on a scatter plot with dose ratios given on the x-axis and % response values on the y-axis. A horizontal line was drawn between the two endpoint response values (E.g. Between the response values for 100% $IC_{50}$ Aplidine and 100% $IC_{50}$ standard chemotherapeutic agent). In cases where response values at the two endpoints were approximately equivalent, points lying above or below this predicted line of additivity could be interpreted as representing antagonistic or synergistic drug interaction respectively.

Figure 42A:
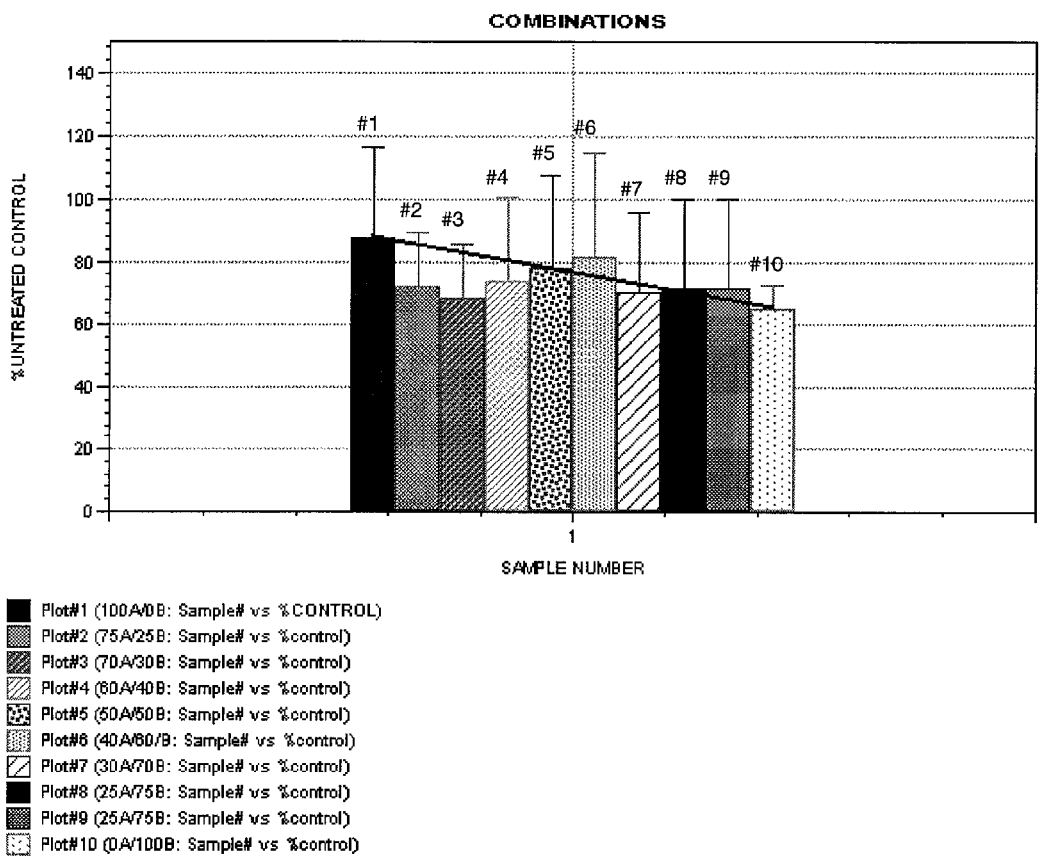
FIGS. 42A and 42B. In vitro activity data of Aplidine (A, Aplidin®) in combination with VP16 (B) against HL-60 cells.
Figure 42B:
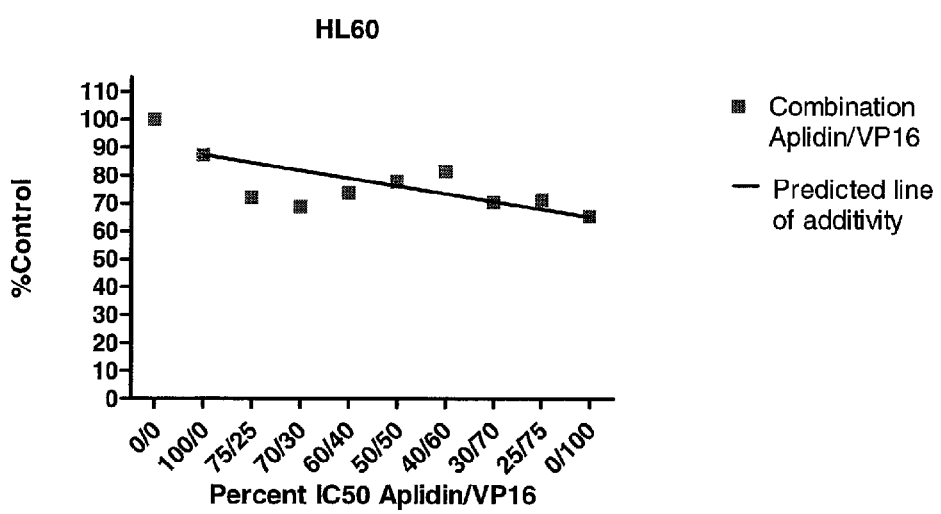

In FIGS. 42A and 42B it is shown the in vitro activity data of Aplidine in combination with VP16 against HL-60 cells. According to this data additive effect is obtained.

Figure 43A:
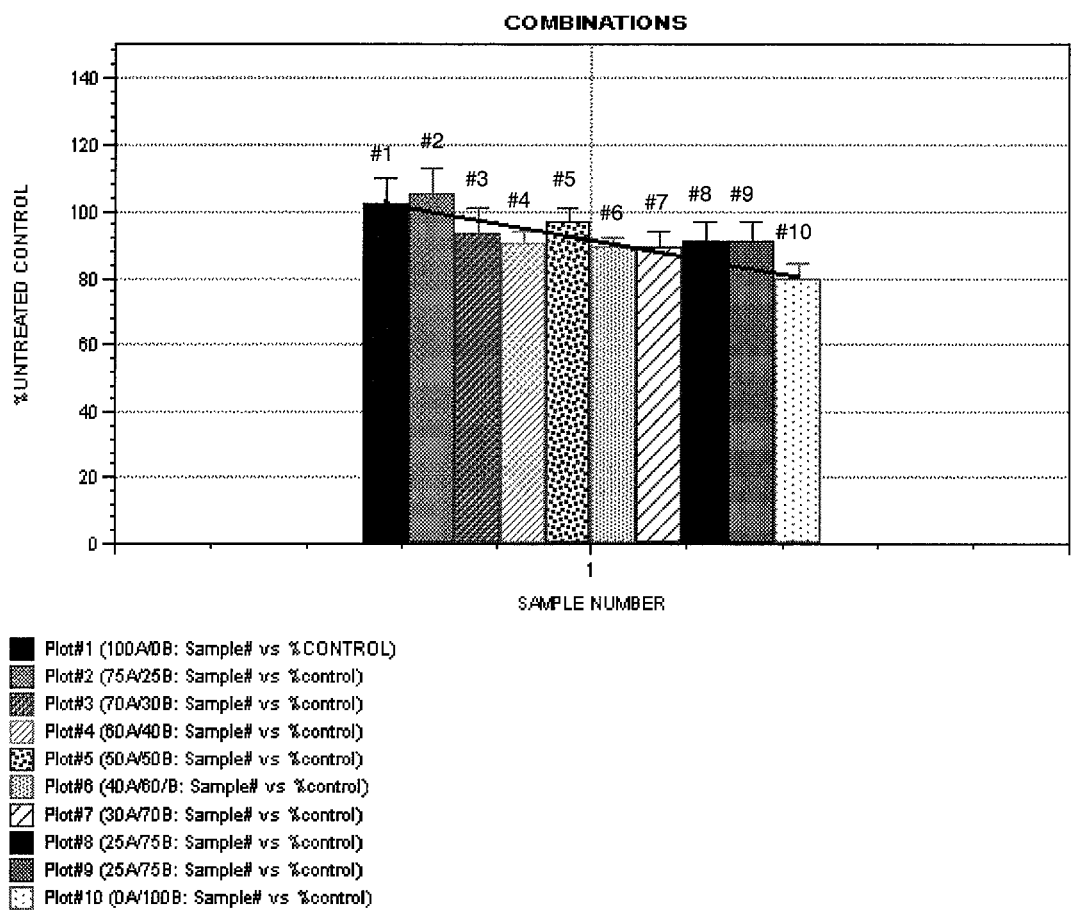
FIGS. 43A and 43B. In vitro activity data of Aplidine (A, Aplidin®) in combination with VP16 (B) against K562 cells.
Figure 43B:
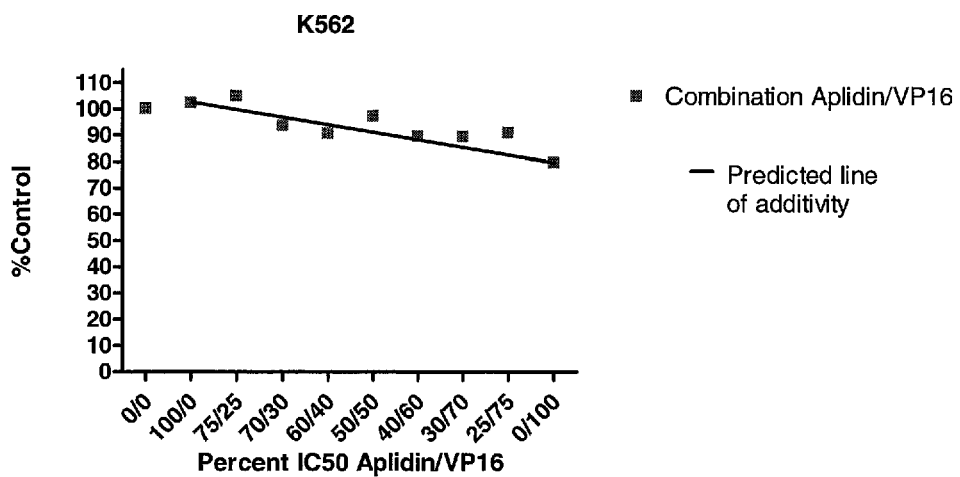

In FIGS. 43A and 43B it is shown the in vitro activity data of Aplidine in combination with VP16 against K562 cells. According to this data additivity is obtained.

Figure 44A:
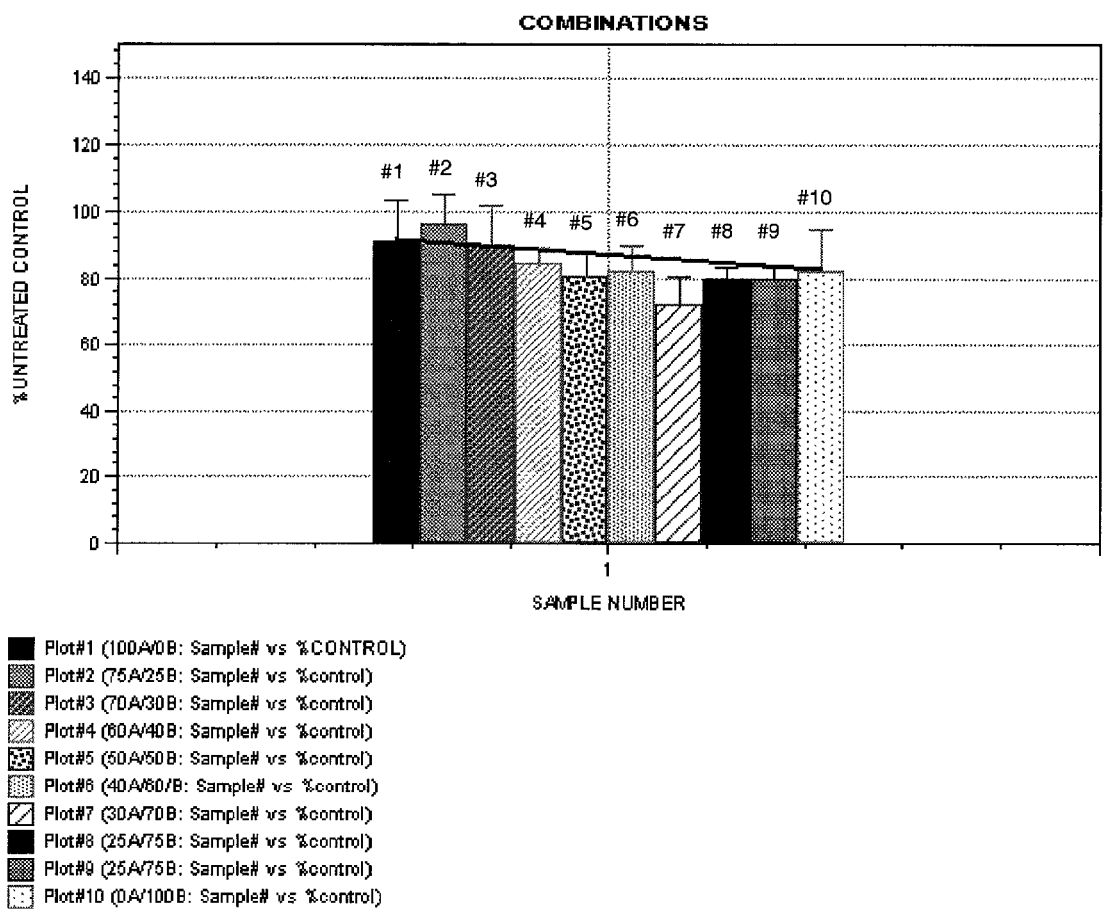
FIGS. 44A and 44B. In vitro activity data of Aplidine (A, Aplidin®) in combination with VP16 (B) against MOLT-3 cells.
Figure 44B:
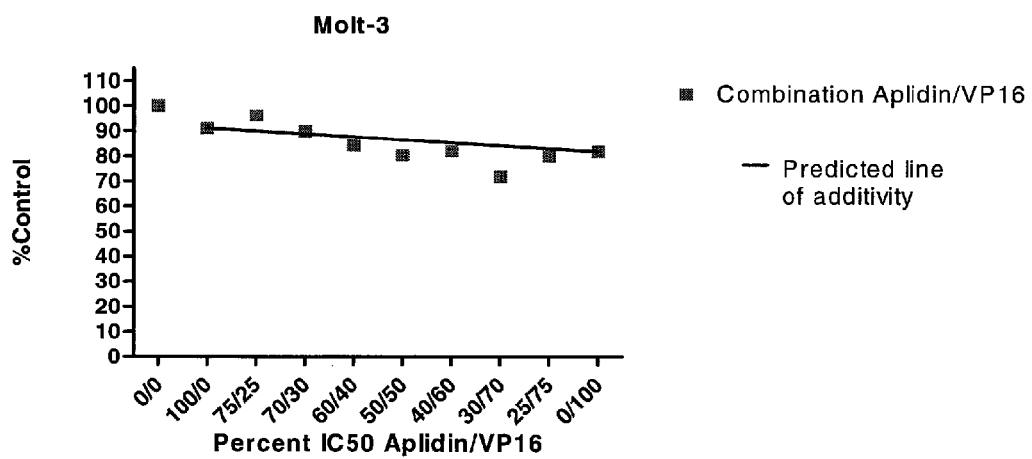

In FIGS. 44A and 44B it is shown the in vitro activity data of Aplidine in combination with VP16 against MOLT-3 cells. According to this data additivity is obtained.

Figure 45A:
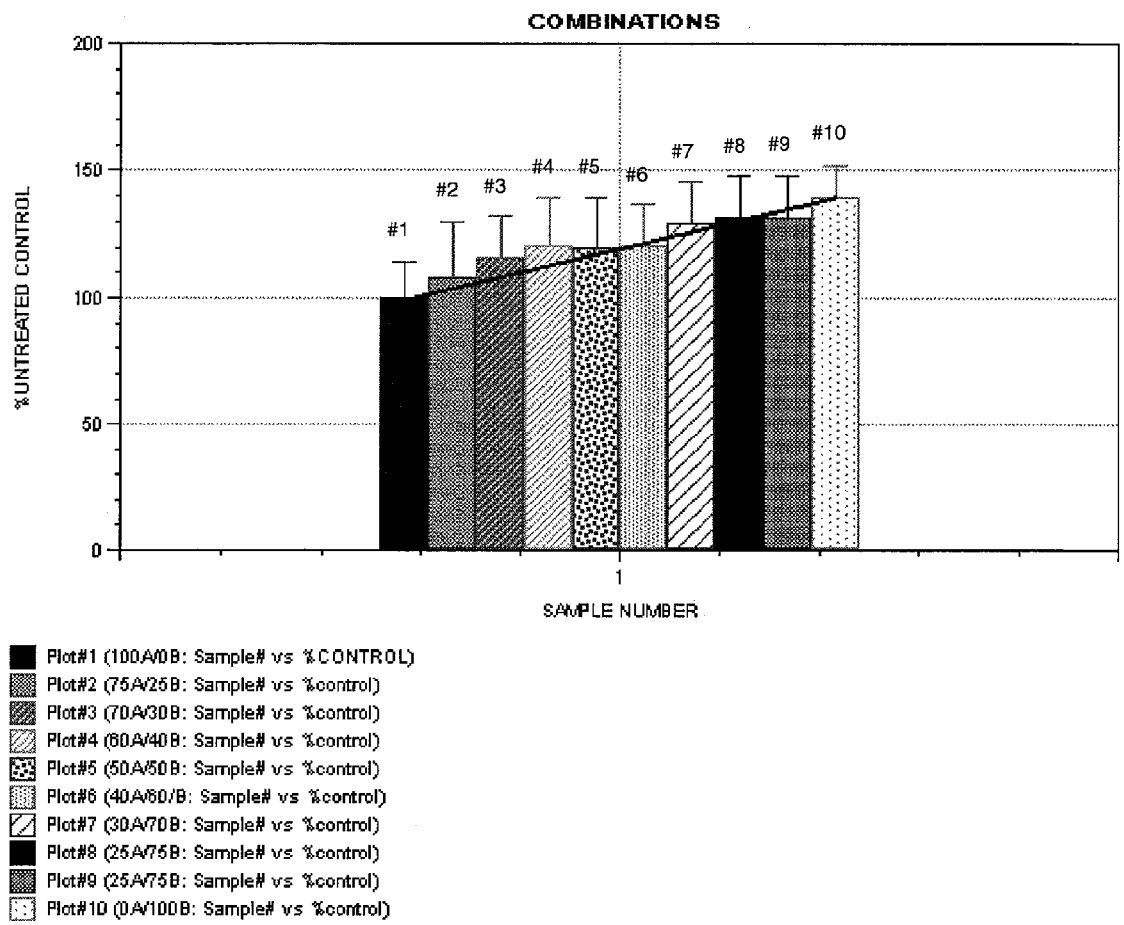
FIGS. 45A and 45B. In vitro activity data of Aplidine (A, Aplidin®) in combination with VP16 (B) against MC116 cells.
Figure 45B:
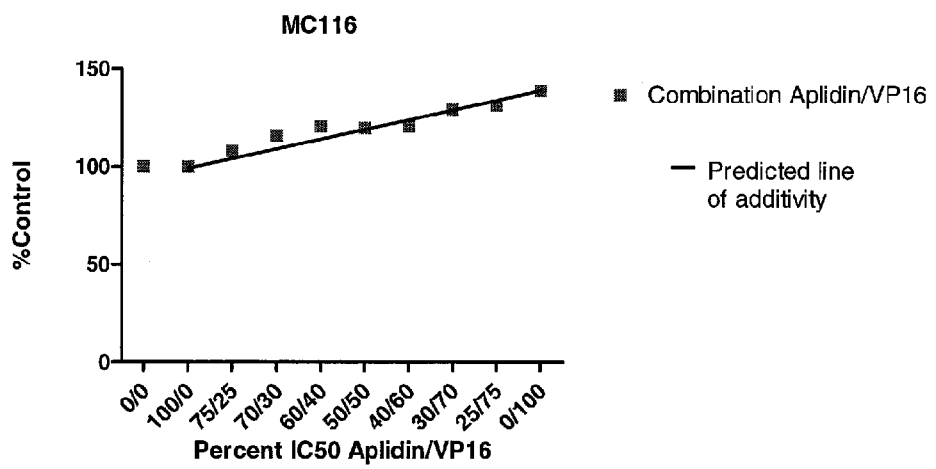

In FIGS. 45A and 45B it is shown the in vitro activity data observed with Aplidine in combination with VP16 against MC116 cells. According to this data additivity is obtained in this tumor cell line.

Figure 46A:
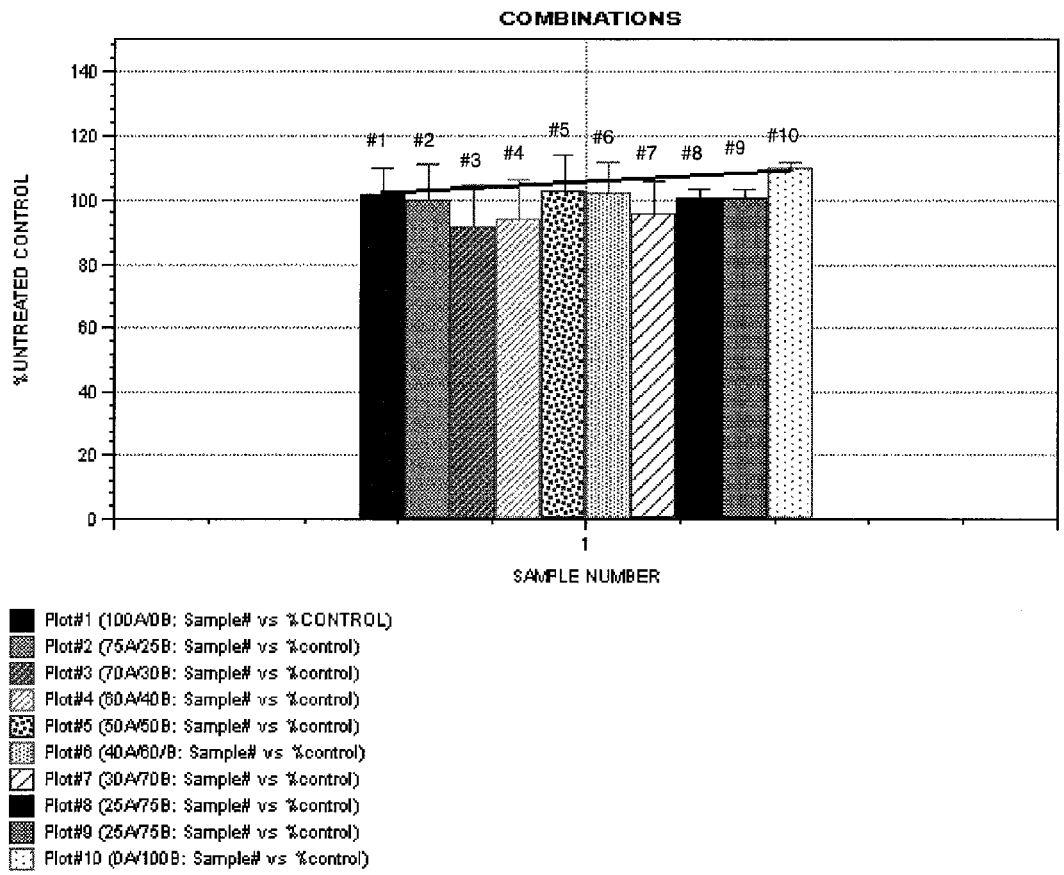
FIGS. 46A and 46B. In vitro activity data of Aplidine (A, Aplidin®) in combination with VP16 (B) against RAMOS cells.
Figure 46B:
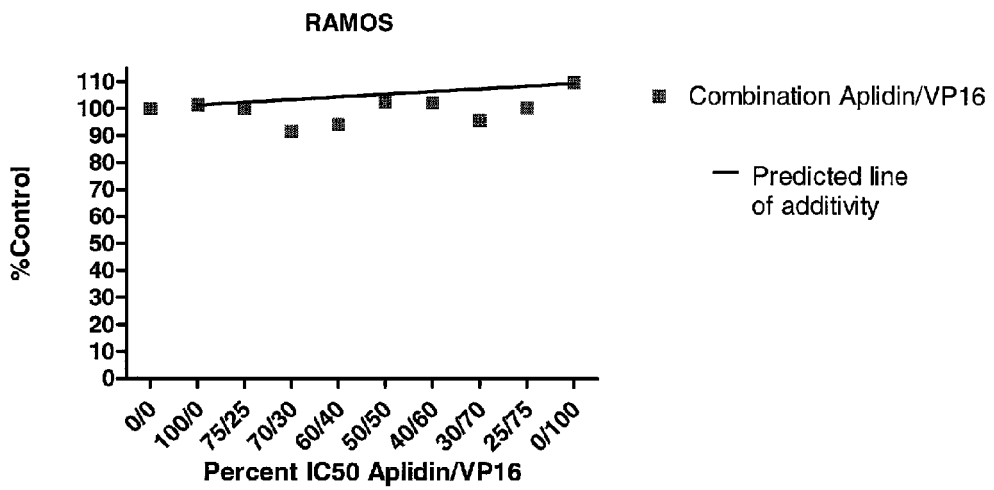

In FIGS. 46A and 46B it is shown the in vitro activity data observed with Aplidine in combination with VP16 against RAMOS cells. According to this data synergism is obtained in this tumor cell line.

Figure 47A:
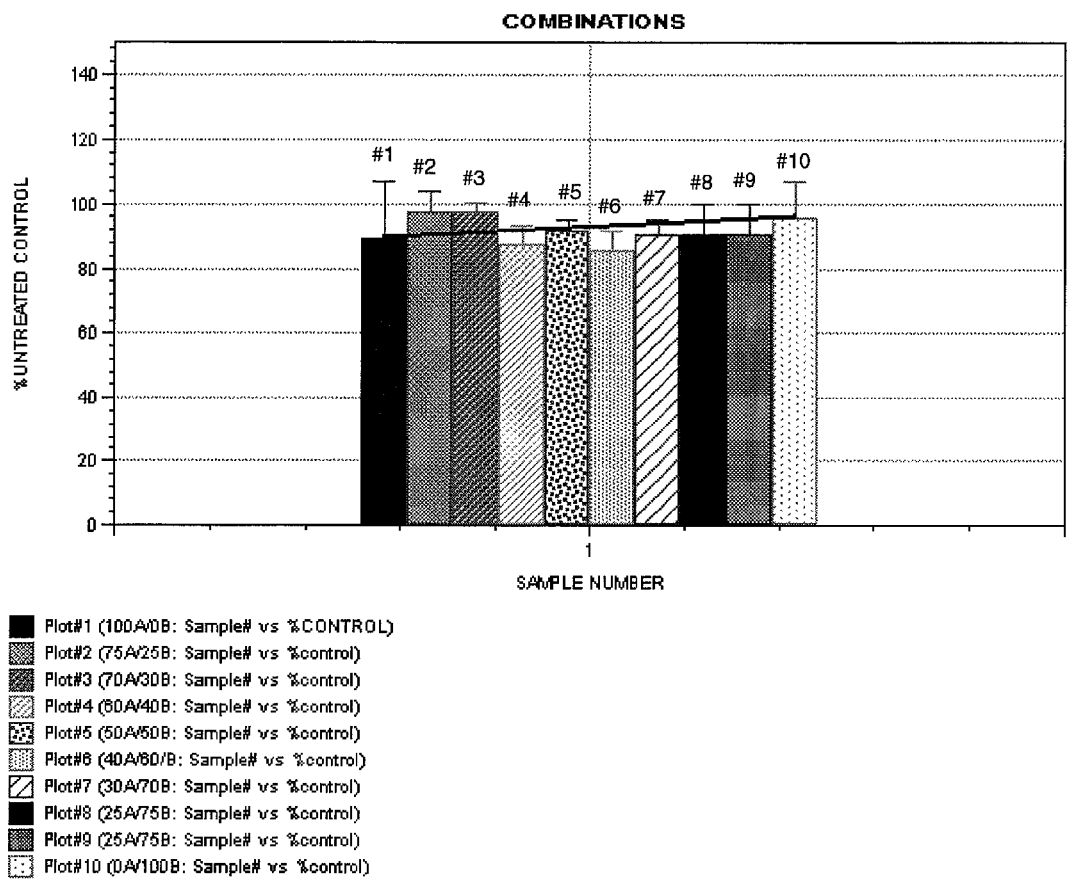
FIGS. 47A and 47B. In vitro activity data of Aplidine (A, Aplidin®) in combination with VP16 (B) against U937 cells.
Figure 47B:
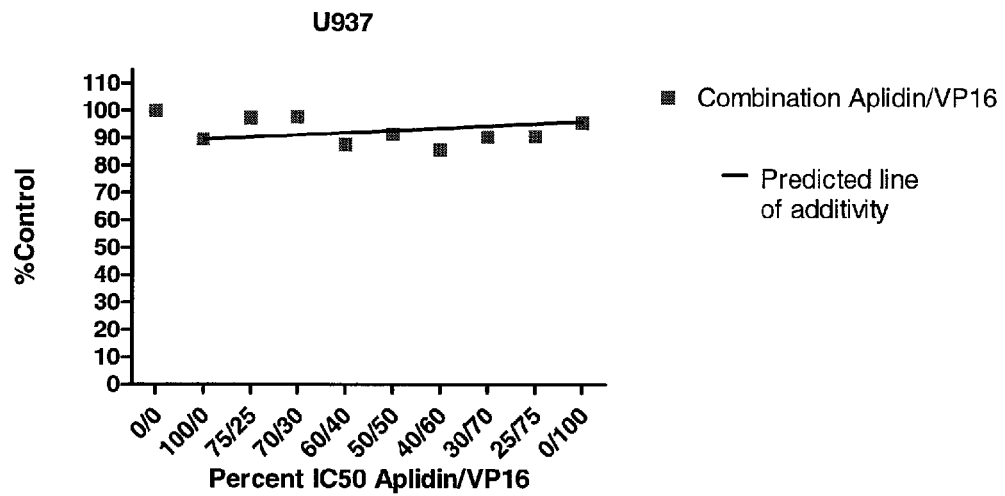

In FIGS. 47A and 47B it is shown the in vitro activity data observed with Aplidine in combination with VP16 against U937 cells. According to this data additivity is obtained.

Figure 48A:
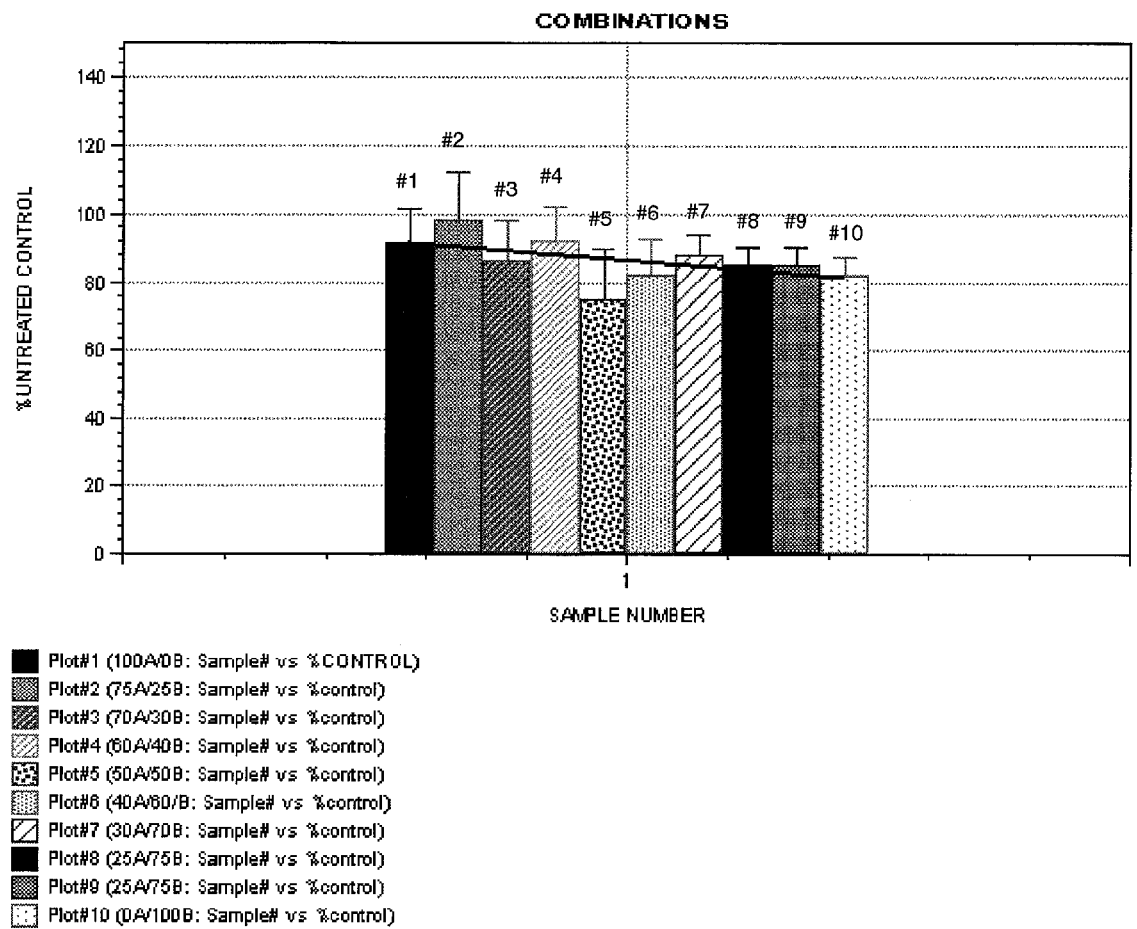
FIGS. 48A and 48B. In vitro activity data of Aplidine (A, Aplidin®) in combination with VP16 (B) against NCI-H929 cells.
Figure 48B:
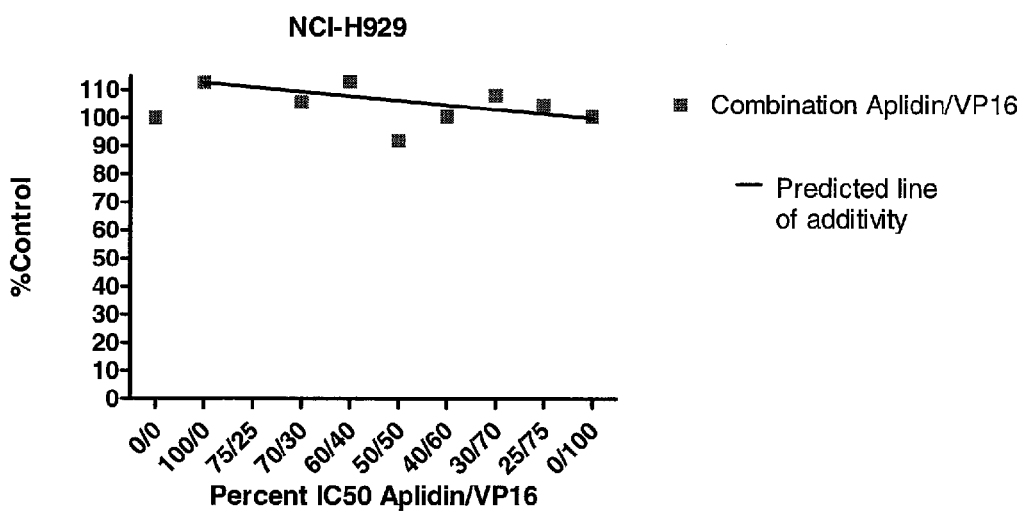

In FIGS. 48A and 48B it is shown the in vitro activity data observed with Aplidine in combination with VP16 against NCI-H929 cells. According to this data synergism is obtained.

Figure 49A:
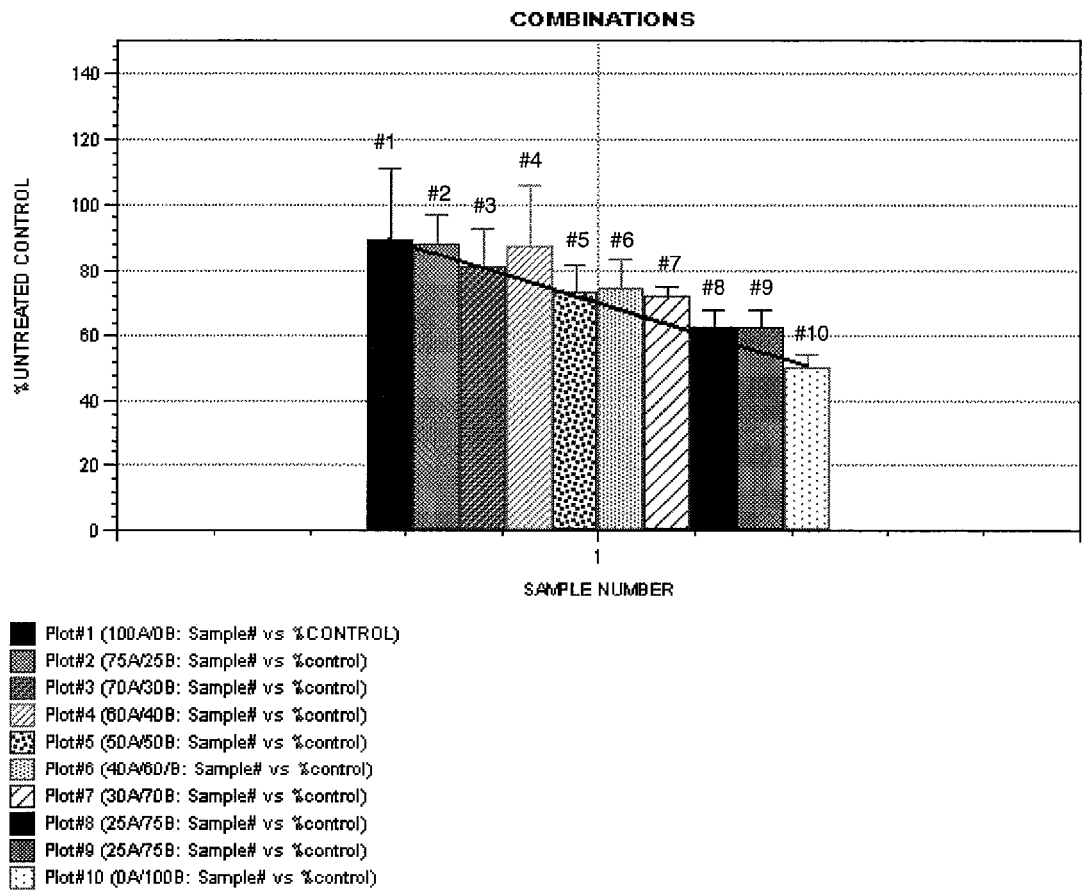
FIGS. 49A and 49B. In vitro activity data of Aplidine (A, Aplidin®) in combination with VP16 (B) against HUNS-1 cells.
Figure 49B:
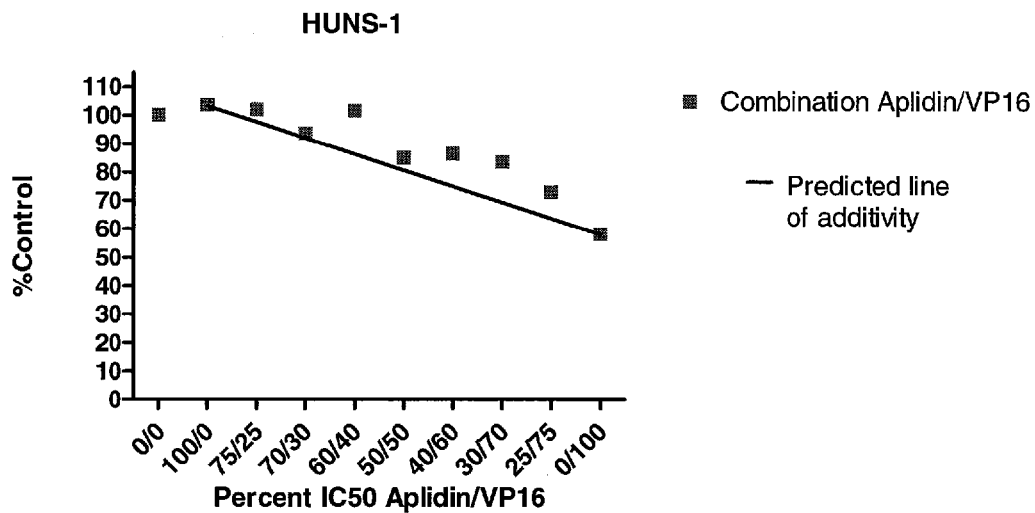

In FIGS. 49A and 49B it is shown the in vitro activity data observed with Aplidine in combination with VP16 against HUNS-1 cells. According to this data additivity is obtained in this tumor cell line.

Figure 50A:
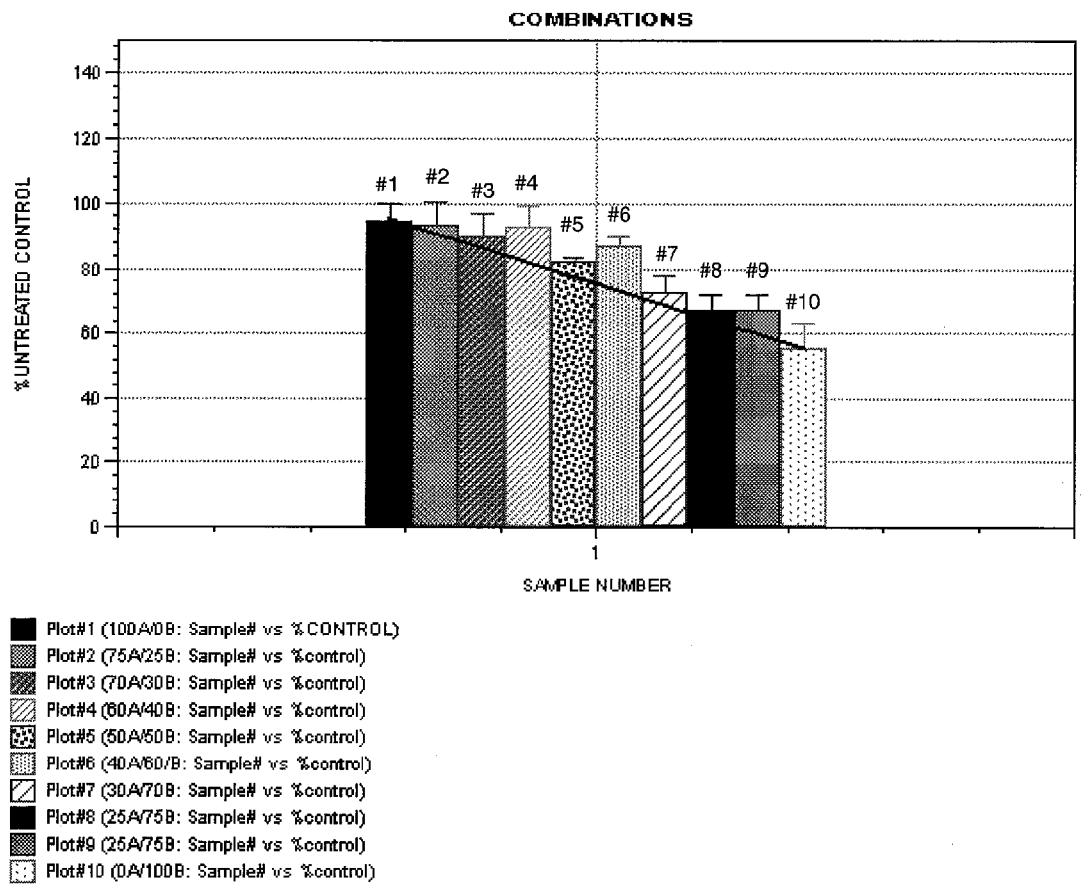
FIGS. 50A and 50B. In vitro activity data of Aplidine (A, Aplidin®) in combination with VP16 (B) against U266 B1 cells.
Figure 50B:
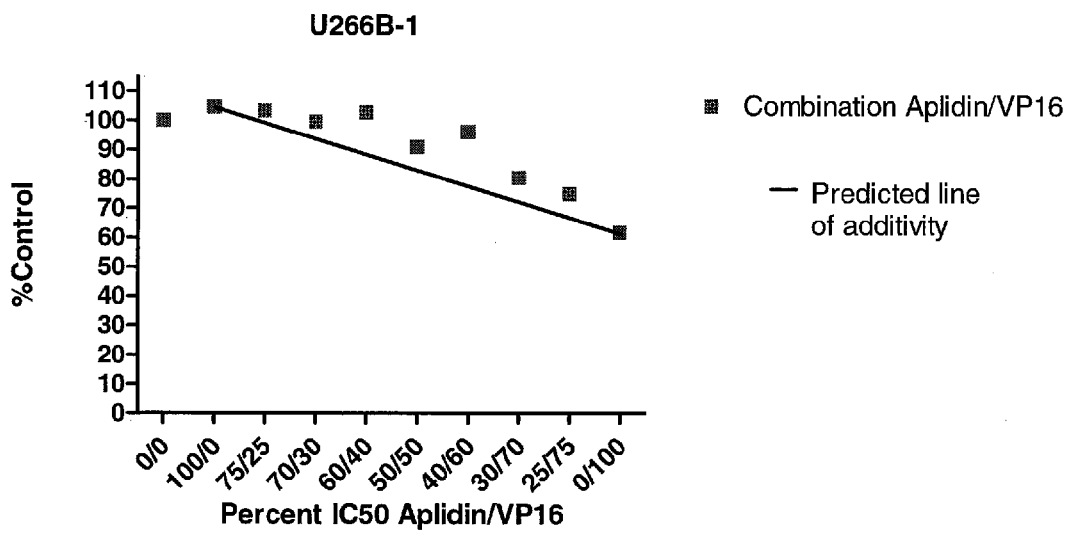

In FIGS. 50A and 50B it is shown the in vitro activity data observed with Aplidine in combination with VP16 against U266B-1 cells. According to this data additivity is obtained in this tumor cell line.

Figure 51A:
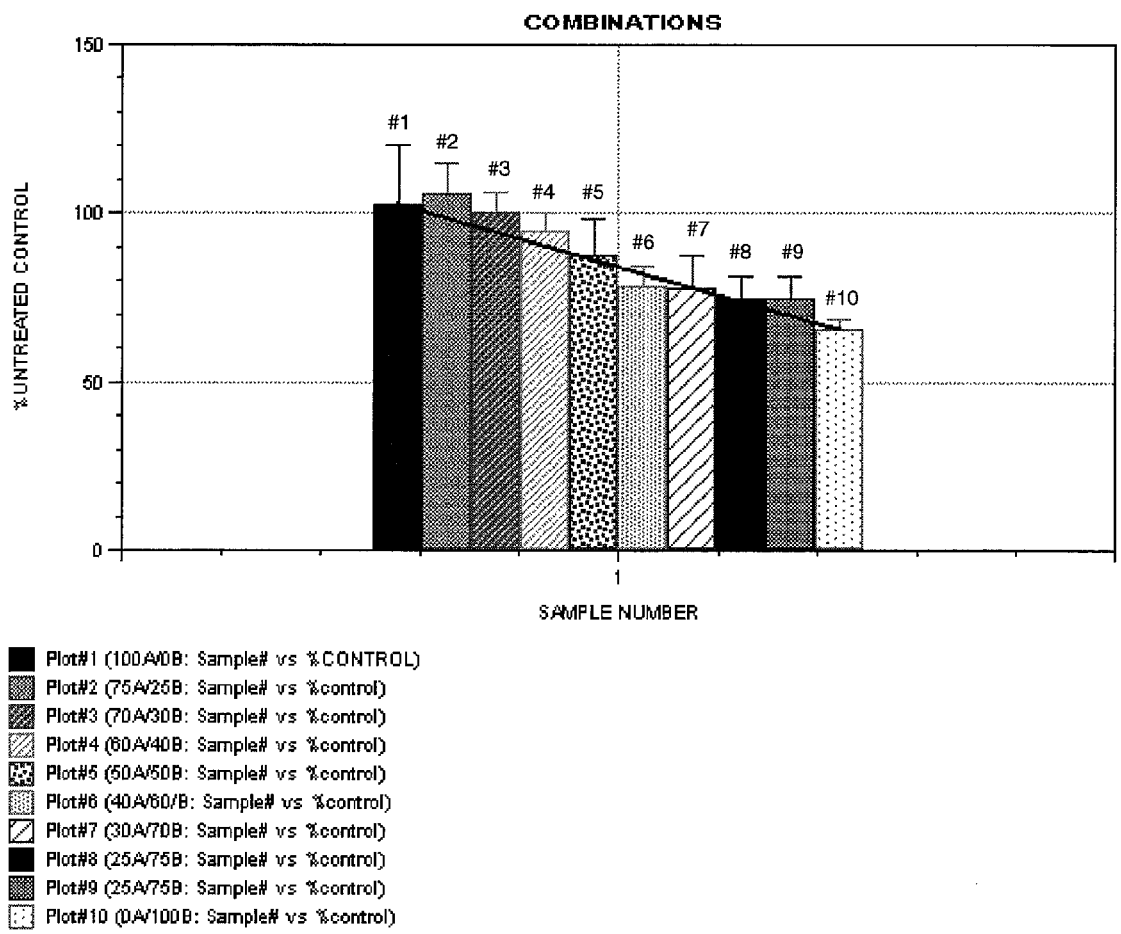
FIGS. 51A and 51B. In vitro activity data of Aplidine (A, Aplidin®) in combination with VP16 (B) against RPMI 8226 cells.
Figure 51B:
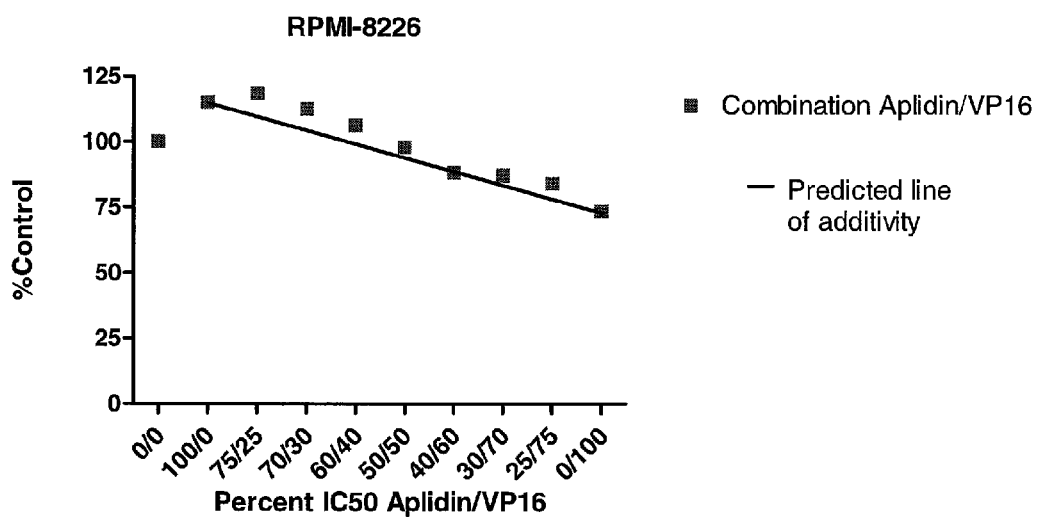

In FIGS. 51A and 51B it is shown the in vitro activity data observed with Aplidine in combination with VP16 against RPMI 8226 cells. According to this data additivity is obtained in this tumor cell line.

Figure 52:
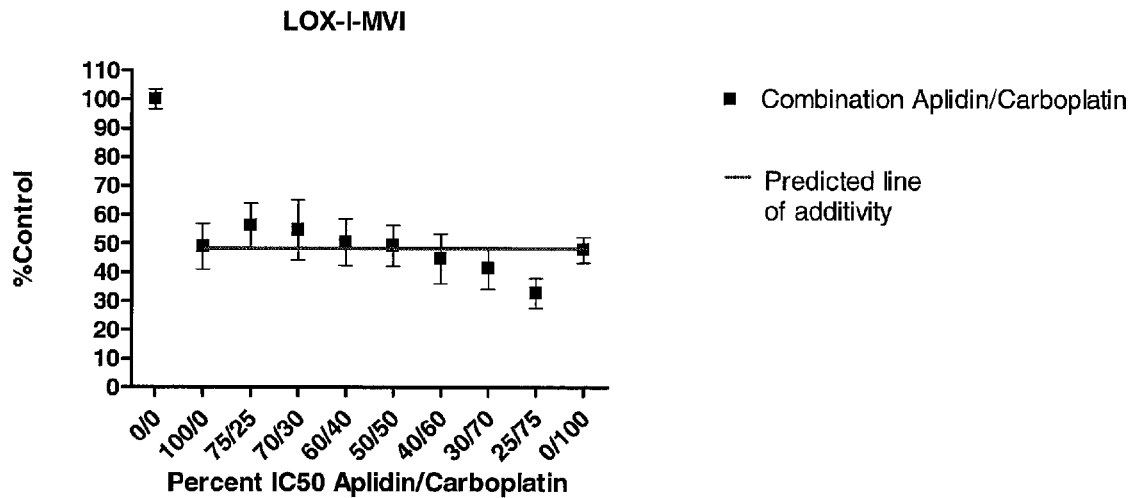
FIG. 52. In vitro activity data of Aplidine (Aplidin®) in combination with carboplatin against LOX-I-MVI cells.

In FIG. 52 it is shown the in vitro activity data observed with Aplidine in combination with carboplatin against LOX-I-MVI cells. According to this data additivity is obtained in this tumor cell line.

Figure 53:
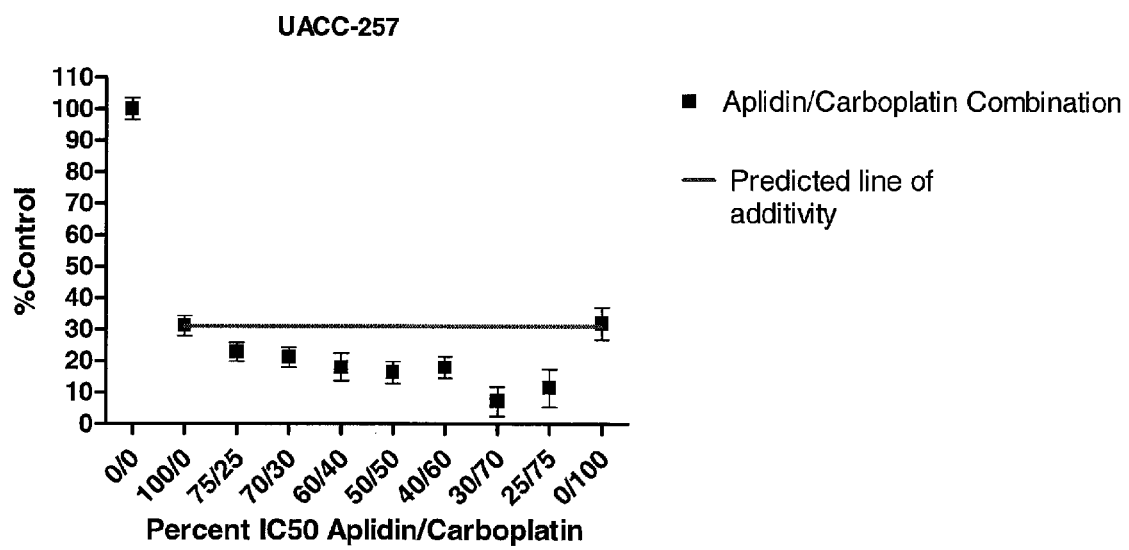
FIG. 53. In vitro activity data of Aplidine (Aplidin®) in combination with carboplatin against UACC-257 cells.

In FIG. 53 it is shown the in vitro activity data observed with Aplidine in combination with carboplatin against UACC-257 cells. According to this data synergism is obtained in this tumor cell line.

Example 3

In vitro studies to determine the effect of Aplidine in combination with other standard agents on multiple myeloma tumor cell lines.

Multiple myeloma (MM) is a malignant disease of plasma cells, generally originated from a clone of plasma cells which proliferate and accumulate in the bone marrow. Clinicopathological features of patients with myeloma include accumulation of monoclonal protein in the blood or urine, lytic bone lesions, anaemia and renal dysfunction (Sirohi B. et al. Lancet (2004) 363: 875-87).

Actual treatment for myeloma relies on high dose therapy supported by stem cell transplantation. Despite the advances in the last decade, nowadays MM remains an incurable disease with a median overall survival for patients of 2 to 5 years (Sirohi B. et al. Lancet (2004) 363: 875-87). New treatment approaches are needed to improve patients outcome following three major lines of investigation: a) enhancing the efficacy of chemotherapy through the use of high dose; b) enhancing the host immune response against myeloma cells; and c) developing novel drugs with more specific targets that may interfere not only with myeloma cells but also the bone marrow microenvironment (San Miguel J F et al. Curr. Treat. Options Oncol. (2003) 4: 247-58). Hopefully, the combination of two or more of these therapeutic agents will lead to an improved anti-MM efficacy and longer survival rates.

Herewith we report several studies on the effect of Aplidine as a new drug in the treatment of multiple myeloma. These studies include:
1) cytotoxic efficacy of Aplidine (alone or in combination) on several MM cell lines using cell viability (MTT assay) and apoptosis (annexin V staining) assays.
2) cytotoxic efficacy of combinations of Aplidine and other classical and recently developed drugs in the treatment of this disease.

Material and Methods
Cell Lines and Cell Culture Reagents

Four MM-derived cell lines were used in this study: the dexamethasone-sensitive (MM.1 S) and dexamethasone-resistant (MM.1R) variants of the human multiple myeloma cell line MM.1 (Greenstein S. et al. Exp. Hematol (2003) 31:271-82) which were kindly provided by Dr. S Rudikoff, Bethesda Md.; and the U266 and its melphalan-resistant counterpart U266 LR7 cell lines were obtained from Dr. W. Dalton, Tampa, Fla. All MM cell lines were grown in RPMI 1640 medium supplemented with 10% heat-inactivated fetal bovine serum, 100 U/ml penicillin, 100 μg/ml streptomycin and 2 mM L-glutamine. All cell culture media and reagents were purchased from Invitrogen Corporation (Carlsbad, Calif.).

Cell Viability Assays

The analysis of MM cell proliferation was assessed using the methylthiotetrazole (MTT; Sigma, St. Louis Mo.) colorimetric assay. MM cell lines were seeded at a density of 50000 cells/200 μl medium per well in 48-well plates, and treated with a determined drug dose and time. Two hours before the end of the treatment, a MTT solution (5 mg/ml in PBS; usually a 10% of the volume in each well) was added and the tetrazolium salt was reduced by metabolically active cells to coloured formazan crystals. After solubilization of these crystals by overnight incubation with 10% SDS-HCl solution, absorbance was measured at 570 nm with correction at 630 nm. Four wells were analyzed for each condition, and the results are presented as the mean±SD of quadruplicates of a representative experiment that was repeated at least three times.

Western Blot

Cells were collected and washed with PBS, and total cell lysates were obtained after incubation in ice-cold lysis buffer (140 mM NaCl, 10 mM EDTA, 10% glycerol, 1% Nonidet P-40, 20 mM Tris (pH 7.0), 1 μM pepstatin, 1 μg/ml aprotinin, 1 μg/ml leupeptin, 1 mM sodium orthovanadate). Samples were then centrifuged at 10,000 g at 4° C. for 10 min and equal amounts of protein in supernatants were resolved by 6%-12.5% SDS-PAGE. Proteins were then transferred onto nitrocellulose or PVDF membranes, blocked by incubation in 5% defatted dry milk in PBST buffer (0.05%-Tween 20 in PBS) and subsequently incubated with the specific primary antCruz Technologies, ibody [the anti-p-c-jun, anti-p-Erk1/2 and anti-Erk5 antibodies were purchased from Santa Cruz Biotechnologies (Santa Cruz, Calif.), whereas the anti-p-p38 was obtained from Cell Signaling (Danvers, Mass.) and the anti-PARP antibody from Becton Dickinson Biosciences (Bedford, Mass.)]. After a second incubation with the correspondent secondary antibody immunoblots were developed by enhanced chemilunescence (ECL; Amersham, Arlington Heights, Ill.). Identification of activated JNK and Erk5 required previous immunoprecipitation of protein lysates with the correspondent specific antibodies and protein A sepharose.

Isobologram Analysis

The interaction between Aplidine and other anti-MM agents was analyzed using the Calcusyn software program (Biosoft, Ferguson, Mo.). Data from cell viability assay (MTT) were expressed as the fraction of cells affected by the dose (Fa) in drug treated cells as compared to untreated cells (control). This program is based upon the Chou-Talalay method (Chou T C et al. Adv. Enzyme Regul. (1984) 22: 27-55) according to the following equation $CI=(D)1/(Dx)1+(D)1(D)2/(Dx)1(Dx)_2$ where (D)1 and (D)2 are the doses of drug 1 and 2 that have the same x effect when used alone. CI values less than 1.0 indicate synergism, CI values≅1.0 indicate an additive effect, whereas values more than 1 correspond to antagonistic effect.

Results

Dose Response to Aplidine in MM-Derived Cell Lines

Figure 54:
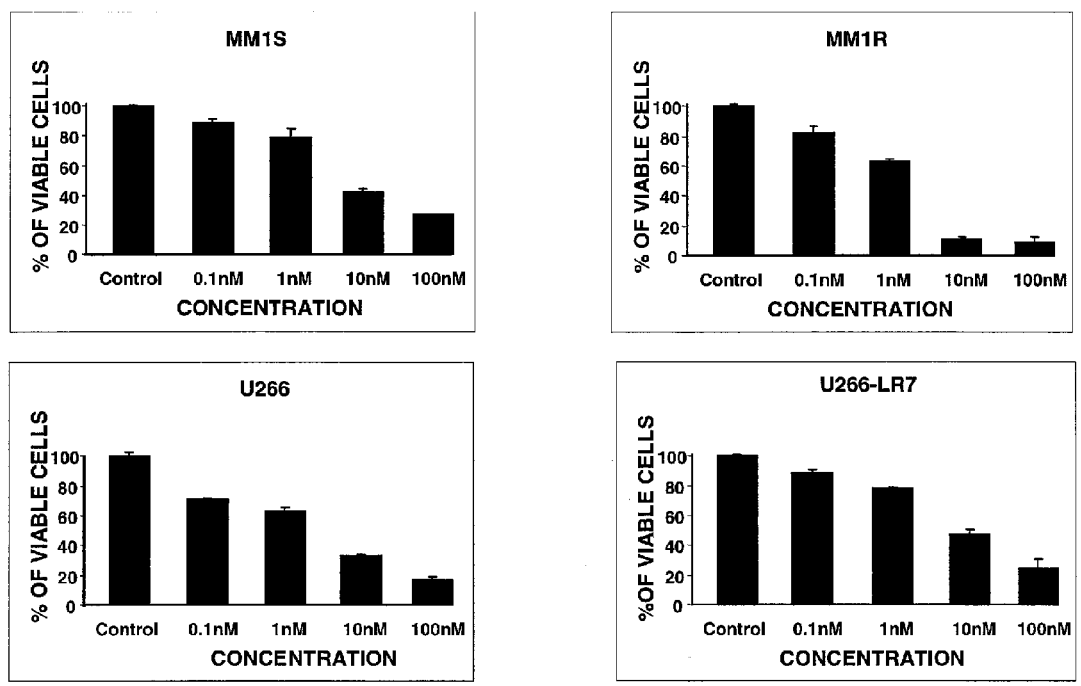
FIG. 54. Dose response to Aplidine after (48 h treatment) in MM1S, MM1R, U266 and U266-LR7 cell lines.

We first determined whether Aplidine affects cell viability using the MTT assay on MM-derived cell lines both sensitive and resistant to conventional therapy drugs. As seen in FIG. 54, Aplidine treatment for 48 h induces a similar decrease in cell viability in a dose-dependent manner in all cell lines tested. Fifty percent decrease in viable cells ($IC_{50}$) after 48 h treatment was within the 1-10 nM range for the four cell lines tested.

Figure 55:
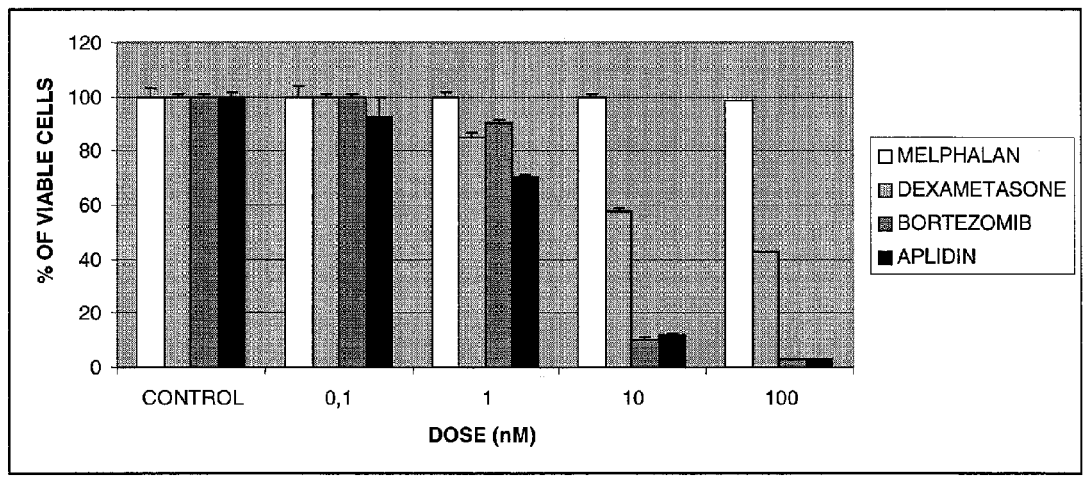
FIG. 55. Comparison of dose efficacy of Aplidine (Aplidin®) and other drugs on the MM1S cell line (48 h of treatment).

Efficacy of Aplidine was also compared to other classic (Melphalan, Dexamethasone) and new drugs (Bortezomib) in the treatment of MM. FIG. 55 shows superior potency of Aplidine as compared to the other drugs when tested at 0.1-1 nM doses for 48 h on the MM.1S cell line; its effect was similar to that of Bortexomib at maximal doses (10-100 nM).

Evaluation of Synergism in Double Combinations of Aplidine

Since continuous exposure to MM chemotherapy is in many cases associated to increased toxicity and development of the novo drug resistance, we tested whether the combination of minimally toxic concentrations of Aplidine and other drugs would affect MM cell viability. Specifically, Aplidine was combined with classic drugs in the treatment of MM (such as Dexamethasone or Melphalan), also with recently developed anti-myeloma agents (Bortezomib), and with drugs that would specifically target the bone-marrow microenvironment (lenalidomide (Revlimid®)).

Time course experiments at days 1, 2, 3 and 6 were also performed for the mentioned therapeutic agents to determine the appropriate suboptimal doses (10% to 30% growth inhibition) for combinatorial experiments as well as to explore for the duration of the treatments. Combination experiments of Aplidine and the rest of the drugs were performed after incubation for 3 days or 6 days. Cell growth of MM.1S cell line was measured by MTT assay as described above, and the percentages of inhibition were analyzed by the CalcuSyn Program. The computer-calculated combination index (CI) was used to judge the outcomes of a combination: CI>1, CI=1, and CI<1 indicating antagonism, additive, and synergistic effects, respectively. The conformity of data to the median-effect principle can be readily manifested by the linear correlation coefficient (r) of the median-effect plot: log (fa/fu)=m log(D)−m log(Dm), wherein D is the dose, Dm is the dose required for a 50% effect, fa is the fraction affected by dose, fu is the unaffected fraction, and m is a coefficient of the sigmoidicity of the dose-effect curve. For each double combination a non-constant ratio combination was utilized. Each experiment was repeated three times, and a minimum of three data points for each single drug and three combinations were performed.

Combination of Aplidine with Dexamethasone

Figure 56:
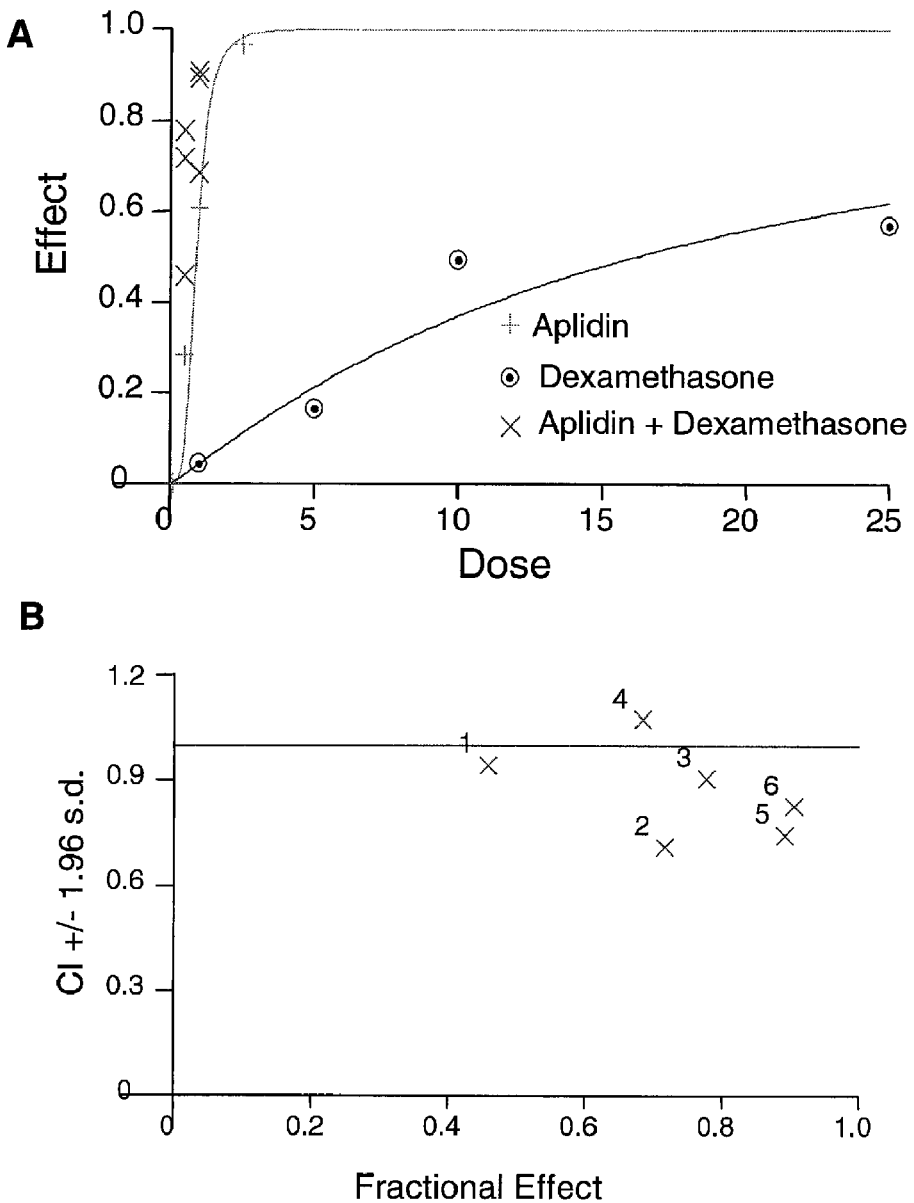
FIG. 56. Combination Aplidine (Aplidin®) and Dexamethasone at 3 days. A) Dose effect curve. B) Fa-CI plot.

At day 3, a synergism was observed for 0.5 nM Aplidine/1 nM and 10 nM Dexamethasone combinations (FIG. 56).

Figure 57:
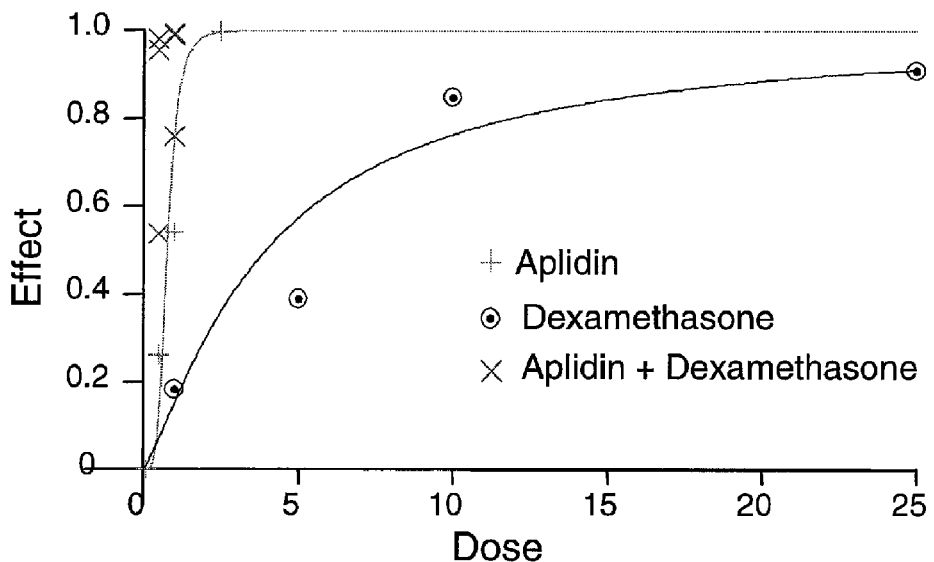
FIG. 57. Combination Aplidine (Aplidin®) and Dexamethasone at 6 days. A) Dose effect curve. B) Fa-CI plot.
Figure 57:
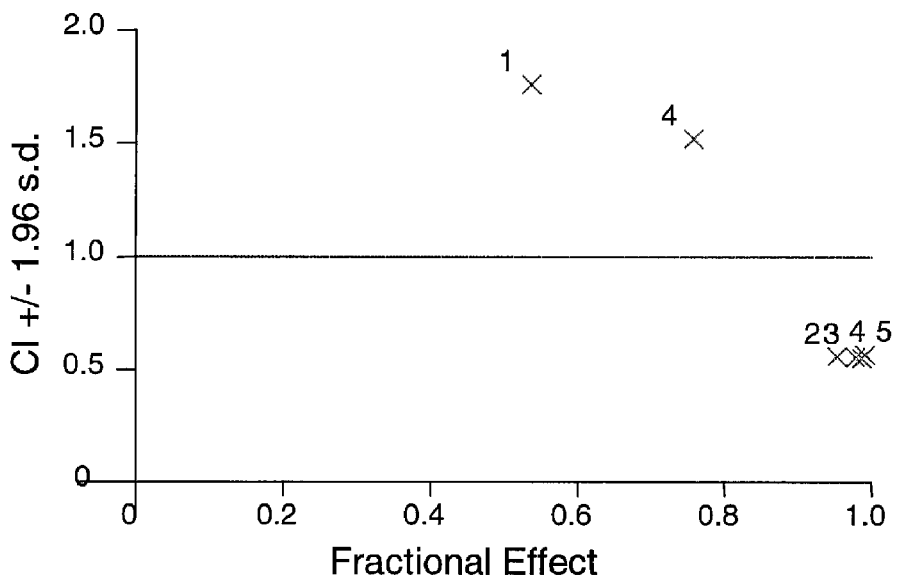

As illustrated in FIG. 57, the combination was more synergistic at 6 days.

Combination of Aplidine with Melphalan

Figure 58:
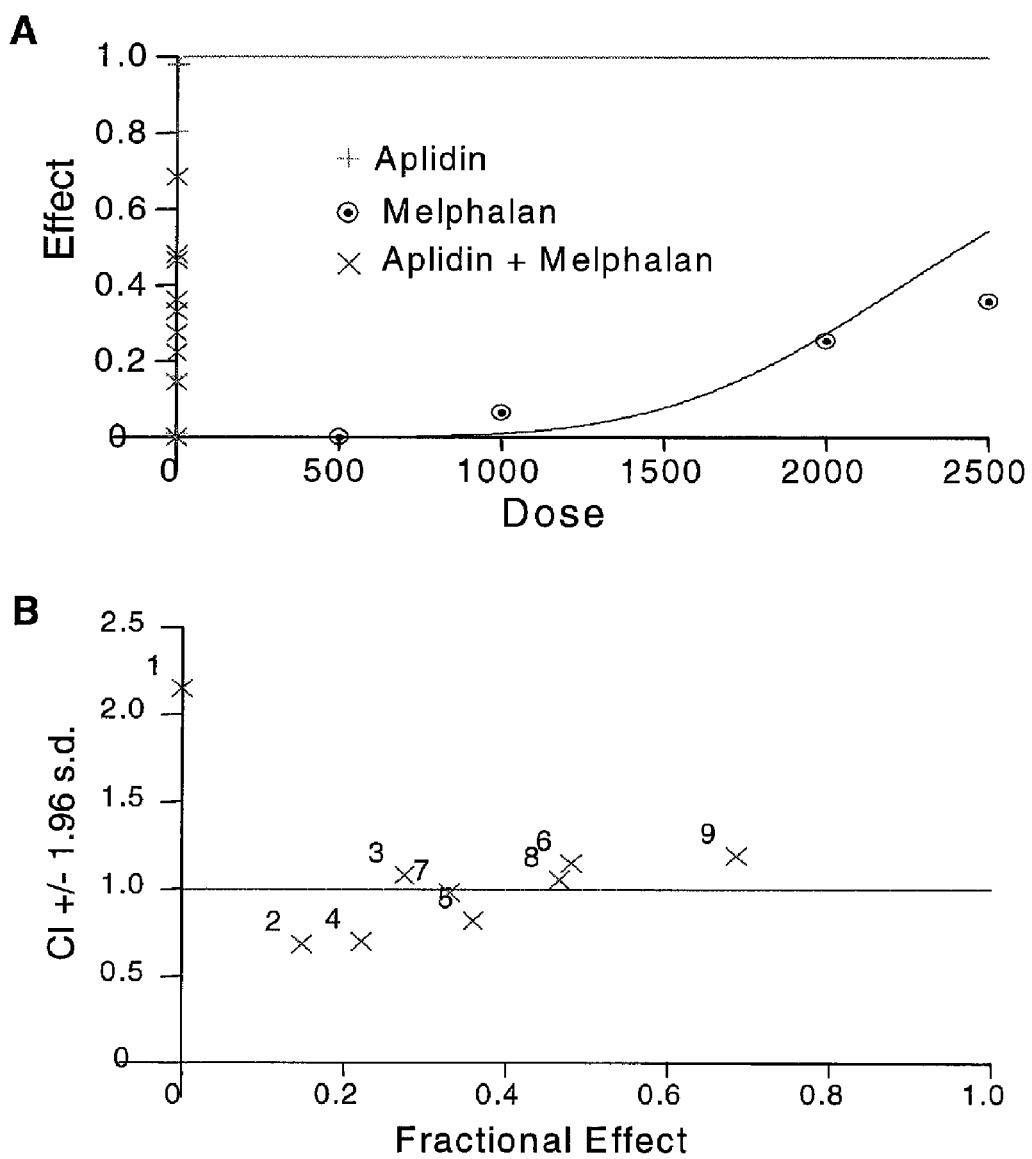
FIG. 58. Combination Aplidine (Aplidin®) and Melphalan at 3 days. A) Dose effect curve. B) Fa-CI plot.
Figure 59:
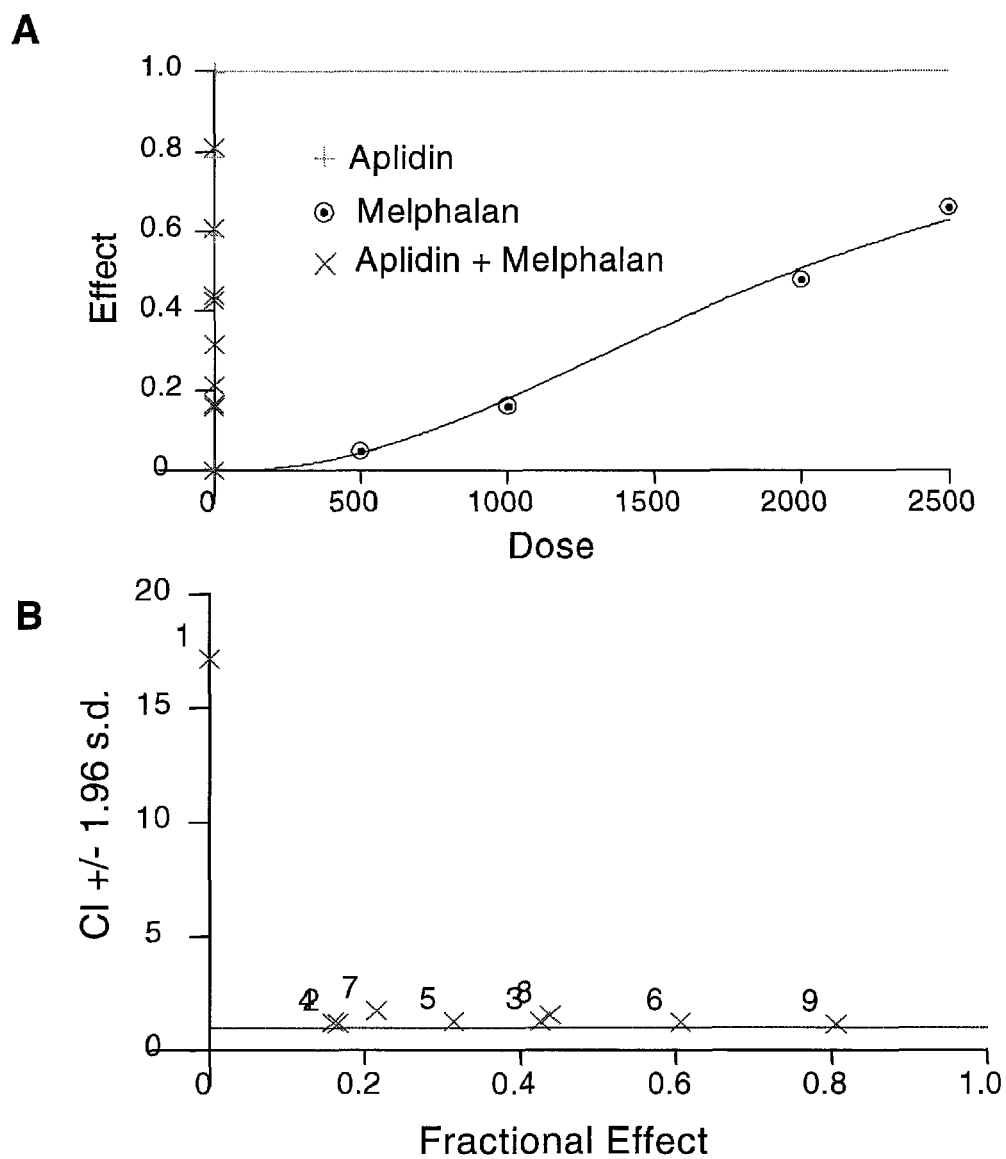
FIG. 59. Combination Aplidine (Aplidin®) and Melphalan at 6 days. A) Dose effect curve. B) Fa-CI plot.

The following combinations showed nearly additive effects at 3 and 6 days (FIGS. 58 and 59 respectively).

Combination of Aplidine with Doxorubicin

Figure 60:
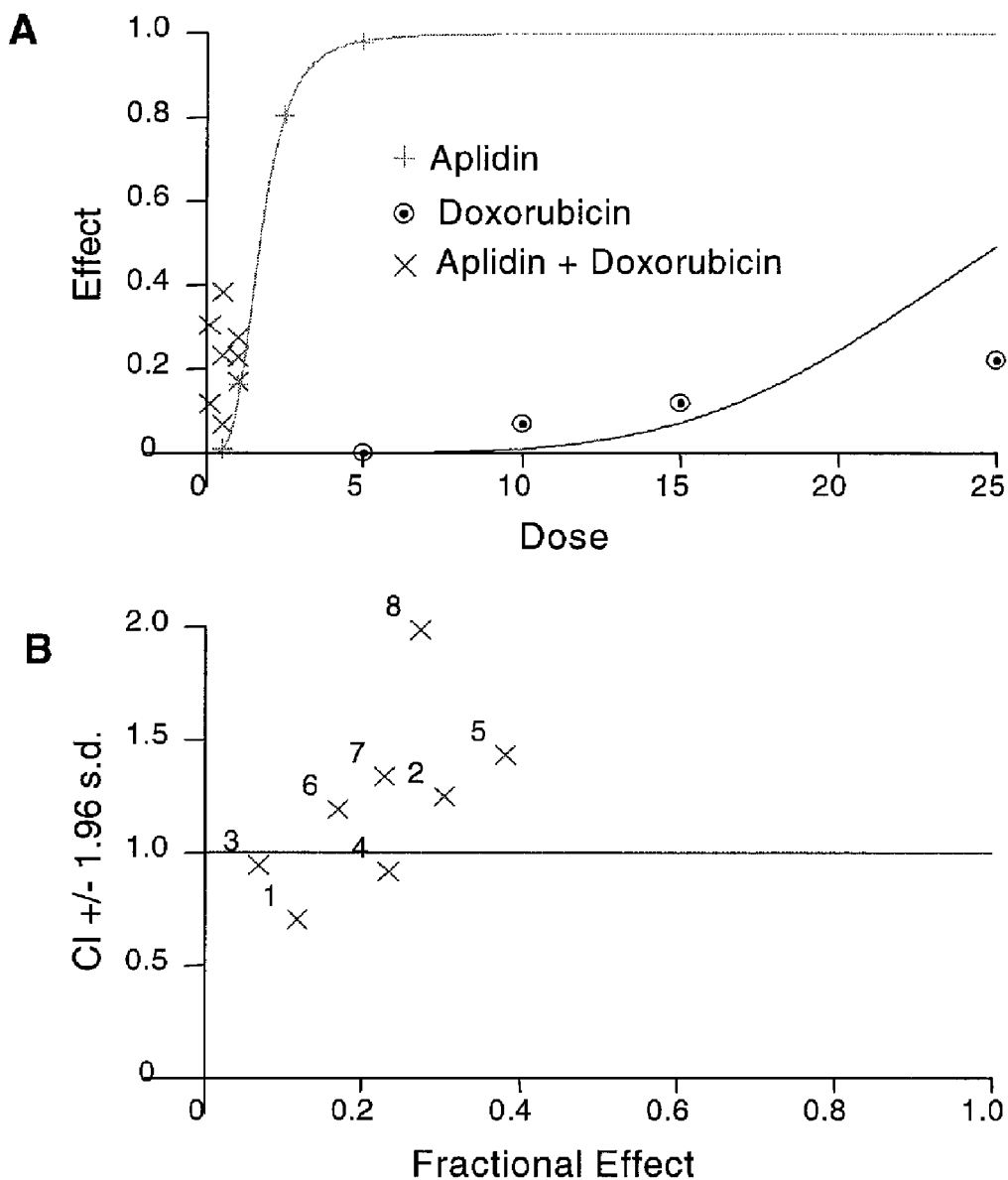
FIG. 60. Combination Aplidine (Aplidin®) and Doxorubicin at 3 days. A) Dose effect curve. B) Fa-CI plot.

At 3 days, only one combination was moderately synergic (FIG. 60, combination 1) and two combinations were additive (FIG. 60, combinations 3 and 4).

Figure 61:
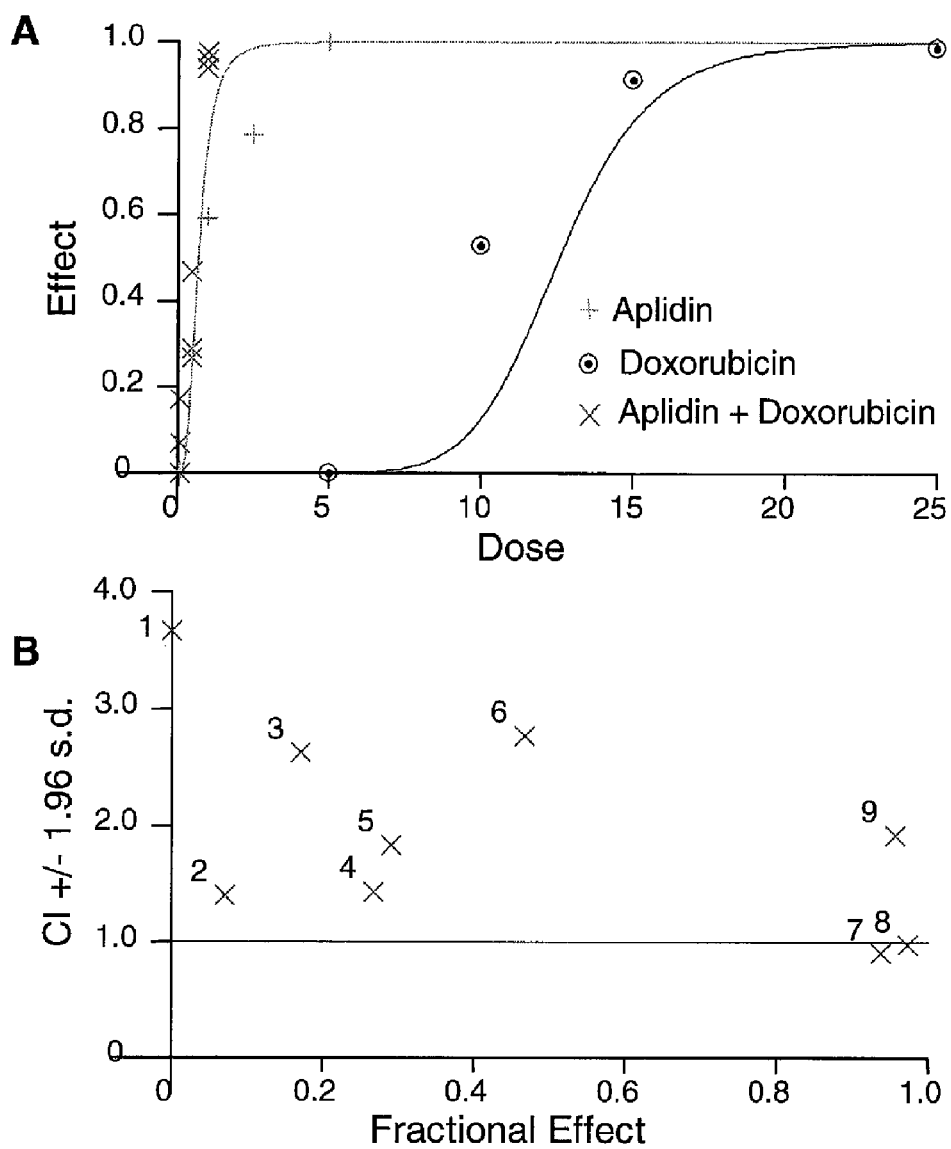
FIG. 61. Combination Aplidine (Aplidin®) and Doxorubicin at 6 days. A) Dose effect curve. B) Fa-CI plot.

At 6 days only two combinations were additive (FIG. 61, combination 7 and 8).

Combination of Aplidine with Lenalidomide (Revlimid®)

Figure 62:
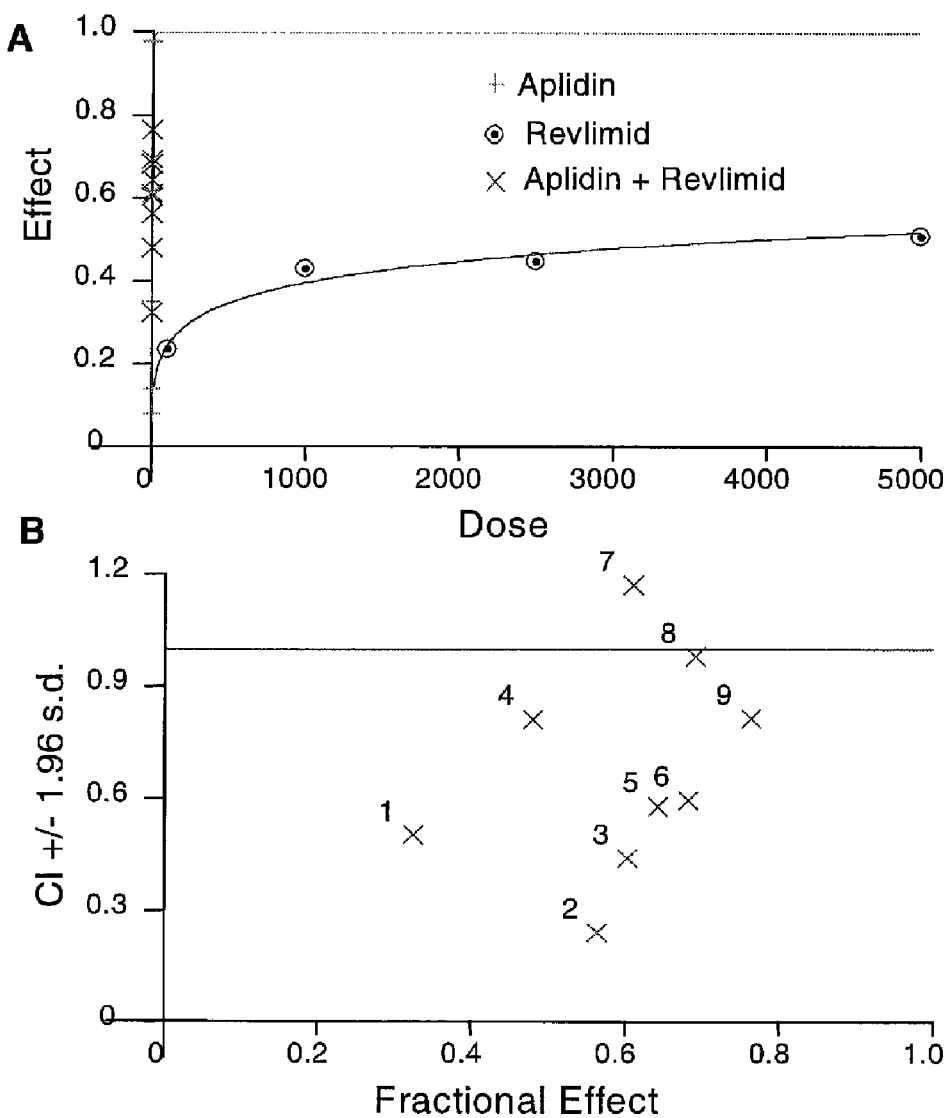
FIG. 62. Combination Aplidine (Aplidin®) and Lenalidomide (Revlimid®) at 3 days. A) Dose effect curve. B) Fa-CI plot.

In the present study, the combination of Aplidine and lenalidomide (Revlimid®) showed greater degrees of synergism than all other combinations examined (FIG. 62).

Figure 63:
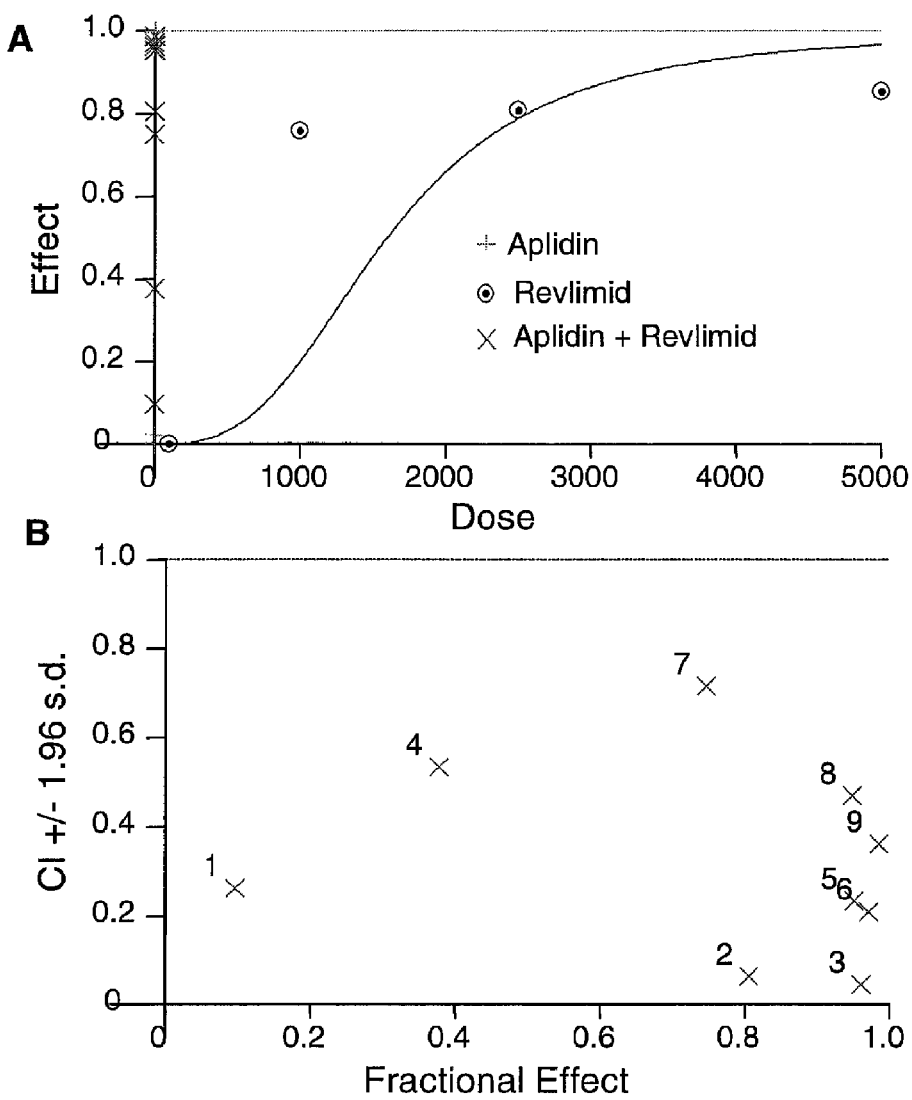
FIG. 63. Combination Aplidine (Aplidin®) and Lenalidomide (Revlimid®) at 6 days. A) Dose effect curve. B) Fa-CI plot.

Remarkably, the synergism was more important at 6 days (FIG. 63).

Combination of Aplidine with Bortezomib

Figure 64:
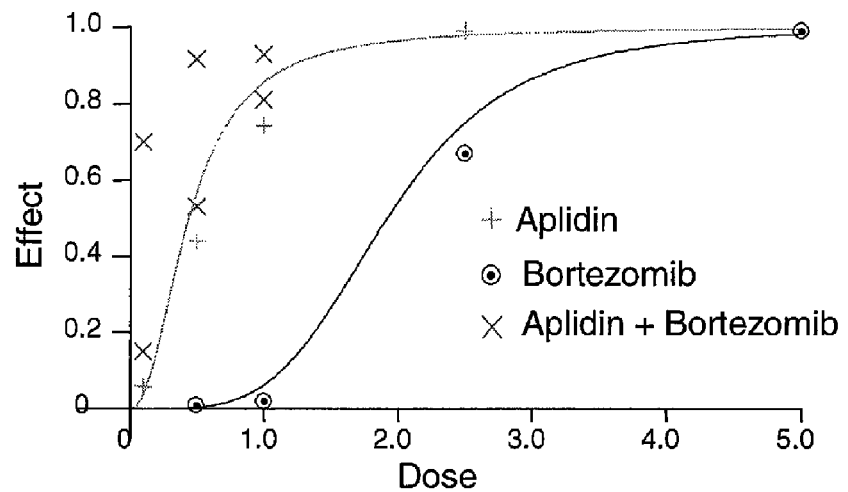
FIG. 64. Combination Aplidine (Aplidin®) and Bortezomib at 3 days. A) Dose effect curve. B) Fa-CI plot.
Figure 64:
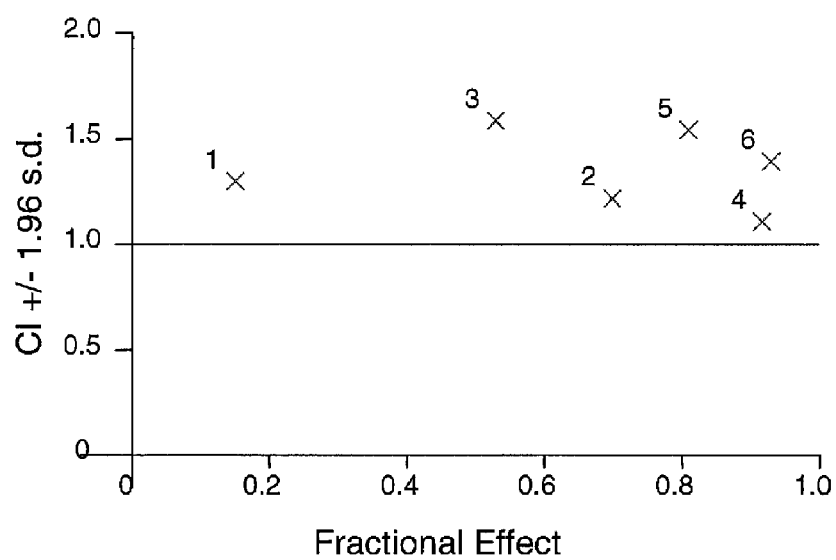
Figure 65:
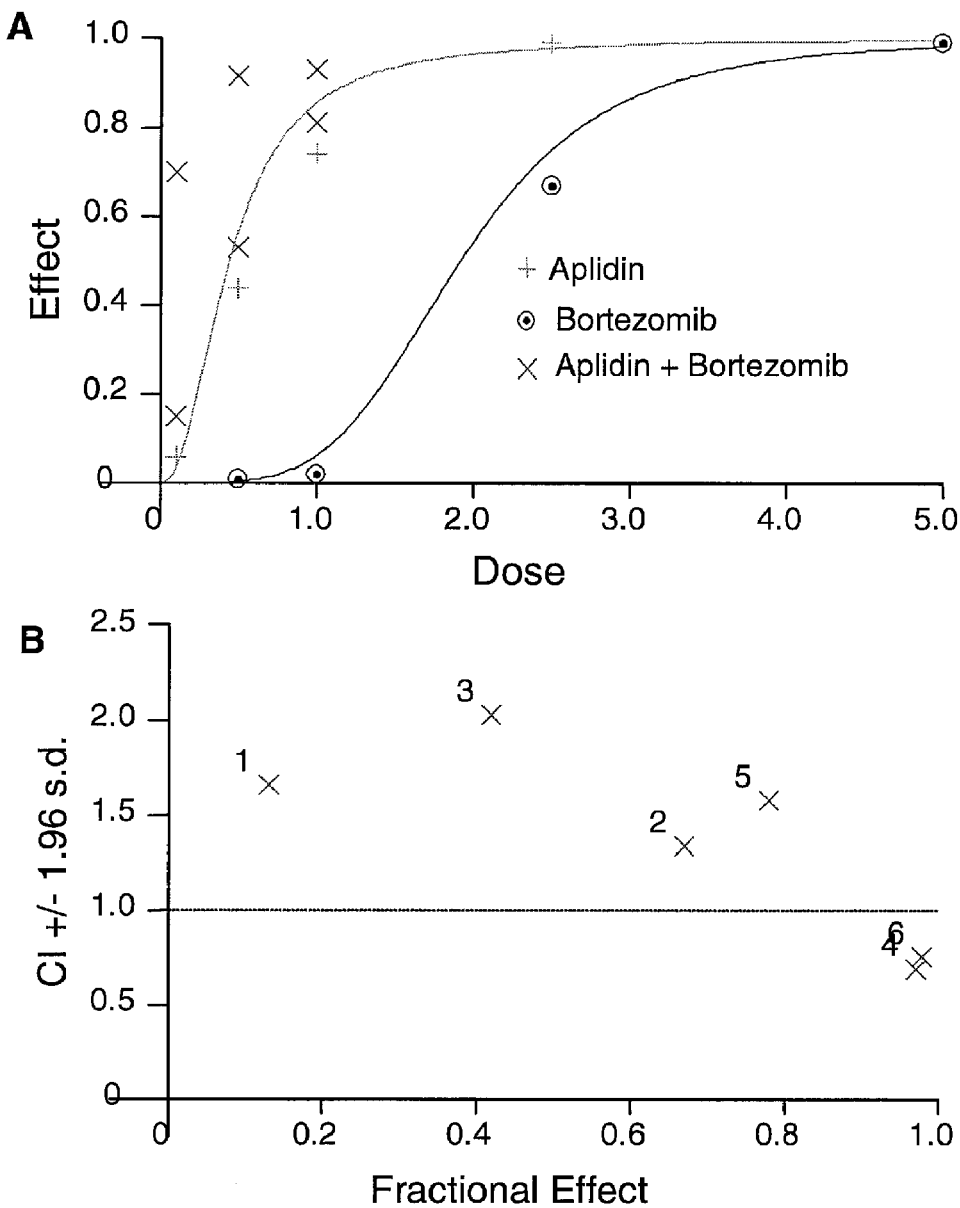
FIG. 65. Combination of Aplidine (Aplidin®) and Bortezomib at 6 days. A) Dose effect curve. B) Fa-CI plot.

This combination showed antagonism at 3 days (FIG. 64); at 6 days synergism was found for two combinations (FIG. 65, combination 4 and 6).

Example 4

In vivo studies to determine the effect of Aplidine in combination with other standard agents in melanoma and renal xenografts.

The purpose of this study was to evaluate the antitumor activity of Aplidine when administered with an antitumoral standard agent, both administered using multiple dosing schedule in several types of tumor xenografts in female athymic mice.

Athymic nude female mice were received from Harlan Sprague Dawley, Madison, Wis. at 4-5 weeks of age. Mice were acclimated to the laboratory for at least one week prior to implantation of tumor. Animals were housed in static cages with food and water allowed ad libitum. Experimental animals were implanted with either tumor fragments derived from transplantation established human tumors or with cells obtain directly from in vitro culture. Tumors were implanted subcutaneously on the right flank on Day 0.

Tumor size measurements were recorded twice weekly beginning on day 4 or 5 using vernier calipers. The formula to calculate volume for a prolate ellipsoid was used to estimate tumor volume from 2-dimensional tumor measurements: tumor volume $(mm^3)$=(length×width$^2$)÷2. Assuming unit density, volume was converted to weight (i.e., 1 $mm^3$=1 mg). When tumors reached an approximate volume range of 100±15 mg, mice were randomized into treatment and control groups. Treatments were initiated and administered on an individual body weight basis. A dose range finding study was performed on each tumor model to determine the appropriate dose level of each compound used in the combination studies.

The following standard of care agents for the various cancer types (indications) were combined with Aplidine (APL) to determine if the combination therapy will provide a greater antitumor activity when compared to the combined activity of the two agents administered as monotherapies.

| Indication | Tumor Model | Compounds |
|---|---|---|
| Melanoma | LOX-IMVI | APL + Carboplatin |
| | | APL + Interleukin-2 (IL-2) |
| | | APL + Interferon-α 2a (INF-α) |
| | | APL + Dacarbazine (DTIC) |

Tables 5-10 show the kinetics of net tumor volume (mean±S.E.M., mg) after initiation of treatment with Aplidine either alone or in combination with a standard of care agent in melanoma and renal cancer xenografts.

Figure 66:
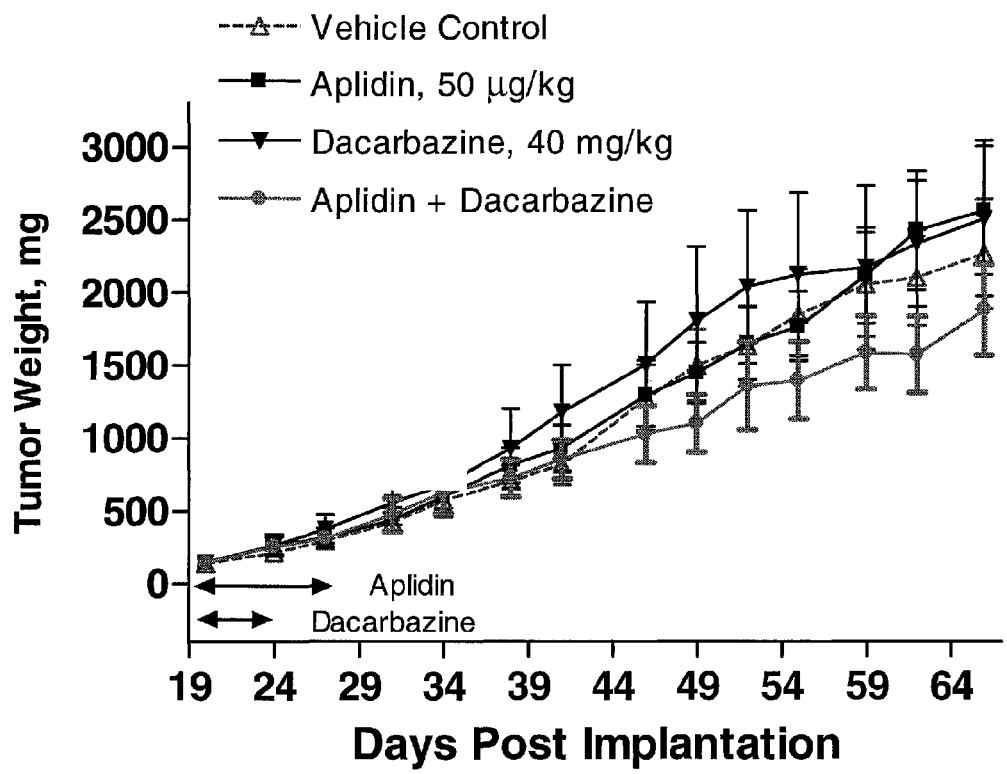
FIG. 66. Kinetics of net tumor volume after initiation of treatment with Aplidine (Aplidin®) as single agent or in combination with Dacarbazine in MRI-H-187 melanoma tumor xenografts.
Figure 67:
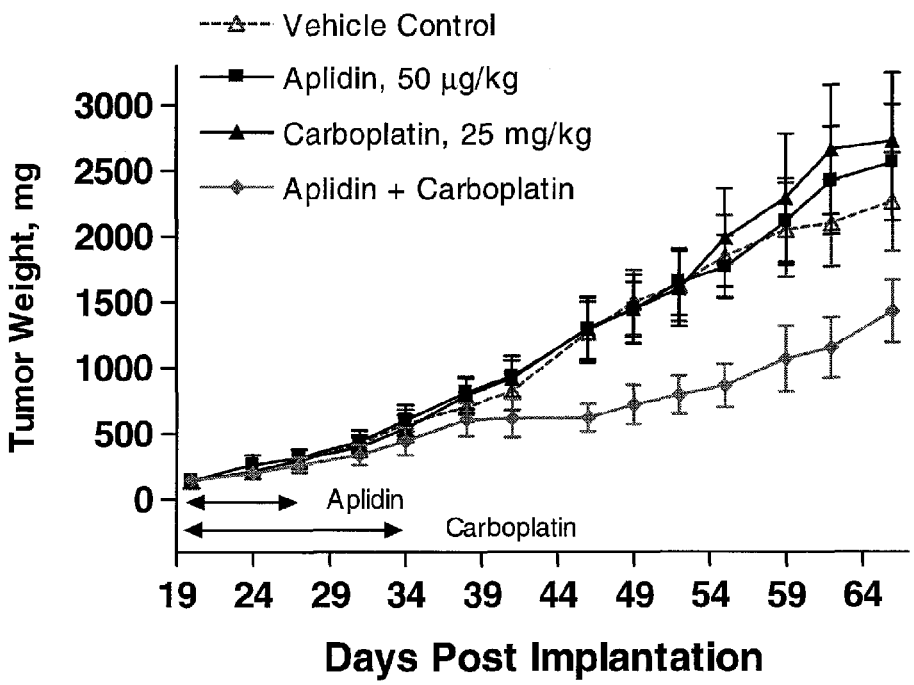
FIG. 67. Kinetics of net tumor volume after initiation of treatment with Aplidine (Aplidin®) as single agent or in combination with Carboplatin in MRI-H-187 melanoma tumor xenografts.

Table 5 and FIGS. 66 and 67 show kinetics of net tumor volume after initiation of treatment with Aplidine (Aplidin®) as single agent or in combination with DTIC and carboplatin in MRI-H187 melanoma tumor xenografts. Aplidine was administered every day for 9 consecutive days by intraperitoneal (i.p.) injection, saline control (sterile saline) every day for 9 consecutive days by i.p. injection, DTIC every day for 5 consecutive days by i.p. injection and Carboplatin one dose every 4 days for a total of 4 treatments by i.p. injection.

TABLE 5

| Drug | Dose/day | Net Tumor Volume ± S.E.M. (mg) | | | | |
|---|---|---|---|---|---|---|
| | | DAY 20 | DAY 24 | DAY 27 | DAY 31 | DAY 34 |
| Saline Control | — | 139 ± 13 | 221 ± 41 | 292 ± 47 | 420 ± 71 | 571 ± 111 |
| Aplidine | 50 µg/kg | 141 ± 12 | 265 ± 72 | 317 ± 64 | 442 ± 81 | 601 ± 116 |
| DTIC | 40 mg/kg | 148 ± 14 | 264 ± 60 | 377 ± 98 | 558 ± 152 | 681 ± 187 |
| Carboplatin | 25 mg/kg | 143 ± 13 | 213 ± 32 | 301 ± 50 | 398 ± 76 | 540 ± 99 |
| Aplidine + DTIC | 50 µg/kg + 40 mg/kg | 145 ± 11 | 257 ± 51 | 311 ± 52 | 476 ± 114 | 632 ± 150 |
| Aplidine + carboplatin | 50 µg/kg + 25 mg/kg | 145 ± 14 | 201 ± 46 | 262 ± 55 | 339 ± 76 | 443 ± 104 |

| Drug | Net Tumor Volume ± S.E.M. (mg) | | | | | |
|---|---|---|---|---|---|---|
| | DAY 38 | DAY 41 | DAY 46 | DAY 49 | DAY 52 | DAY 55 |
| Saline Control | 702 ± 110 | 820 ± 141 | 1270 ± 233 | 1499 ± 247 | 1629 ± 277 | 1848 ± 313 |
| Aplidine | 813 ± 121 | 934 ± 156 | 1295 ± 241 | 1445 ± 211 | 1649 ± 249 | 1767 ± 239 |
| DTIC | 927 ± 274 | 1182 ± 324 | 1508 ± 427 | 1804 ± 507 | 2036 ± 525 | 2123 ± 558 |
| Carboplatin | 793 ± 132 | 917 ± 138 | 1303 ± 237 | 1447 ± 261 | 1603 ± 288 | 1989 ± 373 |
| Aplidine + DTIC | 723 ± 126 | 855 ± 133 | 1028 ± 193 | 1101 ± 197 | 1358 ± 300 | 1397 ± 265 |
| Aplidine + carboplatin | 608 ± 129 | 617 ± 146 | 622 ± 105 | 720 ± 148 | 796 ± 145 | 867 ± 164 |

| Drug | Net Tumor Volume ± S.E.M. (mg) | | |
|---|---|---|---|
| | DAY 59 | DAY 62 | DAY 66 |
| Saline Control | 2049 ± 357 | 2100 ± 330 | 2263 ± 375 |
| Aplidine | 2113 ± 329 | 2423 ± 408 | 2561 ± 441 |
| DTIC | 2166 ± 563 | 2333 ± 433 | 2508 ± 536 |
| Carboplatin | 2292 ± 487 | 2659 ± 492 | 2723 ± 519 |
| Aplidine + DTIC | 1585 ± 251 | 1571 ± 261 | 1879 ± 311 |
| Aplidine + carboplatin | 1070 ± 250 | 1153 ± 230 | 1430 ± 237 |

S.E.M. = Standard error of the mean

-continued

| Indication | Tumor Model | Compounds |
|---|---|---|
| | MRI-H187 | APL + Carboplatin |
| | | APL + Interleukin-2 (IL-2) |
| | | APL + Interferon-α 2a (INF-α) |
| | | APL + Dacarbazine (DTIC) |
| Renal | CaKi-1 | APL + Interleukin-2 (IL-2) |
| | | APL + Interferon-α 2a (INF-α) |
| | | APL + Bevacizumab (Avastin ®) |
| | MRI-H121 | APL + Interleukin-2 (IL-2) |
| | | APL + Interferon-α 2a (INF-α) |
| | | APL + Bevacizumab (Avastin ®) |

From this xenograft study it was concluded that in melanoma MRI-H187 cells the combination of Aplidine with DTIC and Aplidine with carboplatin show a clear statistically significant potentiation of antitumor activity, being more remarkable in the case of the combination with carboplatin.

Figure 68:
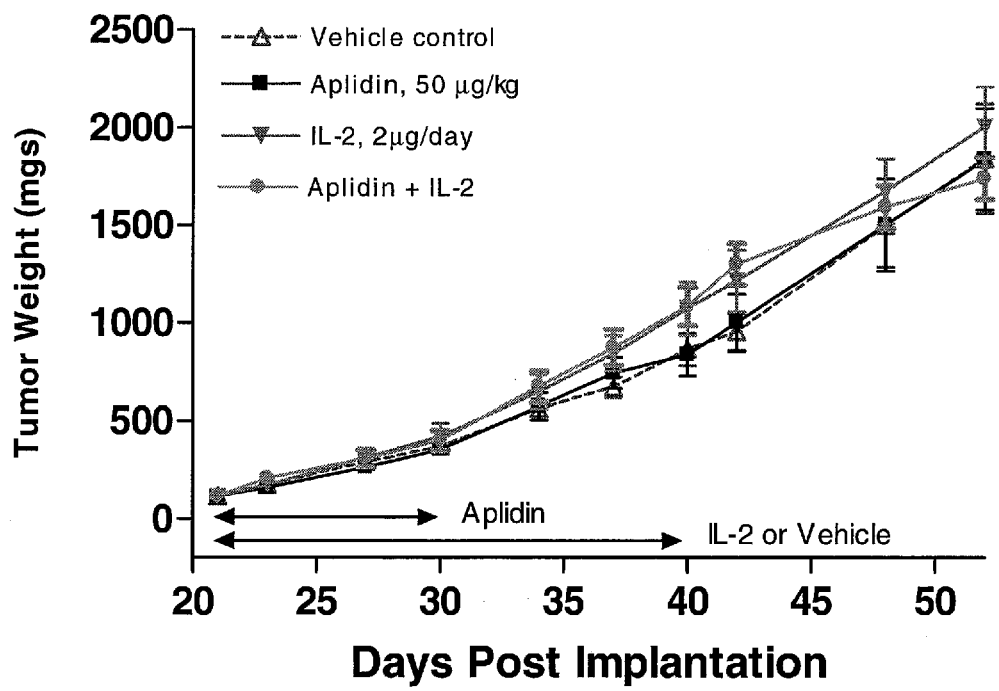
FIG. 68. Kinetics of net tumor volume after initiation of treatment with Aplidine (Aplidin®) as single agent or in combination with Interleukin-2 (IL-2) in MRI-H-187 melanoma tumor xenografts.
Figure 69:
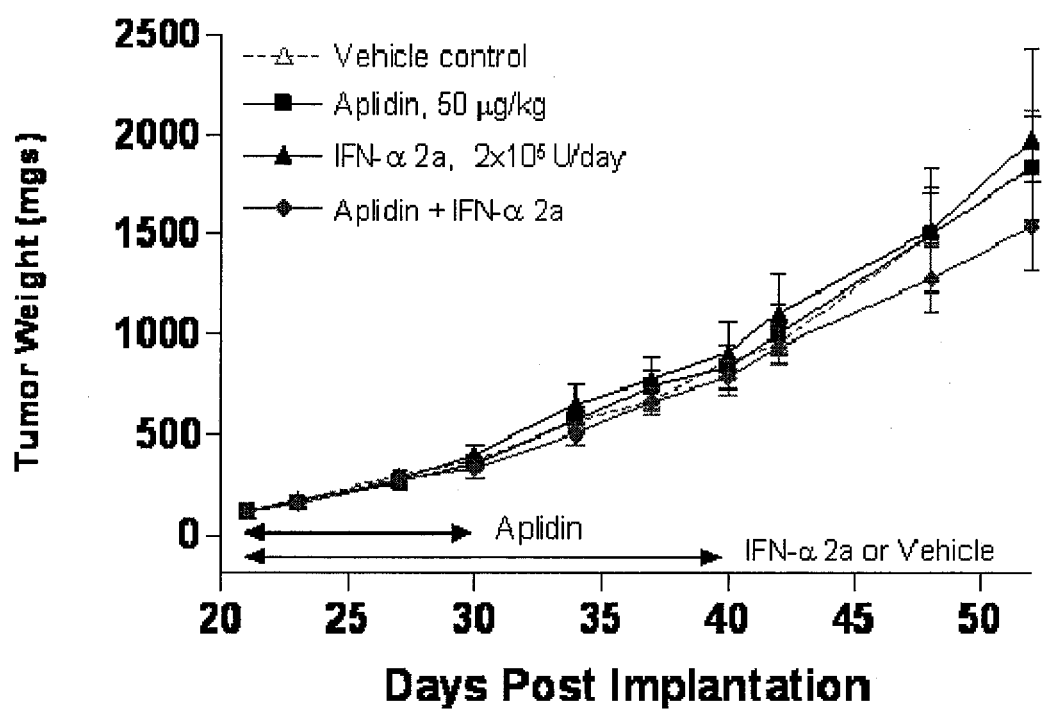
FIG. 69. Kinetics of net tumor volume after initiation of treatment with Aplidine (Aplidin®) as single agent or in combination with Interferon-α 2a (INF-α) in MRI-H-187 melanoma tumor xenografts.

Table 6 and FIGS. 68 and 69 show kinetics of net tumor volume after initiation of treatment with aplidine (Aplidin®) as single agent or in combination with Interleukin-2 (IL-2) and Interferon-α 2a (INF-α) in MRI-H-187 melanoma tumor xenografts. Aplidine was administered every day for 9 consecutive days by i.p injection, saline control (sterile saline) every day for 9 consecutive days by i.p injection, IL-2 every day during 5 weekdays (Monday-Friday) for 3 weeks by i.p. injection and INF-α every day during 5 weekdays (Monday-Friday) for 3 weeks by subcutaneous (s.c.) injection.

TABLE 6

| Drug | Dose/day | Net Tumor Volume ± S.E.M. (mg) | | | | |
|---|---|---|---|---|---|---|
| | | DAY 21 | DAY 23 | DAY 27 | DAY 30 | DAY 34 |
| Saline Control | — | 116 ± 4 | 172 ± 16 | 289 ± 28 | 367 ± 33 | 562 ± 39 |
| Aplidine | 50 µg/kg | 114 ± 7 | 156 ± 15 | 262 ± 32 | 353 ± 34 | 573 ± 70 |
| IL-2 | 2 µg/mouse | 113 ± 4 | 171 ± 24 | 314 ± 46 | 420 ± 68 | 647 ± 88 |
| INF-α | 200,000 U/mouse | 115 ± 5 | 169 ± 19 | 272 ± 40 | 398 ± 54 | 653 ± 99 |
| Aplidine + IL-2 | 50 µg/kg + 2 µg/mouse | 113 ± 4 | 206 ± 19 | 307 ± 42 | 399 ± 51 | 673 ± 80 |
| Aplidine + INF-α | 50 µg/kg + 200,000 U/mouse | 113 ± 7 | 152 ± 12 | 272 ± 32 | 328 ± 48 | 506 ± 56 |

| Drug | Net Tumor Volume ± S.E.M. (mg) | | | | |
|---|---|---|---|---|---|
| | DAY 37 | DAY 40 | DAY 42 | DAY 48 | DAY 51 |
| Saline Control | 669 ± 52 | 863 ± 84 | 953 ± 94 | 1495 ± 211 | 1840 ± 280 |
| Aplidine | 743 ± 81 | 837 ± 108 | 1000 ± 147 | 1500 ± 236 | 1836 ± 260 |
| IL-2 | 843 ± 90 | 1072 ± 136 | 1215 ± 158 | 1672 ± 166 | 2005 ± 202 |
| INF-α | 776 ± 115 | 912 ± 149 | 1104 ± 202 | 1521 ± 311 | 1978 ± 450 |
| Aplidine + IL-2 | 872 ± 93 | 1083 ± 98 | 1299 ± 107 | 1592 ± 110 | 1739 ± 108 |
| Aplidine + INF-α | 664 ± 61 | 783 ± 86 | 938 ± 89 | 1276 ± 170 | 1541 ± 221 |

S.E.M. = Standard error of the mean

From this xenograft study it was concluded that in melanoma MRI-H187 cells the combination of Aplidine with IL-2 and Aplidine with INF-α showed additivity.

Figure 70:
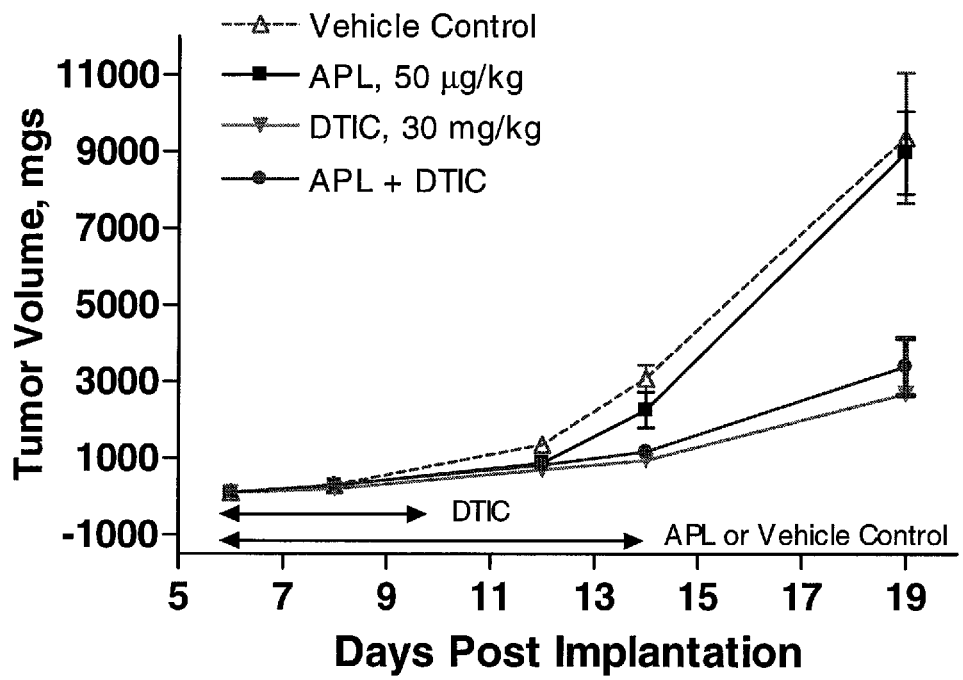
FIG. 70. Kinetics of net tumor volume after initiation of treatment with Aplidine (APL) as single agent or in combination with Dacarbazine (DTIC) in LOX-IMVI melanoma tumor xenografts.
Figure 71:
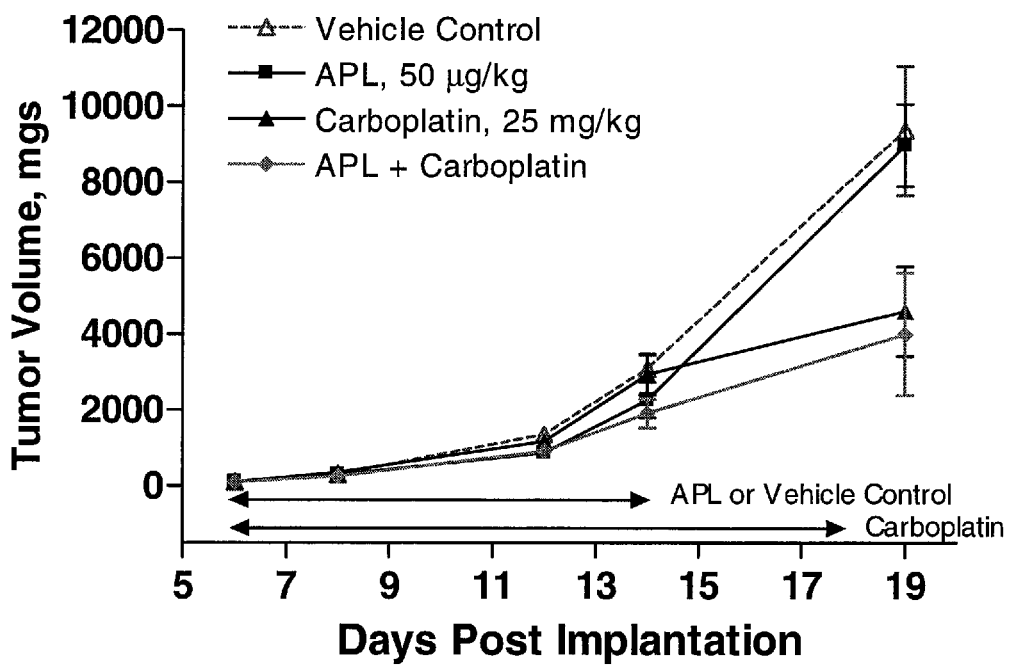
FIG. 71. Kinetics of net tumor volume after initiation of treatment with Aplidine (APL) as single agent or in combination with Carboplatin in LOX-IMVI melanoma tumor xenografts.

Table 7 and FIGS. 70 and 71 show kinetics of net tumor volume after initiation of treatment with Aplidine (APL) as single agent or in combination with DTIC and carboplatin in LOX-IMVI melanoma tumor xenografts. Aplidine was administered every day for 9 consecutive days by i.p. injection, saline control (sterile saline) every day for 9 consecutive days by i.p. injection, DTIC every day for 5 consecutive days by i.p. injection and Carboplatin one dose every 4 days for a total of 4 treatments by i.p. injection.

From this xenograft study it can be concluded that in melanoma LOX-IMVI cells the combination of Aplidine with DTIC shows an additive pattern and the combination of Aplidine with carboplatin shows a trend to synergism.

Figure 72:
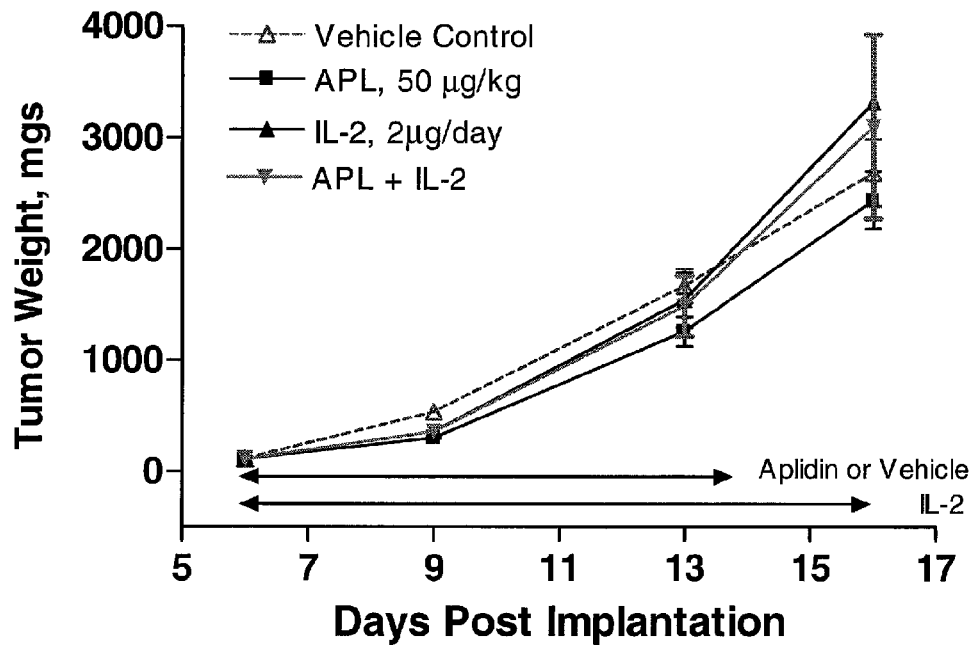
FIG. 72. Kinetics of net tumor volume after initiation of treatment with Aplidine (APL, Aplidin®) as single agent or in combination with Interleukin-2 (IL-2) in LOX-IMVI melanoma tumor xenografts.
Figure 73:
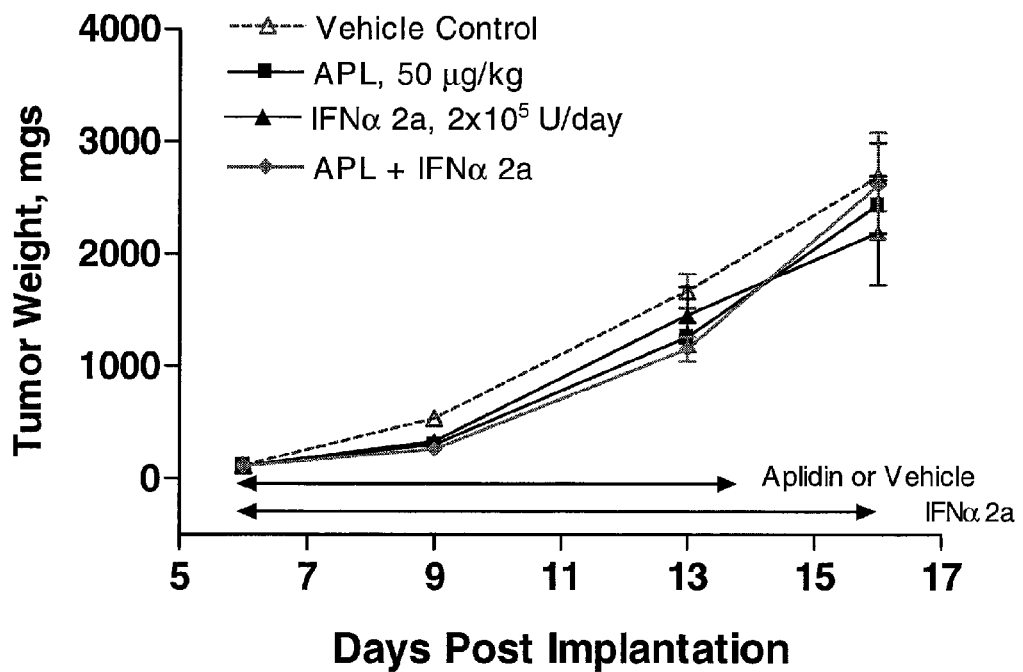
FIG. 73. Kinetics of net tumor volume after initiation of treatment with Aplidine (APL, Aplidin®) as single agent or in combination with Interferon-α 2a (INF-α) in LOX-IMVI melanoma tumor xenografts.

Table 8 and FIGS. 72 and 73 show kinetics of net tumor volume after initiation of treatment with Aplidine (APL) as single agent or in combination with Interleukin-2 (IL-2) and Interferon-α 2a (INF-α) in LOX-IMVI melanoma tumor xenografts. Aplidine was administered every day for 9 consecutive days by i.p injection, saline control (sterile saline) every day for 9 consecutive days by i.p injection, IL-2 every day during 5 weekdays (Monday-Friday) for 3 weeks by i.p. injection and INF-α every day during 5 weekdays (Monday-Friday) for 3 weeks by s.c. injection.

TABLE 7

| Drug | Dose/day | Net Tumor Volume ± S.E.M. (mg) | | | | |
|---|---|---|---|---|---|---|
| | | DAY 6 | DAY 8 | DAY 12 | DAY 14 | DAY 19 |
| Saline Control | — | 107 ± 4 | 292 ± 45 | 1356 ± 174 | 3085 ± 346 | 9364 ± 1702 |
| Aplidine | 50 µg/kg | 107 ± 5 | 288 ± 21 | 863 ± 87 | 2261 ± 459 | 8980 ± 1085 |
| DTIC | 30 mg/kg | 105 ± 5 | 208 ± 25 | 699 ± 57 | 950 ± 57 | 2695 ± 560 |
| Carboplatin | 25 mg/kg | 107 ± 3 | 347 ± 43 | 1167 ± 117 | 2936 ± 543 | 4598 ± 1182 |
| Aplidine + DTIC | 50 µg/kg + 30 mg/kg | 107 ± 4 | 302 ± 16 | 819 ± 57 | 1174 ± 129 | 3397 ± 745 |
| Aplidine + Carboplatin | 50 µg/kg + 25 mg/kg | 107 ± 5 | 253 ± 30 | 909 ± 152 | 1911 ± 374 | 4000 ± 1610 |

S.E.M. = Standard error of the mean

TABLE 8

| Drug | Dose/ day | Net Tumor Volume ± S.E.M. (mg) | | | |
|---|---|---|---|---|---|
| | | DAY 6 | DAY 9 | DAY 13 | DAY 16 |
| Saline Control | — | 111 ± 4 | 532 ± 63 | 1666 ± 152 | 2684 ± 303 |
| Aplidine | 50 μg/kg | 113 ± 4 | 300 ± 15 | 1258 ± 131 | 2436 ± 256 |
| IL-2 | 2 μg/ mouse | 111 ± 5 | 357 ± 51 | 1541 ± 247 | 3315 ± 614 |

TABLE 8-continued

| Drug | Dose/ day | Net Tumor Volume ± S.E.M. (mg) | | | |
|---|---|---|---|---|---|
| | | DAY 6 | DAY 9 | DAY 13 | DAY 16 |
| INF-α | 200,000 U/mouse | 110 ± 4 | 329 ± 39 | 1452 ± 252 | 2188 ± 465 |
| Aplidine + IL-2 | 50 μg/kg + 2 μg/ mouse | 111 ± 3 | 358 ± 50 | 1485 ± 274 | 3097 ± 826 |
| Aplidine + INF-α | 50 μg/kg + 200,000 U/mouse | 112 ± 4 | 260 ± 18 | 1152 ± 110 | 2607 ± 472 |

S.E.M. = Standard error of the mean

From this xenograft study it was concluded that in melanoma LOX-IMVI cells the combination of Aplidine with IL-2 and Aplidine with INF-A show additivity.

Figure 74:
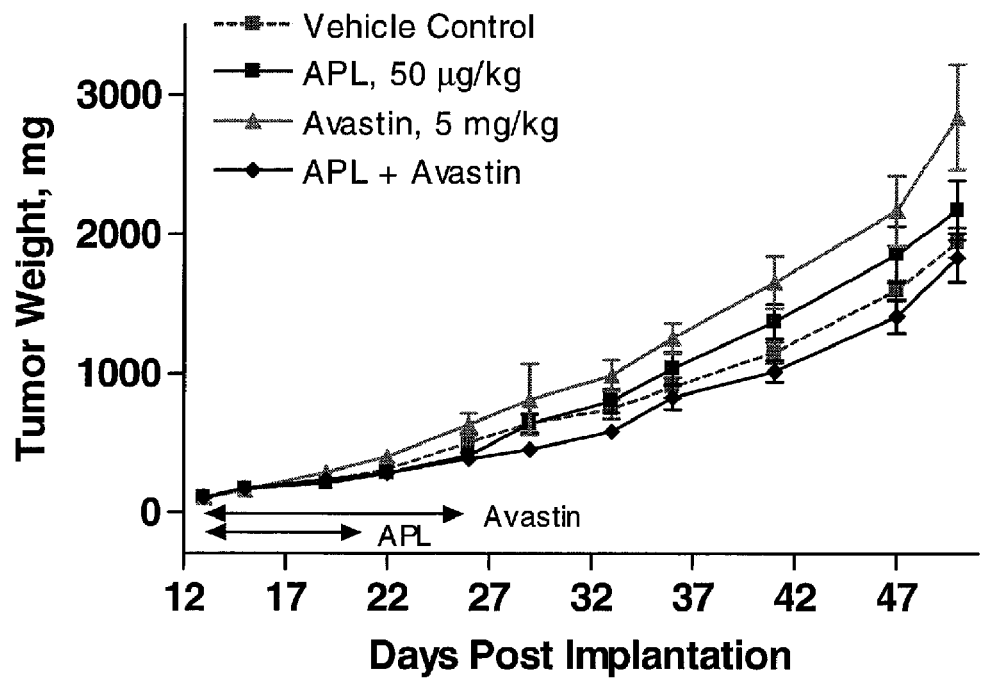
FIG. 74. Kinetics of net tumor volume after initiation of treatment with Aplidine (APL) as single agent or in combination with Bevacizumab (Avastin®) in CaKi-1 renal tumor xenografts.
Figure 75:
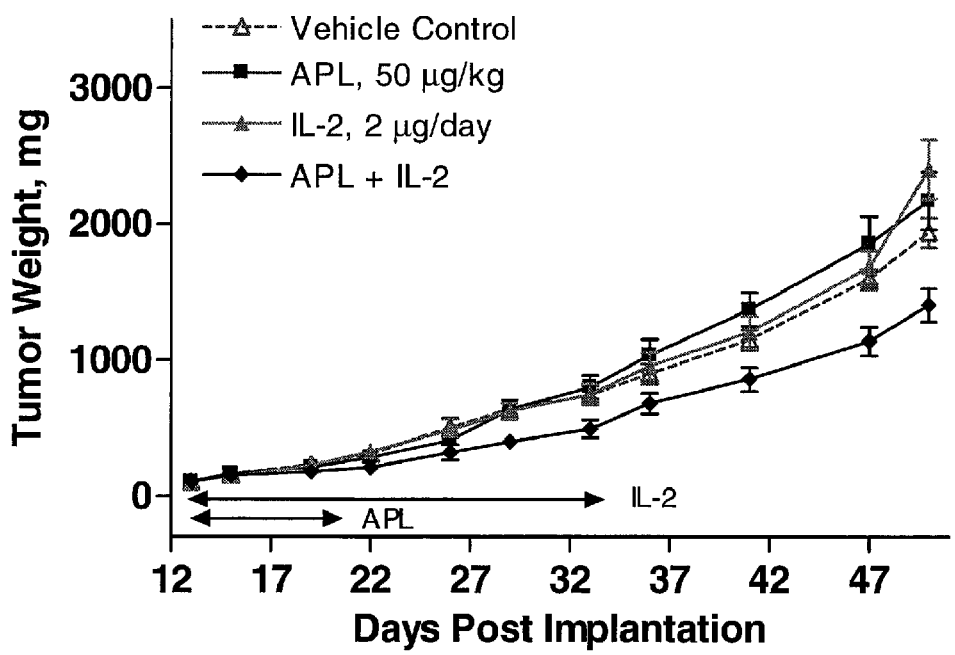
FIG. 75. Kinetics of net tumor volume after initiation of treatment with Aplidine (APL) as single agent or in combination with Interleukin-2 (IL-2) in CaKi-1 renal tumor xenografts.
Figure 76:
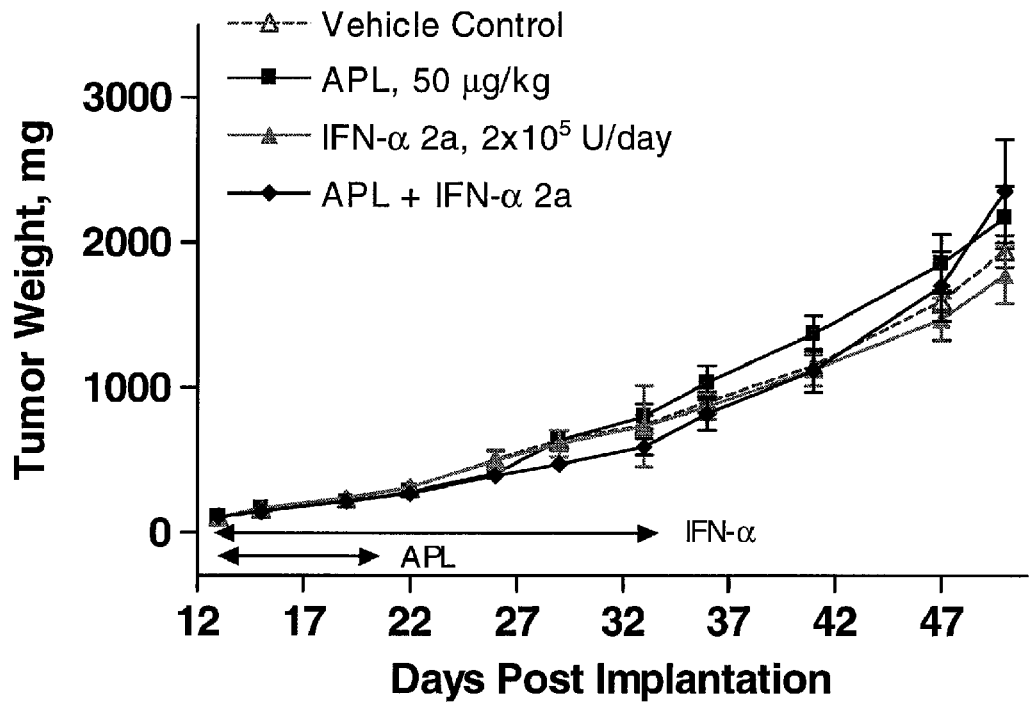
FIG. 76. Kinetics of net tumor volume after initiation of treatment with Aplidine (APL) as single agent or in combination with Interferon-α 2a (INF-α 2a) in CaKi-1 renal tumor xenografts.

Table 9 and FIGS. 74, 75 and 76 show kinetics of net tumor volume after initiation of treatment with aplidine (APL) as single agent or in combination with Bevacizumab (Avastin®), Interleukin-2 (IL-2) and Interferon-α 2a (INF-α) in CaKi-1 renal tumor xenografts. Aplidine was administered every day for 9 consecutive days by i.p injection, saline control (sterile saline) every day for 9 consecutive days by i.p injection, Bevacizumab (Avastin®) every 3 days for a total of 4 treatments by i.p. injection, IL-2 every day during 5 weekdays (Monday-Friday) for 3 weeks by i.p. injection and INF-α every day during 5 weekdays (Monday-Friday) for 3 weeks by s.c. injection.

TABLE 9

| Drug | Dose/ day | Net Tumor Volume ± S.E.M. (mg) | | | | |
|---|---|---|---|---|---|---|
| | | DAY 13 | DAY 15 | DAY 19 | DAY 22 | DAY 26 |
| Saline Control | — | 105 ± 3 | 157 ± 11 | 226 ± 18 | 305 ± 29 | 500 ± 69 |
| Aplidine | 50 μg/kg | 103 ± 3 | 164 ± 12 | 208 ± 12 | 282 ± 26 | 406 ± 46 |
| Avastin ® | 5.0 mg/kg | 105 ± 3 | 162 ± 14 | 286 ± 49 | 398 ± 53 | 632 ± 79 |
| IL-2 | 2 μg/ mouse | 103 ± 3 | 143 ± 15 | 224 ± 21 | 324 ± 25 | 484 ± 49 |
| INF-α | 200,000 U/mouse | 105 ± 3 | 162 ± 14 | 239 ± 28 | 312 ± 43 | 496 ± 60 |
| Aplidine + Avastin ® | 50 μg/kg + 5.0 mg/kg | 106 ± 3 | 169 ± 15 | 238 ± 21 | 283 ± 25 | 383 ± 48 |
| Aplidine + IL-2 | 50 μg/kg + 2 μg/ mouse | 105 ± 3 | 147 ± 21 | 175 ± 16 | 208 ± 34 | 320 ± 57 |
| Aplidine + INF-α | 50 μg/kg + 200,000 U/mouse | 105 ± 4 | 141 ± 12 | 213 ± 27 | 267 ± 29 | 391 ± 39 |

| | Net Tumor Volume ± S.E.M. (mg) | | | | | |
|---|---|---|---|---|---|---|
| Drug | DAY 29 | DAY 33 | DAY 36 | DAY 41 | DAY 47 | DAY 50 |
| Saline Control | 639 ± 64 | 741 ± 69 | 897 ± 75 | 1149 ± 76 | 1595 ± 74 | 1939 ± 110 |
| Aplidine | 637 ± 68 | 800 ± 86 | 1035 ± 117 | 1371 ± 125 | 1855 ± 202 | 2173 ± 213 |
| Avastin ® | 811 ± 90 | 985 ± 111 | 1251 ± 109 | 1654 ± 189 | 2170 ± 253 | 2842 ± 379 |
| IL-2 | 623 ± 59 | 746 ± 77 | 956 ± 102 | 1206 ± 116 | 1684 ± 120 | 2403 ± 218 |
| INF-α | 613 ± 92 | 734 ± 99 | 867 ± 86 | 1125 ± 111 | 1473 ± 149 | 1777 ± 197 |
| Aplidine + Avastin ® | 451 ± 42 | 579 ± 51 | 825 ± 86 | 1014 ± 77 | 1409 ± 122 | 1834 ± 174 |
| Aplidine + IL-2 | 398 ± 49 | 495 ± 64 | 680 ± 75 | 859 ± 88 | 1138 ± 106 | 1404 ± 122 |
| Aplidine + INF-α | 470 ± 39 | 591 ± 56 | 821 ± 115 | 1117 ± 148 | 1699 ± 240 | 2356 ± 354 |

S.E.M. = Standard error of the mean

From this xenograft study it was concluded that in renal CaKi-1 cells the combination of Aplidine with Avastin® and Aplidine with IL-2 show synergism, being more remarkable in the case of the combination with IL-2. On the other hand, the combination of Aplidine with INF-α shows an additive pattern.

Figure 77:
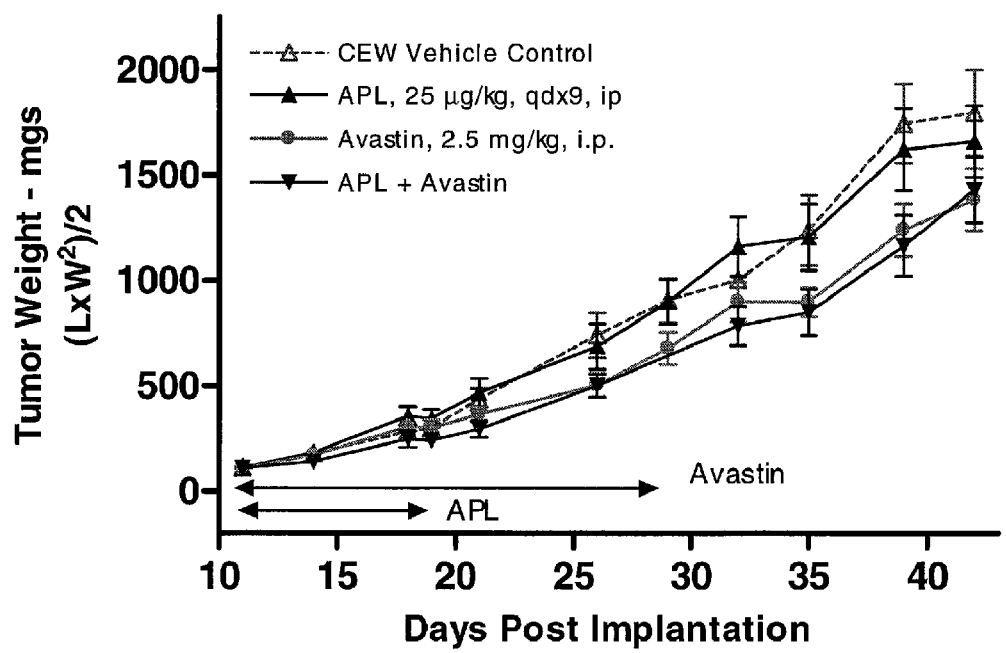
FIG. 77. Kinetics of net tumor volume after initiation of treatment with Aplidine (APL) as single agent or in combination with Bevacizumab (Avastin®) in MRI-H121 renal tumor xenografts.
Figure 78:
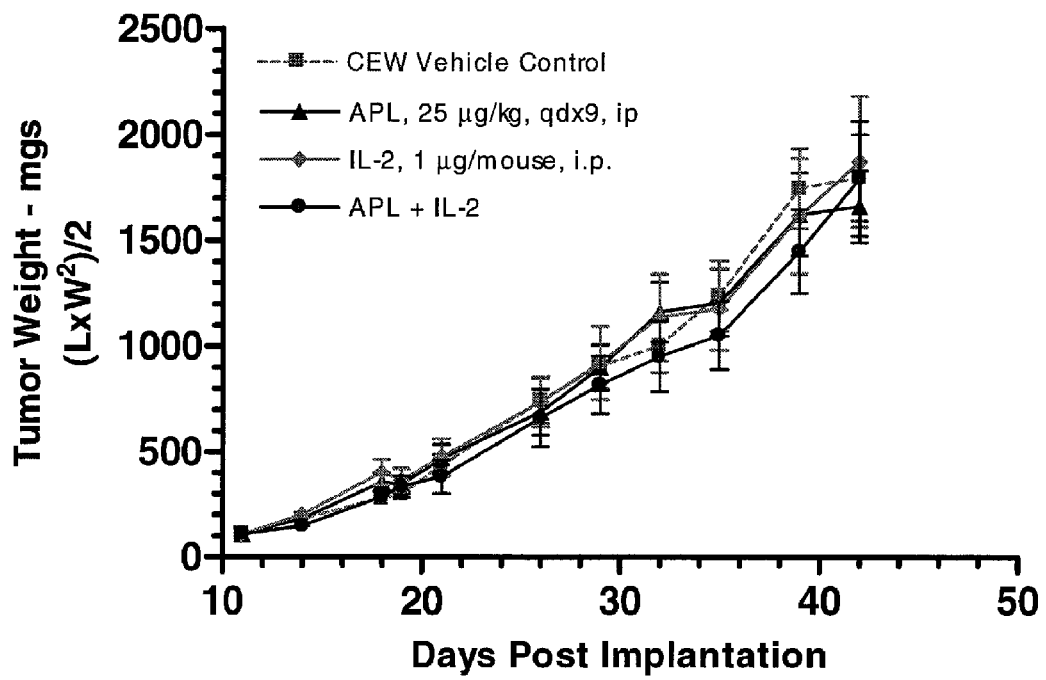
FIG. 78. Kinetics of net tumor volume after initiation of treatment with Aplidine (APL) as single agent or in combination with Interleukin-2 (IL-2) in MRI-H121 renal tumor xenografts.
Figure 79:
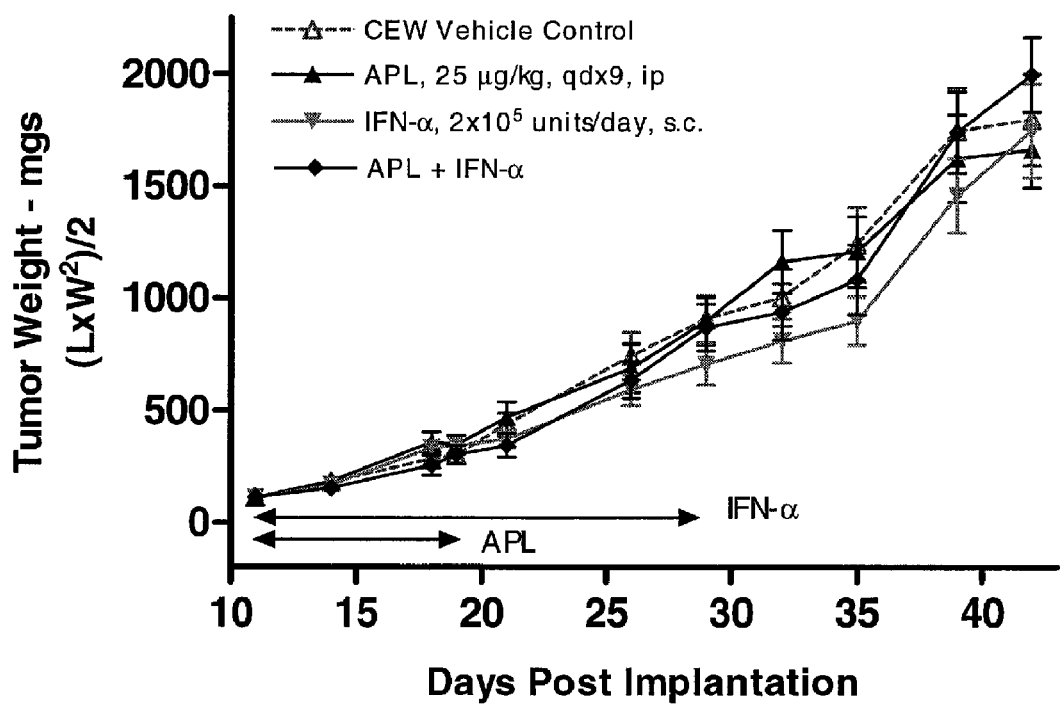
FIG. 79. Kinetics of net tumor volume after initiation of treatment with Aplidine (APL) as single agent or in combination with Interferon-α 2a (INF-α) in MRI-H121 renal tumor xenografts.

Table 10 and FIGS. 77, 78 and 79 show kinetics of net tumor volume after initiation of treatment with aplidine (APL) as single agent or in combination with Bevacizumab (Avastin®), Interleukin-2 (IL-2) and Interferon-α 2a (INF-α) in MRI-H121 renal tumor xenografts. Aplidine was administered every day for 9 consecutive days by i.p injection, saline control (sterile saline) every day for 9 consecutive days by i.p injection, Bevacizumab (Avastin®) every 3 days for a total of 4 treatments by i.p. injection, IL-2 every day during 5 weekdays (Monday-Friday) for 3 weeks by i.p. injection and INF-α every day during 5 weekdays (Monday-Friday) for 3 weeks by s.c. injection.

TABLE 10

| Drug | Dose/day | Net Tumor Volume ± S.E.M. (mg) | | | | |
|---|---|---|---|---|---|---|
| | | DAY 11 | DAY 14 | DAY 18 | DAY 19 | DAY 21 |
| Saline Control | — | 112 ± 6 | 180 ± 15 | 253 ± 27 | 266 ± 33 | 384 ± 52 |
| Aplidine | 25 µg/kg | 108 ± 6 | 182 ± 15 | 357 ± 44 | 345 ± 42 | 467 ± 68 |
| Avastin ® | 2.5 mg/kg | 106 ± 7 | 171 ± 16 | 306 ± 27 | 299 ± 39 | 365 ± 39 |
| IL-2 | 1 µg/mouse | 108 ± 5 | 201 ± 29 | 402 ± 60 | 366 ± 56 | 475 ± 87 |
| INF-α | 200,000 U/mouse | 110 ± 6 | 166 ± 15 | 331 ± 32 | 341 ± 32 | 371 ± 37 |
| Aplidine + Avastin ® | 25 µg/kg + 2.5 mg/kg | 106 ± 7 | 140 ± 20 | 247 ± 39 | 241 ± 30 | 295 ± 39 |
| Aplidine + IL-2 | 25 µg/kg + 1 µg/mouse | 109 ± 5 | 149 ± 16 | 286 ± 33 | 336 ± 51 | 381 ± 79 |
| Aplidine + INF-α | 25 µg/kg + 200,000 U/mouse | 111 ± 7 | 152 ± 23 | 254 ± 45 | 301 ± 42 | 343 ± 52 |

| Drug | Net Tumor Volume ± S.E.M. (mg) | | | | | |
|---|---|---|---|---|---|---|
| | DAY 26 | DAY 29 | DAY 32 | DAY 35 | DAY 39 | DAY 42 |
| Saline Control | 628 ± 106 | 789 ± 105 | 880 ± 126 | 1104 ± 166 | 1512 ± 188 | 1549 ± 204 |
| Aplidine | 688 ± 108 | 898 ± 106 | 1161 ± 141 | 1206 ± 157 | 1622 ± 195 | 1660 ± 169 |
| Avastin ® | 503 ± 57 | 678 ± 77 | 899 ± 93 | 898 ± 69 | 1240 ± 124 | 1383 ± 148 |
| IL-2 | 737 ± 121 | 922 ± 163 | 1138 ± 205 | 1175 ± 192 | 1615 ± 273 | 1873 ± 310 |
| INF-α | 591 ± 69 | 704 ± 91 | 809 ± 96 | 898 ± 108 | 1457 ± 165 | 1747 ± 210 |
| Aplidine + Avastin ® | 501 ± 53 | — | 784 ± 93 | 848 ± 110 | 1166 ± 145 | 1430 ± 155 |
| Aplidine + IL-2 | 662 ± 136 | 817 ± 136 | 951 ± 167 | 1052 ± 161 | 1447 ± 199 | 1791 ± 272 |
| Aplidine + INF-α | 635 ± 83 | 868 ± 104 | 937 ± 125 | 1081 ± 155 | 1739 ± 181 | 1996 ± 167 |

S.E.M. = Standard error of the mean

From this xenograft study it was concluded that in renal MRI-H121 cells the three combinations show an additive pattern.

Example 5

Additional in-vitro assays in multiple myeloma (RPMI-8226 and U266B1) cell lines were conducted to determine the effect of Aplidine in combination with two standard of care chemotherapeutic agents (Bortezomib and Melphalan).

Aplidine as single agent or in combination with either Bortezomib or Melphalan were evaluated against multiple myeloma cell lines, specifically RPMI-8226 and U266B1 cell lines.

These cell lines were cultured in RPMI1640 medium with 10% FBS and 1% L-Glutamine. Each cell line was plated in a 96 well plates at 20,000 cell per well.

First Aplidine, Bortezomib and Melphalan were tested alone to determine the $IC_{50}$ value for each of them individually. To determine $IC_{50}$ value each drug was check at different range of drug concentration, following the procedure as disclosed in Example 1. Table 11 shows the individual $IC_{50}$ obtained with each of the three drugs against the two multiple myeloma cell lines.

TABLE 11

| | $IC_{50}$ (Molar) | |
|---|---|---|
| | RPMI8226 | U2661 |
| Aplidine | 2.93E−08 | 1.39E−09 |
| Bortezomib | 2.29E−09 | 1.66E−05 |
| Melphalan | 1.61E−05 | 3.16E−09 |

In the next step either Bortezomib or Melphalan were combined with Aplidine. In these experiments, concentrations of Aplidine were used with a 1:10 serial dilution. Each serial dilution was paired with 4 different concentrations of Bortezomib or Melphalan.

The plates were incubated for 3 days at 37° C. and 5% $CO_2$. The plates were read using the Promega MTS assay system with MTS being metabolized by living cells turning into formazan which is fluorescent at 490 nm wavelength. This is an indirect measure of cell viability. These were analyzed using the Softmax Pro program which determines cell viability based percent of control wells. This $IC_{50}$ data was then transferred into the CalcuSyn program for combination index analysis. CalcuSyn compares $IC_{50}$ the values of the drugs alone with that of the drugs in combination using an algorithm to determine a combination index. It is important to note that the combination index (CI) is a reflection of the combination effect of the two drugs: CI=1 indicates an additive effect; CI<1 indicates a synergistic effect; and CI>1 indicates a antagonistic effect.

Table 12 summarises those doses wherein a synergistic effect was observed in the combination of Aplidine with Bortezomib against RMPI 8226 cell line:

TABLE 12

| Aplidine concentration | Bortezomib concentration | CI |
|---|---|---|
| 0.2 µg/ml | 1.0 ng/ml | 0.402 |
| | 3.5 ng/ml | 0.911 |
| | 6.0 ng/ml | 0.013 |
| | 8.5 ng/ml | 0.014 |
| 2 µg/ml | 1.0 ng/ml | 0.103 |
| | 3.5 ng/ml | 0.104 |
| | 6.0 ng/ml | 0.106 |
| | 8.5 ng/ml | 0.107 |

Table 13 summarises those dose wherein a synergistic effect was observed in the combination of Aplidine with Melphalan against RMPI 8226 cell line:

TABLE 13

| Aplidine Concentration | Melphalan Concentration | CI |
|---|---|---|
| 0.2 µg/ml | 50 ng/ml | 0.01 |
| | 30 ng/ml | 0.01 |
| | 10 ng/ml | 0.01 |
| | 8 ng/ml | 0.01 |
| 2 µg/ml | 50 ng/ml | 0.103 |
| | 30 ng/ml | 0.103 |
| | 10 ng/ml | 0.103 |
| | 8 ng/ml | 0.103 |

Table 14 summarises those doses wherein a synergistic effect was observed in the combination of Aplidine with Bortezomib against U266B1 cell line:

TABLE 14

| Aplidine Concentration | Bortezomib Concentration | CI |
|---|---|---|
| 0.2 pg/ml | 3.5 ng/ml | 0.602 |
| | 8.5 ng/ml | 0.919 |
| 20 pg/ml | 6.0 ng/ml | 0.758 |
| 0.2 ng/ml | 6.0 ng/ml | 0.852 |
| 2 ng/ml | 3.5 ng/ml | 0.588 |
| | 6.0 ng/ml | 0.776 |
| | 8.5 ng/ml | 0.553 |
| 20 ng/ml | 3.5 ng/ml | 0.892 |
| | 8.5 ng/ml | 0.79 |
| 0.2 µg/ml | 1.0 ng/ml | 0.317 |
| | 3.5 ng/ml | 0.193 |
| | 6.0 ng/ml | 0.251 |
| | 8.5 ng/ml | 0.112 |

Table 15 summarises those doses wherein a synergistic effect was observed in the combination of Aplidine with Melphalan against U266B1 cell line:

TABLE 15

| Aplidine Concentration | Melphalan Concentration | CI |
|---|---|---|
| 0.2 pg/ml | 30 ng/ml | 0.922 |
| | 10 ng/ml | 0.064 |
| | 8 ng/ml | 0.047 |
| 2.0 pg/ml | 50 ng/ml | 0.525 |
| | 30 ng/ml | 0.709 |
| | 10 ng/ml | 0.164 |
| | 8 ng/ml | 0.127 |
| 20 pg/ml | 50 ng/ml | 0.793 |
| | 10 ng/ml | 0.467 |
| | 8 ng/ml | 0.845 |
| 0.2 ng/ml | 10 ng/ml | 0.472 |
| | 8 ng/ml | 0.974 |
| 2 ng/ml | 50 ng/ml | 0.744 |
| | 30 ng/ml | 0.504 |
| | 10 ng/ml | 0.498 |
| | 8 ng/ml | 0.438 |
| 20 ng/ml | 50 ng/ml | 0.888 |
| | 30 ng/ml | 0.688 |
| | 10 ng/ml | 0.573 |
| | 8 ng/ml | 0.573 |
| 0.2 µg/ml | 50 ng/ml | 0.249 |
| | 30 ng/ml | 0.109 |
| | 10 ng/ml | 0.145 |
| | 8 ng/ml | 0.108 |

Example 6

Additional in-vitro assays in leukemia (MOLT4 and K-562) cell lines were conducted to determine the effect of Aplidine in combination with a standard of care chemotherapeutic agent such as Idarubicin.

Aplidine as single agent or in combination with Idarubicin were evaluated against leukemia cell lines, specifically MOLT4 and K562 cell lines.

These cell lines were cultured in RPMI1640 medium with 10% FBS and 2 mM L-Glutamine. Each cell line was plated in a 96 well plates at 20,000 cell per well.

First Aplidine and Idarubicin were tested alone to determine the $IC_{50}$ value for each of them individually. To determine $IC_{50}$ value each drug was check at different range of drug concentration, following the procedure as disclosed in Example 1. Table 16 shows the individual $IC_{50}$ obtained with each of the two drugs against the two leukemia cell lines.

TABLE 16

| | $IC_{50}$ (Molar) | |
|---|---|---|
| | MOLT4 | K562 |
| Aplidine | 1.43E−08 | 2.35E−09 |
| Idarubicin | 5.0E−11 | 6.33E−08 |

In the next step Idarubicin was combined with Aplidine. In the experiment related to MOLT4 cell line, concentrations of Aplidine were used with a 1:10 serial dilution. Each serial dilution was paired with 4 different concentrations of Idarubicin. In the experiment related to K562 cell line, concentrations of Aplidine were used with a 1:5 serial dilution, and Idarubicin concentration was added to each combination set based on a ratio. Thus, combination A was 1:1, combination B was 0.008:1, combination C was 6.4E-05:1 and combination D was 5.12E-07:1.

The plates were incubated for 3 days at 37° C. and 5% $CO_2$. The plates were read using the Promega MTS assay system with MTS being metabolized by living cells turning into formazan which is fluorescent at 490 nm wavelength. This is an indirect measure of cell viability. These were analyzed using the Softmax Pro program which determines cell viability based percent of control wells. This $IC_{50}$ data was then transferred into the CalcuSyn program for combination index analysis. CalcuSyn compares $IC_{50}$ the values of the drugs alone with that of the drugs in combination using an algorithm to determine a combination index. It is important to note that the combination index (CI) is a reflection of the combination effect of the two drugs: CI=1 indicates an additive effect; CI<1 indicates a synergistic effect; and CI>1 indicates a antagonistic effect.

Table 17 summarises those doses wherein a synergistic effect was observed in the combination of Aplidine with Idarubicin against MOLT4 cell line:

TABLE 17

| Aplidine Concentration | Idarubicin Concentration | CI |
|---|---|---|
| 0.2 µg/ml | 3.0 ng/ml | 0.28 |
| | 0.7 ng/ml | 0.052 |
| | 8.0 pg/ml | 0.053 |
| 2 µg/ml | 3.0 ng/ml | 0.669 |
| | 0.7 ng/ml | 0.269 |
| | 8.0 pg/ml | 0.337 |

Table 18 summarises those doses wherein a synergistic effect was observed in the combination of Aplidine with Idarubicin against K562 cell line:

TABLE 18

| Aplidine Concentration | Idarubicin Concentration | CI |
|---|---|---|
| Combo 1:1 ratio | | |
| 6.4 ng/ml | 6.4 ng/ml | 0.054 |
| 32 ng/ml | 32 ng/ml | 0.051 |
| 160 ng/ml | 160 ng/ml | 0.003 |
| 0.8 µg/ml | 0.8 µg/ml | 0.014 |
| 4 µg/ml | 4 µg/ml | 0.222 |
| Combo 0.008:1 ratio | | |
| 256 pg/ml | 32 ng/ml | 0.687 |
| 1.28 ng/ml | 160 ng/ml | 0.025 |
| 6.4 ng/ml | 0.8 µg/ml | 0.026 |
| 32 ng/ml | 4 µg/ml | 0.209 |
| Combo 6.4E-05:1 ratio | | |
| 10.2 pg/ml | 160 ng/ml | 0.194 |
| 51.2 pg/ml | 0.8 µg/ml | 0.677 |
| 256 pg/ml | 4 µg/ml | 0.459 |
| Combo 5.12E-07:1 ratio | | |
| 81.9 fg/ml | 160 ng/ml | 0.091 |
| 0.41 pg/ml | 0.8 µg/ml | 0.365 |
| 2.05 pg/ml | 4 µg/ml | 0.459 |

Example 7

In vivo studies to determine the effect of Aplidine in combination with another standard agent in melanoma xenografts.

The purpose of this study was to evaluate the antitumor efficacy of Aplidine when administered in combination with Carboplatin against subcutaneous-implanted UACC-257 human melanoma cells in female, athymic NCr-nu/nu mice.

The animals were housed in microisolator cages, up to five per cage in a 12-hour light/dark cycle. Six-weeks-old female, athymic NCr-nu/nu mice were acclimated in the laboratories for one week prior to the experiment.

Each mouse was inoculated subcutaneously near the right flank with UACC-257 human melanoma cells from an in vitro cell culture using a 23-gauge needle. Each mouse received $2 \times 10^7$ cells resuspended in 0.2 mL of Matrigel®. A vial with UACC-257 human melanoma frozen cells was thawed and cultured in RPMI 1640 medium containing low glucose (2,000 mg/L), sodium bicarbonate (1,500 mg/mL), 2 mM L-glutamine, and 10% fetal bovine serum (complete medium), and grown in a +37° C. incubator in a humidified atmosphere with 5% $CO_2$ until the necessary number of cells for inoculation of mice was obtained. Cells were harvested after four passages in culture. The cells were removed from the flasks, placed in 50-mL centrifuge tubes and centrifuged at 1,000 rpm for 10 minutes in a refrigerated centrifuge. The cell pellets were resuspended in fresh complete medium. The cell count and viability were determined with a Beckman Coulter VI CELL XR cell counter and viability analyzer. The cell suspension was centrifuged, and the cell pellet was resuspended in Matrigel® at a cell density of $1.0 \times 10^8$ cells/mL and placed on wet ice. The final concentration of Matrigel® in the cell suspension was 56.9%. On the day of cell harvest cell viability was 98.9%.

The day of tumor cell inoculation was designated as Day 0. Individual tumors grew to 150-245 mg in weight (150-245 $mm^3$ in size) on the day of treatment initiation, Day 13 after tumor cell inoculation. Forty animals with tumors in the proper size range were assigned to four treatment groups so that the median tumor weights on the first day of treatment were as close to each other as possible.

The experiment consisted of a vehicle-treated control group of 10 mice and three drug-treated groups of 10 mice per group for a total of 40 mice on the first day of treatment, Day 13 after tumor cell inoculation. Animals in Group 1 were treated i.p. every day for 9 consecutive days (Days 13-21) with a vehicle of Aplidine diluted with saline. Aplidine was administered i.p. every day during 9 days (Days 13-21) at a dosage of 60 µg/kg/dose alone (Group 2) or in combination with Carboplatin (Group 4). Carboplatin was administered i.v. every 4 days for a total of three treatments (Days 13, 17, and 2 1) at a dosage of 50 mg/kg/dose alone (Group 3) or in combination with Aplidine (Group 4). On days when both compounds were administered in Group 4, Aplidine was injected first to all ten animals in the group, followed immediately by the administration of Carboplatin (Group 4).

Group 1 was treated i.p. with 0.18% cremophor EL/0.18% ethanol/0.84% WFI/98.8% saline (injection volume: 0.1 mL/10 g body weight). Aplidine was reconstituted with a vehicle containing 15% cremophor EL/15% ethanol/70% WFI and diluted with saline (injection volume: 0.1 mL/10 g body weight). Carboplatin was prepared in WFI (injection volume: 0.1 mL/10 g body weight).

Animals were observed daily and clinical signed were noted. The s.c. tumors were measured and the animals were weighed twice weekly starting with the first day of treatment, Day 13. Tumor volume was determined by caliper measurements (mm) and using the formula for an ellipsoid sphere:

$$L \times W^2/2 = mm^3,$$

where L and W refer to the larger and smaller perpendicular dimensions collected at each measurement. This formula was also used to calculate tumor weight, assuming unit density (1 $mm^3$=1 mg).

Comparison of the median tumor weight in the treatment groups (T) to the median tumor weight in the control group (T/C×100%) on Day 23 (two days after the end of the treatment) and Day 70 (the day of study termination) were used for evaluation of the antitumor efficacy. % T/C for each treatment is reported in Table 19.

TABLE 19

| Group | | | | | % T/C on day | |
|---|---|---|---|---|---|---|
| No. | Agent | Dosage & Unit | Route | Schedule | 23 | 70 |
| 1 | Vehicle | 0 µg/kg/dose | IP | q1d × 9 | | |
| 2 | Aplidine | 60 µg/kg/dose | IP | q1d × 9 | 90 | 91 |
| 3 | Carboplatin | 50 mg/kg/dose | IV | q4d × 3 | 95 | 60 |
| 4 | Aplidine/ | 60 µg/kg/dose/ | IP | q1d × 9 | 95 | 53 |
|   | Carboplatin | 50 mg/kg/dose | IV | q4d × 3 | | |

Schedule vehicle: q1d × 9 day 13
Schedule Aplidine: q1d × 9 day 13
Schedule Carboplatin: q4d × 3 day 13
Schedule Aplidine/Carboplatin: q1d × 9 day 13/q4d × 3 day 13

The combination treatment of Aplidine plus Carboplatin was tolerated without deaths. The combination treatment resulted in T/C values of 95% and 53% on Days 23 and 70, respectively.

Example 8

In vivo studies to determine the effect of Aplidine in combination with another standard agent in myeloma xenografts.

The purpose of this study was to evaluate the antitumor efficacy of Aplidine when administered in combination with bortezomib against subcutaneous-implanted RPMI 8226 human myeloma cells in male, SCID mice.

The animals were housed in microisolator cages, up to five per cage in a 12-hour light/dark cycle. Six-weeks-old male, SCID mice were acclimated in the laboratories for one week prior to the experiment.

Each mouse was inoculated s.c. near the right flank with RPMI 8226 human myeloma cells from an in vitro cell culture using a 23-gauge needle. Each mouse received $2 \times 10^7$ cells resuspended in 0.2 mL of Matrigel®. The RPMI 8226 human myeloma cells were originally purchased from ATCC (ATCC number: CCL-155). A vial with frozen cells was thawed and cultured in RPMI 1640 medium containing high glucose (4,500 mg/L), sodium bicarbonate (1,500 mg/mL), 2 mM L-glutamine, 10 mM Hepes, 1 mM sodium pyruvate, and 10% fetal bovine serum (complete medium), and grown in a +37° C. incubator in a humidified atmosphere with 5% $CO_2$ until the necessary number of cells for inoculation of mice was obtained. Cells were harvested after four passages in culture. The cells were removed from the flasks, placed in 50-mL centrifuge tubes and centrifuged at 1,000 rpm for 10 minutes in a refrigerated centrifuge. The cell pellets were resuspended in fresh complete medium. The cell count and viability were determined with a Beckman Coulter VI CELL XR cell counter and viability analyzer. The cell suspension was recentrifuged, and the cell pellet was resuspended in Matrigel® at a cell density of $1.0 \times 10^8$ cells/mL and placed on wet ice. The final concentration of Matrigel® in the cell suspension was 78.3%. On the day of cell harvest cell viability was 89.3%.

The day of tumor cell inoculation was designated as Day 0. Individual tumors grew to 75-188 mg in weight (75-188 mm³ in size) on the day of treatment initiation, Day 18 after tumor cell inoculation. Those animals selected with tumors in the proper size range were assigned to four treatment groups so that the median tumor weights on the first day of treatment were as close to each other as possible.

The experiment consisted of a vehicle-treated control group of 10 mice and three drug-treated groups of 10 mice per group for a total of 40 mice on the first day of treatment, Day 18 after tumor cell inoculation. Animals in Group 1 were treated i.p. for two rounds every day during 9 consecutive days (Days 18-26 and Days 38-46) with a vehicle of Aplidine diluted with saline. Aplidine was administered i.p. for two rounds every day during 9 consecutive days (Days 18-26 and Days 38-46) at a dosage of 60 µg/kg/dose alone (Group 2) or in combination with bortezomib (Group 4). Bortezomib was administered i.v. at a dosage of 0.35 mg/kg/dose for four weeks every 3 days for a total of 2 treatments starting on Day 18 followed by one more i.v. injection administered on Day 46 alone (Group 3) or in combination with Aplidine (Group 4). On days when both compounds were administered in Group 4, Aplidine was injected first to all ten animals in the group, followed immediately by the administration of bortezomib (Group 4).

Group 1 was treated i.p. with 0.18% cremophor EL/0.18% ethanol/0.84% WFI/98.8% saline (injection volume: 0.1 mL/10 g body weight). Aplidine was reconstituted with a vehicle containing 15% cremophor EL/15% ethanol/70% WFI and diluted with saline (injection volume: 0.1 mL/10 g body weight). Velcade® (Bortezomib) was prepared in saline (injection volume: 0.1 mL/10 g body weight).

Animals were observed daily and clinical signed were noted. The s.c. tumors were measured and the animals were weighed twice weekly starting with the first day of treatment, Day 18 after tumor cell inoculation. Tumor volume was determined by caliper measurements (mm) and using the formula for an ellipsoid sphere as described in Example 7.

Comparison of the median tumor weight in the treatment groups (T) to the median tumor weight in the control group (T/C×100%) on Day 27 (one day after the end of the first round of Aplidine treatment) and Day 48 (two days after the end of the treatment with Aplidine and Bortezomib) were used for evaluation of the antitumor efficacy. % T/C for each treatment is reported in Table 20.

TABLE 20

| | | | | % T/C on day | |
|---|---|---|---|---|---|
| Group No. | Agent | Dosage & Unit | Route | 27 | 48 |
| 1 | Vehicle | 0 µg/kg/dose | IP | | |
| 2 | Aplidine | 60 µg/kg/dose | IP | 76 | 63 |
| 3 | Bortezomib | 0.35 mg/kg/dose | IV | 70 | 67 |
| 4 | Aplidine/ | 60 µg/kg/dose/ | IP | 49 | 31 |
|   | Bortezomib | 0.35 mg/kg/dose | IV | | |

Schedule vehicle: q1d × 9 day 18, 38
Schedule Aplidine: q1d × 9 day 18, 38
Schedule Bortezomib: q3d × 2 day 18, 25, 32, 39; q1d × 1 day 46
Schedule Aplidine/Bortezomib: q1d × 9 day 18, 38/q3d × 2 day 18, 25, 32, 39; q1d × 1 day 46

The combination treatment of Aplidine plus Bortezomib was tolerated without deaths. The combination treatment was effective in the inhibition of the growth of the RPMI 8226 myeloma cells, resulting in T/C values of 49% and 31% on Days 27 and 48, respectively. The antitumor activity of the combination treatment was greater than additive compared to the antitumor activity produced by administration of each compound alone.

Example 9

In vivo studies to determine the effect of Aplidine in combination with another standard agent in lymphoma xenografts.

The purpose of this study was to evaluate the antitumor efficacy of Aplidine when administered in combination with rituximab against subcutaneous-implanted RL human lymphoma cells in female, SCID mice.

The animals were housed in microisolator cages, up to five per cage in a 12-hour light/dark cycle. Six-weeks-old male, SCID mice were acclimated in the laboratories for one week prior to the experiment.

Each mouse was inoculated s.c. near the right flank with RL human lymphoma cells from an in vitro cell culture using a 23-gauge needle. Each mouse received $1.0 \times 10^7$ cells resuspended in 0.2 mL of Matrigel®. A vial with frozen cells was thawed and cultured in RPMI 1640 medium containing high glucose (4,500 mg/L), sodium bicarbonate (1,500 mg/mL), 2 mM L-glutamine, 10 mM Hepes, 1 mM sodium pyruvate, and 10% fetal bovine serum (complete medium), and grown in a +37° C. incubator in a humidified atmosphere with 5% $CO_2$ until the necessary number of cells for inoculation of mice was obtained. Cells were harvested after six passages in culture. The cells were removed from the flasks, placed in 50-mL centrifuge tubes and centrifuged at 1,000 rpm for 10 minutes in a refrigerated centrifuge. The cell pellets were resuspended in fresh complete medium. The cell count was determined with a Coulter Model Z1 cell counter and viability was measured following propidium iodide staining and analyzed using a Beckman Coulter EPICS XL flow cytometer. The cell suspension was recentrifuged, and the cell pellet was resuspended in Matrigel® at a cell density of $5.0 \times 10^7$ cells/mL and placed on wet ice. The final concentration of Matrigel® in the cell suspension was 73.0%. On the day of cell harvest cell viability was 98.9%.

The day of tumor cell inoculation was designated as Day 0. Individual tumors grew to 100-196 mg in weight (100-196 $mm^3$ in size) on the day of treatment initiation, Day 15 after tumor cell inoculation. Forty animals with tumors in the proper size range were assigned to four treatment groups so that the median tumor weights in all groups on the first day of treatment were as close to each other as possible.

The experiment consisted of a vehicle-treated control group of 10 mice and three drug-treated groups of 10 mice per group for a total of 40 mice on the first day of treatment, Day 15 after tumor cell inoculation. Animals in Group 1 were treated i.p. for two rounds every day during 9 consecutive days (Days 15-23 and Days 28-36) with a vehicle of Aplidine diluted with saline. Aplidine was administered i.p. for two rounds every day during 9 consecutive days (Days 15-23 and Days 28-36) at a dosage of 60 µg/kg/dose alone (Group 2) or in combination with Rituximab (Group 4). Rituximab was administered i.p. at a dosage of 20 mg/kg/dose for four weekly rounds of treatment every 3 days for a total of 2 treatments (q3 d×2 schedule) starting on Day 15 alone (Group 3) or in combination with Aplidine (Group 4). On days when both compounds were administered in Group 4, Aplidine was injected first to all ten animals in the group, followed immediately by the administration of Rituximab (Group 4).

Group 1 was treated i.p. with 0.18% cremophor EL/0.18% ethanol/0.84% WFI/98.8% saline (injection volume: 0.1 mL/10 g body weight). Aplidine was reconstituted with a vehicle containing 15% cremophor EL/15% ethanol/70% WFI and diluted with saline (injection volume: 0.1 mL/10 g body weight). Rituxan® (Rituximab) was prepared in saline (injection volume: 0.1 mL/10 g body weight).

Animals were observed daily and clinical signed were noted. The s.c. tumors were measured and the animals were weighed twice weekly starting with the first day of treatment, Day 15. Tumor volume was determined by caliper measurements (mm) and using the formula for an ellipsoid sphere as described in Example 7.

Comparison of the median tumor weight in the treatment groups (T) to the median tumor weight in the control group (T/C×100%) on Day 24 (one day after the end of the first 9-day round of Aplidine treatment) and Day 38 (two days after the end of the second 9-day round of Aplidine treatment) were used for evaluation of the antitumor efficacy. % T/C for each treatment is reported in Table 21.

TABLE 21

| Group No. | Agent | Dosage & Unit | Route | % T/C on day 24 | 38 |
|---|---|---|---|---|---|
| 1 | Vehicle | 0 µg/kg/dose | IP | | |
| 2 | Aplidine | 60 µg/kg/dose | IP | 84 | 84 |
| 3 | Rituximab | 20 mg/kg/dose | IP | 95 | 102 |
| 4 | Aplidine/ | 60 µg/kg/dose/ | IP | 69 | 74 |
|   | Rituximab | 20 mg/kg/dose | IP | | |

Schedule vehicle: q1d × 9 day 15, 28
Schedule Aplidine: q1d × 9 day 15, 28
Schedule Rituximab: q3d × 2 day 15, 22, 29, 36
Schedule Aplidine/Rituximab: q1d × 9 day 15, 28/q3d × 2 day 15, 22, 29, 36

The combination treatment of Aplidine plus Rituximab was tolerated without deaths. The combination treatment was effective in the inhibition of the growth of the RL lymphoma cells, resulting in T/C values of 69% and 74% on Days 24 and 38, respectively. Therefore, when Aplidine is combined with Rituximab a potentiation of the anti-tumor activity was observed.

Example 10

In vivo studies to determine the effect of Aplidine in combination with other standard agents (triple combinations) on multiple myeloma tumor cell lines.

In the present study triple combinations of antitumor agents were analyzed. All the combinations were tested using cell viability assay (MMT) in MM.1S cell line, a very sensitive MM cell line. Results were analyzed using the Calcusyn software.

Cell Lines and Cell Culture Reagents

The dexamethasone-sensitive MM cell line MM.1S was kindly provided by Dr. S Rudikoff, Bethesda Md.). The cell line was grown in RPMI 1640 medium supplemented with 10% heat-inactivated fetal bovine serum, 100 U/ml penicillin, 100 µg/ml streptomycin and 2 mM L-glutamine. All cell culture media and reagents were purchased from Invitrogen Corporation (Carlsbad, Calif.).

Cell Viability Assays

The analysis of MM cell proliferation was assessed using the methylthiotetrazole (MTT; Sigma, St. Louis Mo.) calorimetric assay. MM cell lines were seeded at a density of 50000 cells/200 µl medium per well in 48-well plates, and treated with a determined drug dose and time. Two hours before the end of the treatment, a MTT solution (5 mg/ml in PBS; usually a 10% of the volume in each well) was added and the tetrazolium salt was reduced by metabolically active cells to coloured formazan crystals. After solubilization of these crystals by overnight incubation with 10% SDS-HCl solution, absorbance was measured at 570 nm with correction at 630 nm. Four wells were analyzed for each condition, and the results are presented as the mean±SD of quadruplicates of a representative experiment that was repeated at least three times.

Isobologram Analysis

The interaction between Aplidine and other anti-MM agents was analyzed using the Calcusyn software program (Biosoft, Ferguson, Mo.). Data from cell viability assay (MTT) were expressed as the fraction of cells affected by the dose (Fa) in drug treated cells as compared to untreated cells (control). This program is based upon the Chou-Talalay method according to the following equation CI=(D) 1/(Dx)1+(D)1(D)2/(Dx)1(Dx)2 where (D)1 and (D)2 are the doses of drug 1 and 2 that have the same x effect when used alone.

The computer-calculated combination index (CI) was used to judge the outcomes of a combination: CI>1, CI=1, and CI<1 indicating antagonism, additive, and synergistic effects, respectively. The conformity of data to the median-effect principle can be readily manifested by the linear correlation coefficient (r) of the median-effect plot: log(fa/fu)=m log (D)−m log(Dm), where D is the dose, Dm is the dose required for a 50% effect, fa is the fraction affected by dose, fu is the unaffected fraction, and m is a coefficient of the sigmoidicity of the dose-effect curve. For each combination a non-constant ratio combination was utilized.

Results

Combination of Aplidine+Lenalidomide (Revlimid®)+Dexamethasone

Figure 80:
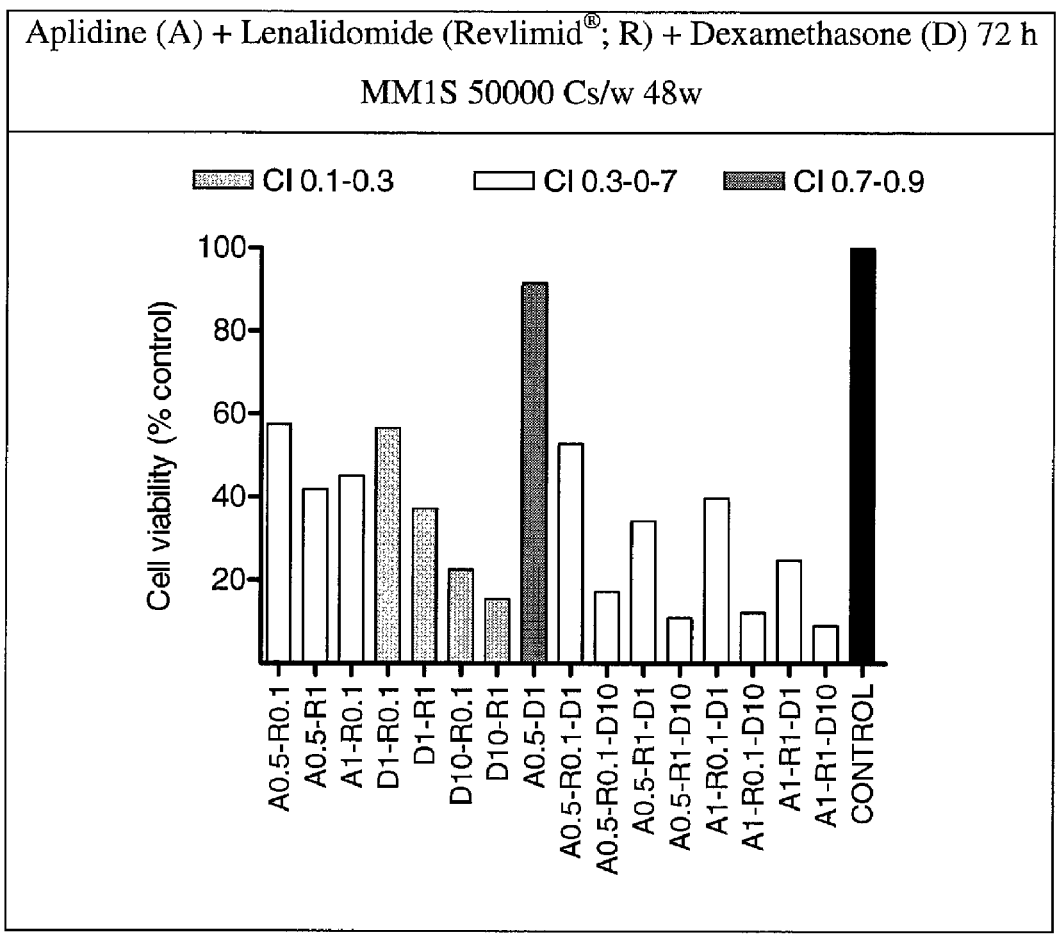
FIG. 80. Combination of Aplidine (A)+Lenalidomide (Revlimid®; R)+Dexamethasone (D) in MM1S after 72 h of treatment. Aplidine doses are expressed in nM units, Lenalidomide doses are expressed in μM units and Dexamethasone doses are expressed in nM units.

The addition of Dexamethasone to the combination of Aplidine+Lenalidomide showed an important synergy in all the combinations tested in the sensitive cell line (MM1S) (FIG. 80). In FIG. 80 Aplidine doses are expressed in nM units, Lenalidomide doses are expressed in µM units and Dexamethasone doses are expressed in nM units.

Combination of Aplidine+Bortezomib+Dexamethasone

Figure 81:
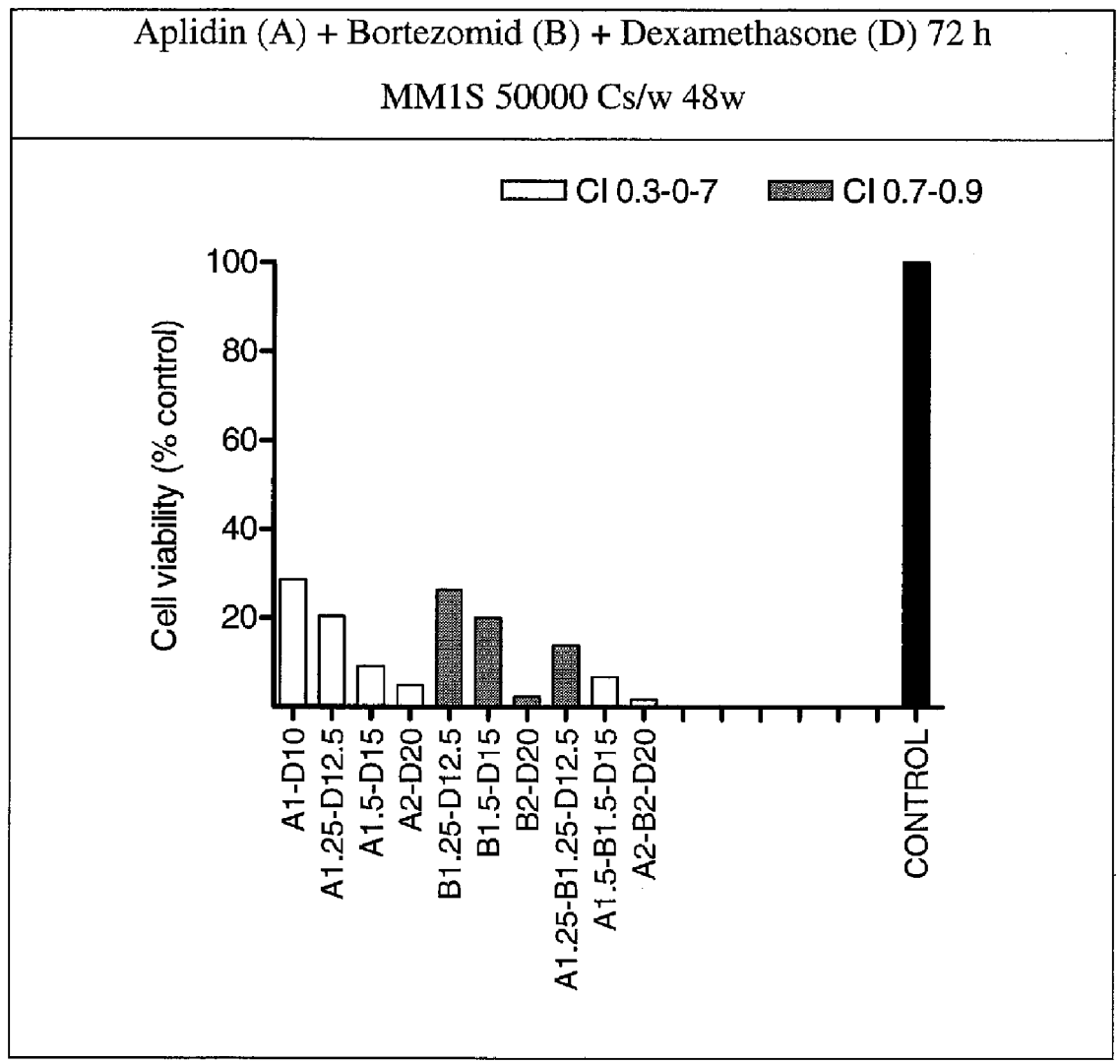
FIG. 81. Combination of Aplidine (A)+Bortezomib (B)+Dexamethasone (D) in MM1S after 72 h of treatment. Aplidine doses are expressed in nM units, Bortezomib doses are expressed in nM units and Dexamethasone doses are expressed in nM units.

The addition of Dexamethasone to the combination of Aplidine with Bortezomib resulted in several doses with a clear trend to synergy (FIG. 81). In FIG. 81 Aplidine doses are expressed in nM units, Bortezomib doses are expressed in nM units and Dexamethasone doses are expressed in nM units.

Combination of Aplidine+Bortezomib+Lenalidomide (Revlimid®)

Figure 82:
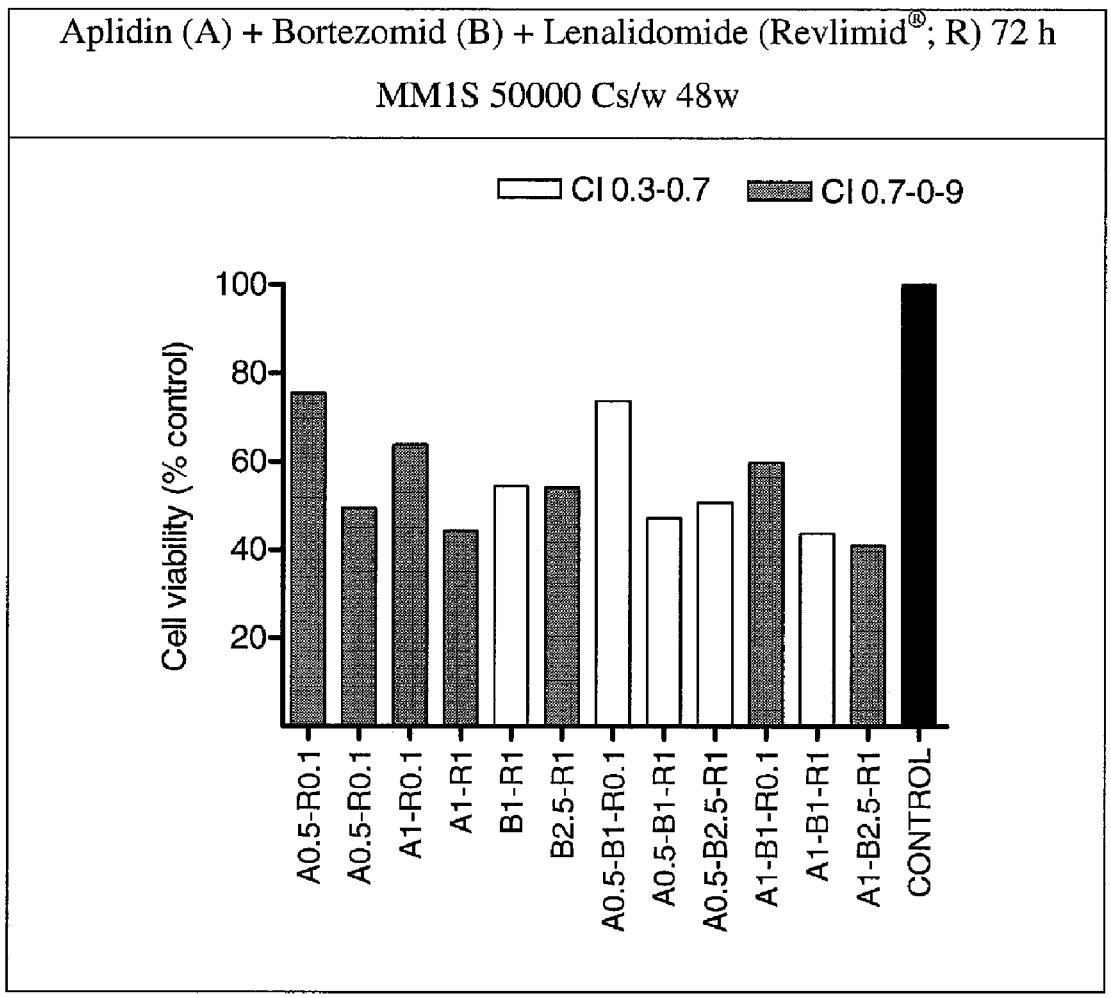
FIG. 82. Combination of Aplidine (A)+Bortezomib (B)+Lenalidomide (Revlimid®; R) in MM1S after 72 h of treatment. Aplidine doses are expressed in nM units, Bortezomib doses are expressed in nM units and Lenalidomide doses are expressed in μM units.

The addition of Bortezomib to the combination of Aplidine with an immunomodulatory agent such as Lenalidomide clearly increased its antitumoral effect with CI in the synergistic range in MM1S (FIG. 82). In FIG. 82 Aplidine doses are expressed in nM units, Bortezomib doses are expressed in nM units and Lenalidomide doses are expressed in µM units.

Combination of Aplidine+Thalidomide+Dexamethasone

Figure 83:
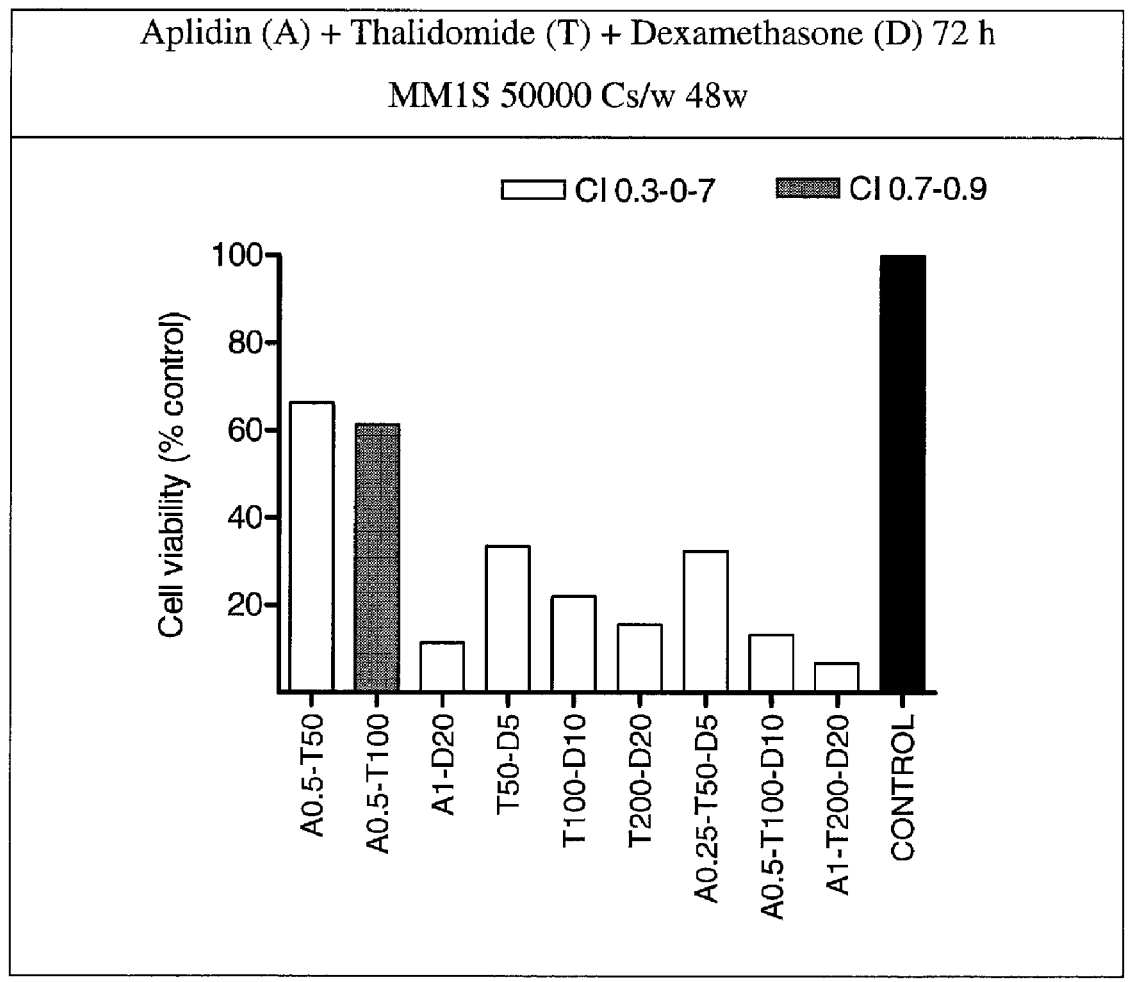
FIG. 83. Combination of Aplidine (A)+Thalidomide (T)+Dexamethasone (D) in MM1S after 72 h of treatment. Aplidine doses are expressed in nM units, Thalidomide doses are expressed in μM units and Dexamethasone doses are expressed in nM units.

This combination showed clear synergy in the triple combinations as can be seen in FIG. 83. In FIG. 83 Aplidine doses are expressed in nM units, Thalidomide doses are expressed in µM units and Dexamethasone doses are expressed in nM units.

Combination of Aplidine+Melphalan+Dexamethasone

Figure 84:
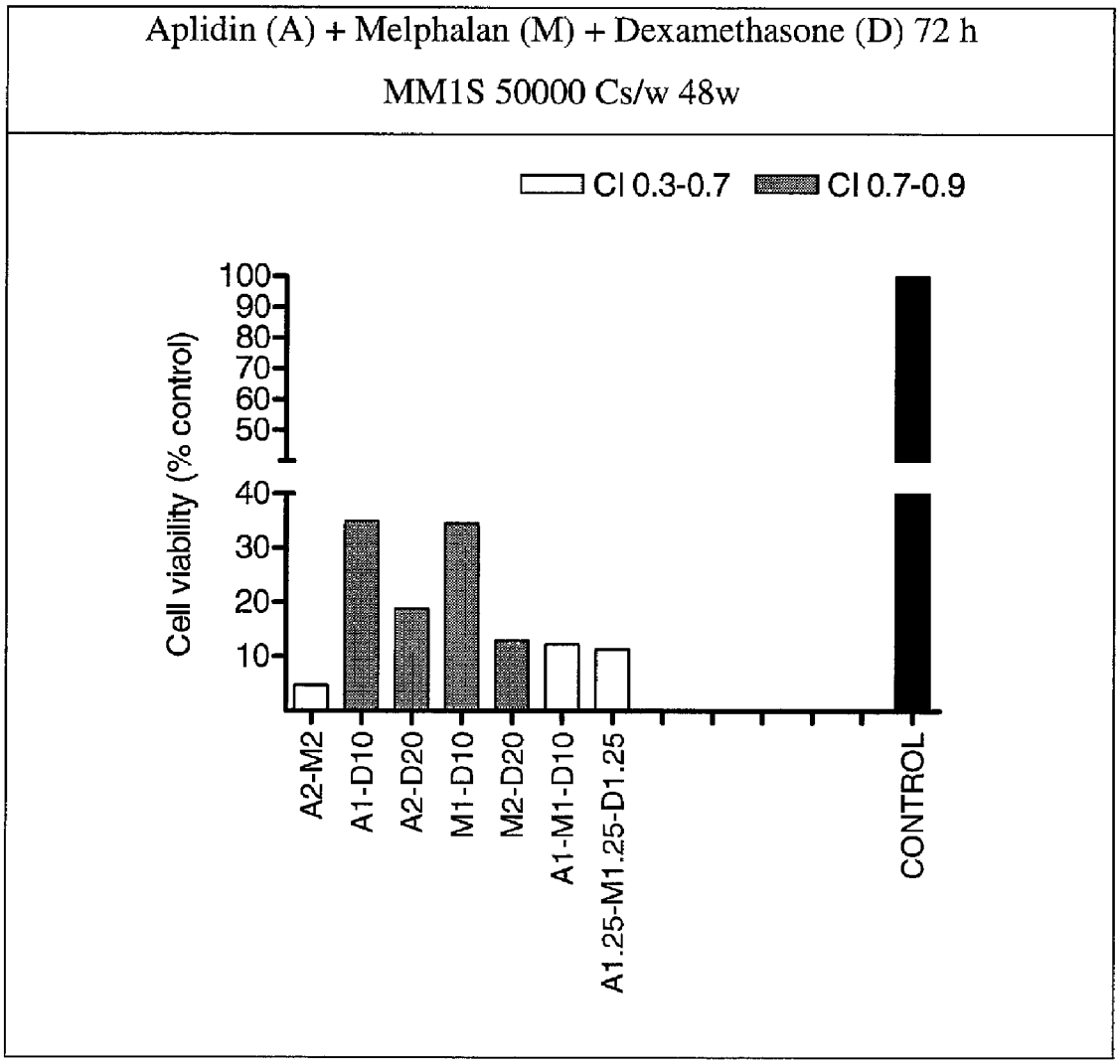
FIG. 84. Combination of Aplidine (A)+Melphalan (M)+Dexamethasone (D) in MM1S after 72 h of treatment. Aplidine doses are expressed in nM units, Melphalan doses are expressed in μM units and Dexamethasone doses are expressed in nM units.

This combination showed also a clear synergistic range, mainly with high doses of the drugs (FIG. 84). In FIG. 84 Aplidine doses are expressed in nM units, Melphalan doses are expressed in µM units and Dexamethasone doses are expressed in nM units.

Combination of Aplidine+Melphalan+Bortezomib

Figure 85:
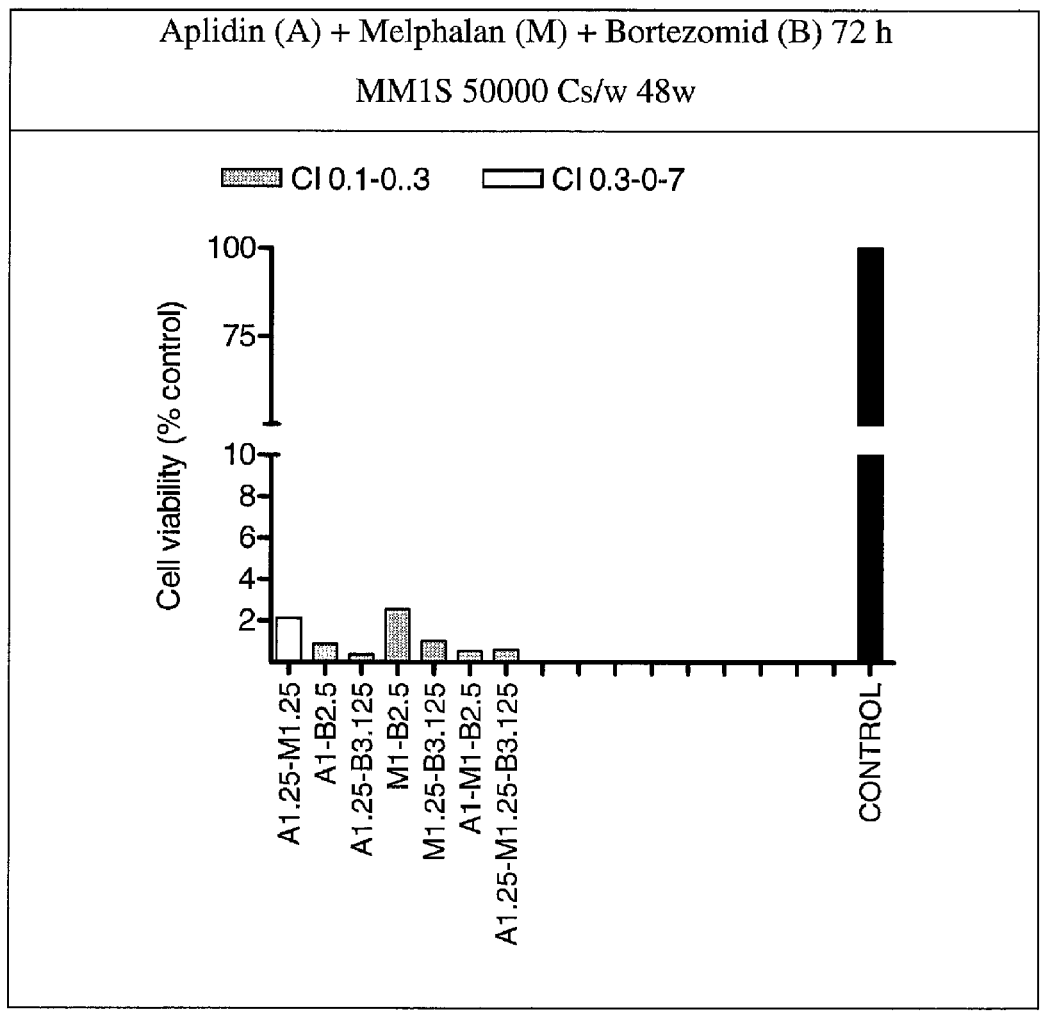
FIG. 85. Combination of Aplidine (A)+Melphalan (M)+Bortezomib (B) in MM1S after 72 h of treatment. Aplidine doses are expressed in nM units, Melphalan doses are expressed in μM units and Bortezomib doses are expressed in nM units.

This combination resulted in CI in the synergistic range when using high doses (FIG. 85). In FIG. 85 Aplidine doses are expressed in nM units, Melphalan doses are expressed in µM units and Bortezomib doses are expressed in nM units.

These findings in respect of Aplidine can be extended to aplidine analogues, derivatives and related compounds. For example, the present invention provides a combination of a compound such as those of WO 02 02596 with an anticancer drug, preferably paclitaxel (Taxol®), doxorubicin, cisplatin, arsenic trioxide, 5-fluorouracil (5-FU), cytosine arabinoside (AraC), carboplatin, 7-ethyl-10-hydroxycamptothecin (SN38), etoposide (VP16), melphalan, dexamethasone, cyclophosphamide, bortezomib, erlotinib, trastuzumab, lenalidomide (Revlimid®), interleukin-2 (IL-2), interferon-α 2 (INF-α), dacarbazine (DTIC), bevacizumab (Avastin®), idarubicin, thalidomide, and rituximab.

Examples of analogues of aplidine which can be used in place of Aplidine itself include the preferred compounds given in WO 02 02596, and in particular we import into this patent specification the discussion of preferred compounds and related aspects given in WO 02 02596. More preferably, the analogues are structurally close to Aplidine, and usually differ from Aplidine in respect of one amino acid or the terminal sidechain. The different amino acid can be in the cyclic part of the molecule or in the sidechain. Many examples of such compounds are given in WO 02 02596, and they are candidates for use in the present invention.

The invention claimed is:

1. A method of treating a cancer selected from breast cancer, prostate cancer, colon cancer, lung cancer, multiple myeloma, and melanoma, comprising administering to a patient in need of such treatment a therapeutically effective amount of aplidine and a therapeutically effective amount of another drug, wherein said drug is selected from paclitaxel, cisplatin, arsenic trioxide, 5-fluorouracil, carboplatin, 7-ethyl-10-hydroxycamptothecin, etoposide, melphalan, dexamethasone, bortezomib, lenalidomide, idarubicin, and rituximab, and wherein said amounts of both drugs together provide a synergistic effect.

2. A method of increasing the therapeutic efficacy of a drug effective in the treatment of a cancer selected from breast cancer, prostate cancer, colon cancer, lung cancer, multiple myeloma, and melanoma, wherein said drug is selected from paclitaxel, cisplatin, arsenic trioxide, 5-fluorouracil, carboplatin, 7-ethyl-10-hydroxycamptothecin, etoposide, melphalan, dexamethasone, bortezomib, lenalidomide, idarubicin, and rituximab, which comprises administering to a patient with said cancer in need thereof said drug and an amount of aplidine, and wherein the amounts of both drugs together provide a synergistic effect.

3. The method according to claim 1, wherein a therapeutically effective amount of a third drug selected from melphalan, dexamethasone, bortezomib, lenalidomide, and thalidomide is administered.

4. The method according to claim 1, wherein said drug is paclitaxel.

5. The method according to claim 1, wherein said drug is cisplatin.

6. The method according to claim 1, wherein said drug is arsenic trioxide.

7. The method according to claim 1, wherein said drug is 5-fluorouracil.

8. The method according to claim 1, wherein said drug is carboplatin.

9. The method according to claim 1, wherein said drug is 7-ethyl-10-hydroxycamptothecin.

10. The method according to claim 1, wherein said drug is etoposide.

11. The method according to claim 1, wherein said drug is melphalan.

12. The method according to claim 1, wherein said drug is dexamethasone.

13. The method according to claim 1, wherein said drug is bortezomib.

14. The method according to claim 1, wherein said drug is lenalidomide.

15. The method according to claim 1, wherein said drug is idarubicin.

16. The method according to claim 1, wherein said drug is rituximab.

17. The method according to any of claims 4, 5 or 7, wherein said method is a method of treating breast cancer.

18. The method according to any of claims 4, 6, 7 or 8, wherein said method is a method of treating prostate cancer.

19. The method according to any one of claims 5, 6, or 8, wherein said method is a method of treating colon cancer.

20. The method according to any one of claims 6, 7 or 9, wherein said method is a method of treating lung cancer.

21. The method according to any one of claims 10 to 14, wherein said method is a method of treating multiple myeloma.

22. The method according to claim 8, wherein said method is a method of treating melanoma.

23. The method according to claim 3, wherein the second drug is lenalidomide and the third drug is dexamethasone.

24. The method according to claim 3, wherein the second drug is bortezomib and the third drug is dexamethasone.

25. The method according to claim 3, wherein the second drug is bortezomib and the third drug is lenalidomide.

26. The method according to claim 3, wherein the second drug is dexamethasone and the third drug is thalidomide.

27. The method according to claim 3, wherein the second drug is dexamethasone and the third drug is melphalan.

28. The method according to claim 3, wherein the second drug is melphalan and the third drug is bortezomib.

29. The method according to any one of claims 23 to 28, wherein said method is a method of treating multiple myeloma.

* * * * *